United States Patent
Jang et al.

(10) Patent No.: US 10,811,615 B2
(45) Date of Patent: Oct. 20, 2020

(54) COMPOUND AND ORGANIC LIGHT EMITTING ELEMENT COMPRISING SAME

(71) Applicant: LG Chem, Ltd., Seoul (KR)

(72) Inventors: Boonjae Jang, Daejeon (KR); Dong Hoon Lee, Daejeon (KR); Jungoh Huh, Daejeon (KR); Minyoung Kang, Daejeon (KR); Dong Uk Heo, Daejeon (KR); Miyeon Han, Daejeon (KR); Min Woo Jung, Daejeon (KR)

(73) Assignee: LG Chem, Ltd. (KR)

( * ) Notice: Subject to any disclaimer, the term of this patent is extended or adjusted under 35 U.S.C. 154(b) by 329 days.

(21) Appl. No.: 15/751,496

(22) PCT Filed: Sep. 8, 2016

(86) PCT No.: PCT/KR2016/010063
§ 371 (c)(1),
(2) Date: Feb. 9, 2018

(87) PCT Pub. No.: WO2017/043874
PCT Pub. Date: Mar. 16, 2017

(65) Prior Publication Data
US 2018/0233673 A1    Aug. 16, 2018

(30) Foreign Application Priority Data

Sep. 8, 2015    (KR) .................. 10-2015-0127066

(51) Int. Cl.
*H01L 51/50* (2006.01)
*H01L 51/00* (2006.01)
(Continued)

(52) U.S. Cl.
CPC ........ *H01L 51/0072* (2013.01); *C07D 251/12* (2013.01); *C07D 401/10* (2013.01); *C07D 403/10* (2013.01); *C07D 471/04* (2013.01); *C07D 471/06* (2013.01); *C07D 487/04* (2013.01); *C07D 519/00* (2013.01); *C09K 11/06* (2013.01); *H01L 51/0054* (2013.01); *H01L 51/0058* (2013.01); *H01L 51/0067* (2013.01);
(Continued)

(58) Field of Classification Search
None
See application file for complete search history.

(56) References Cited

U.S. PATENT DOCUMENTS

| | | |
|---|---|---|
| 7,862,908 B2 | 1/2011 | Cheng et al. |
| 8,785,636 B2 | 7/2014 | Parham et al. |
| 2014/0251816 A1 | 9/2014 | Musselman et al. |

FOREIGN PATENT DOCUMENTS

| | | | | |
|---|---|---|---|---|
| KR | 2011107682 | * | 10/2011 | ............. C09K 11/06 |
| KR | 2011111692 | * | 10/2011 | ............. H01L 51/50 |

(Continued)

OTHER PUBLICATIONS

Search report from International Application No. PCT/KR2016/010063, dated Dec. 20, 2016.
(Continued)

*Primary Examiner* — Gregory D Clark
(74) *Attorney, Agent, or Firm* — Lerner, David, Littenberg, Krumholz & Mentlik, LLP

(57) ABSTRACT

The present application relates to a compound and an organic light emitting device comprising the same.

12 Claims, 1 Drawing Sheet

(51) Int. Cl.

| | | |
|---|---|---|
| *C09K 11/06* | (2006.01) | |
| *C07D 403/10* | (2006.01) | |
| *C07D 487/04* | (2006.01) | |
| *C07D 251/12* | (2006.01) | |
| *C07D 471/04* | (2006.01) | |
| *C07D 401/10* | (2006.01) | |
| *C07D 471/06* | (2006.01) | |
| *C07D 519/00* | (2006.01) | |

(52) U.S. Cl.
CPC ...... *H01L 51/0073* (2013.01); *H01L 51/5056* (2013.01); *C09K 2211/1018* (2013.01); *H01L 51/5012* (2013.01); *H01L 51/5016* (2013.01); *H01L 51/5072* (2013.01); *H01L 51/5092* (2013.01)

(56) References Cited

FOREIGN PATENT DOCUMENTS

| KR | 20110107682 A | 10/2011 | | |
|---|---|---|---|---|
| KR | 20110111692 A | 10/2011 | | |
| KR | 20120072785 A | 7/2012 | | |
| KR | 2014121957 | * 10/2014 | ............ | C09K 11/06 |
| KR | 20140121957 A | 10/2014 | | |
| WO | 2003012890 A2 | 2/2003 | | |

OTHER PUBLICATIONS

Park, Min Su, et al., "An Indole Derivative as a High Triplet Energy Hole Transport Material for Blue Phosphorescent Organic Light-emitting Diodes." Think Solid Films, vol. 548, Received in revised form Sep. 24, 2013, Accpted Sep. 25, 2013, Available online Oct. 3, 2013, pp. 603-607.

Park and Lee, "Indolo Acridine-Based Hole-Transport Materials for Phosphotescent OLEDs With Over 20% External Quantum Efficiency in Deep Blue and Green", Chemistry of Materials, 2011, pp. 4338-4343, American Chemical Society, USA.

Taiwanese Search Report, for TW Application No. 105129021, dated Mar. 12, 2018.

* cited by examiner

[Figure 1]
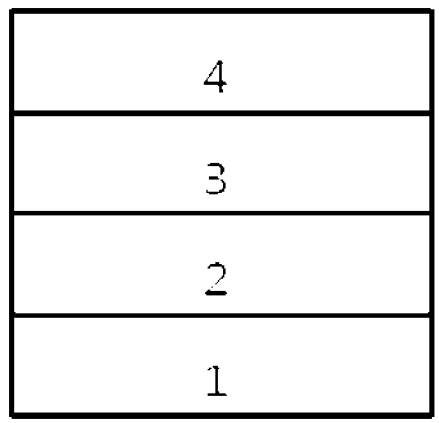
[Figure 2]
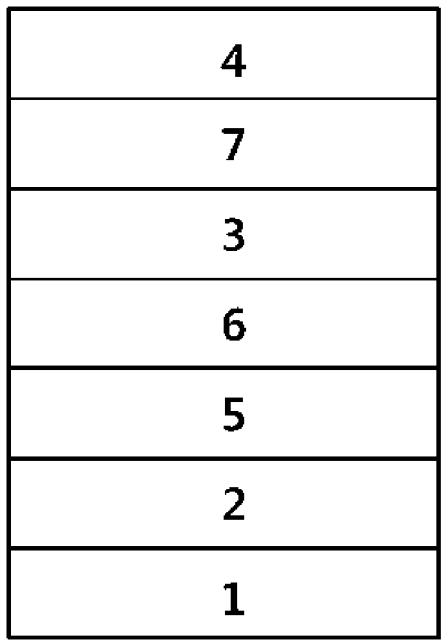

COMPOUND AND ORGANIC LIGHT EMITTING ELEMENT COMPRISING SAME

CROSS-REFERENCE TO RELATED APPLICATIONS

The present application is a national phase entry under 35 U.S.C. § 371 of International Application No. PCT/KR2016/010063, filed Sep. 8, 2016, published in Korean, which claims priority from Korean Patent Application No. 10-2015-0127066 filed on Sep. 8, 2015, with the Korean Intellectual Property Office, the disclosures of which are incorporated herein by reference in their entireties.

TECHNICAL FIELD

The present application relates to a compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present application provides a compound and an organic light emitting device comprising the same.

Technical Solution

The present application provides a compound represented by the following Chemical Formula 1.

[Chemical Formula 1]

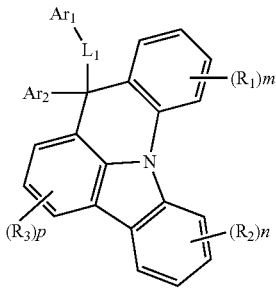

In Chemical Formula 1, $L_1$ is a direct bond; a substituted or unsubstituted arylene group; or a substituted or unsubstituted divalent heterocyclic group, $Ar_1$ is a cyano group; or a substituted or unsubstituted heterocyclic group, $R_1$ to $R_3$ and $Ar_2$ are the same as or different from each other, and are each independently hydrogen; deuterium; a halogen group; a cyano group; a nitro group; a hydroxy group; a substituted or unsubstituted carbonyl group; a substituted or unsubstituted ether group; a substituted or unsubstituted ester group; a substituted or unsubstituted amino group; a substituted or unsubstituted alkyl group; a substituted or unsubstituted silyl group; a substituted or unsubstituted phosphoryl group; a substituted or unsubstituted amine group; a substituted or unsubstituted aryl group; or a substituted or unsubstituted heterocyclic group, p is an integer of 0 to 3, m and n are the same as or different from each other, and are each independently an integer of 0 to 4, and when m, n and p are each an integer of 2 or more, a plurality of structures in the parenthesis are the same as or different from each other.

Further, the present application provides an organic light emitting device including: a first electrode; a second electrode provided to face the first electrode; and one or more organic material layers provided between the first electrode and the second electrode, in which one or more layers of the organic material layers include the above-described compound.

Advantageous Effects

The compound according to an exemplary embodiment of the present application is used for an organic light emitting device and thus may lower the driving voltage of the organic light emitting device, and improve the light efficiency, and lifetime characteristics of the device by thermal stability of the compound.

DESCRIPTION OF DRAWINGS

FIG. 1 illustrates an example of an organic light emitting device in which a substrate 1, a positive electrode 2, a light emitting layer 3, and a negative electrode 4 are sequentially stacked.

FIG. 2 illustrates an example of an organic light emitting device in which a substrate 1, a positive electrode 2, a hole injection layer 5, a hole transport layer 6, a light emitting layer 3, an electron transport layer 7, and a negative electrode 4 are sequentially stacked.

1: Substrate
2: Positive electrode
3: Light emitting layer
4: Negative electrode
5: Hole injection layer
6: Hole transport layer
7: Electron transport layer

BEST MODE

Hereinafter, the present specification will be described in more detail.

The present specification provides a compound represented by Chemical Formula 1.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; a hydroxy group; an alkyl group; a cycloalkyl group; an alkenyl group; an alkoxy group; an aryl group; and a heterocyclic group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neo-pentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branch-chained, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 40. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the group may be

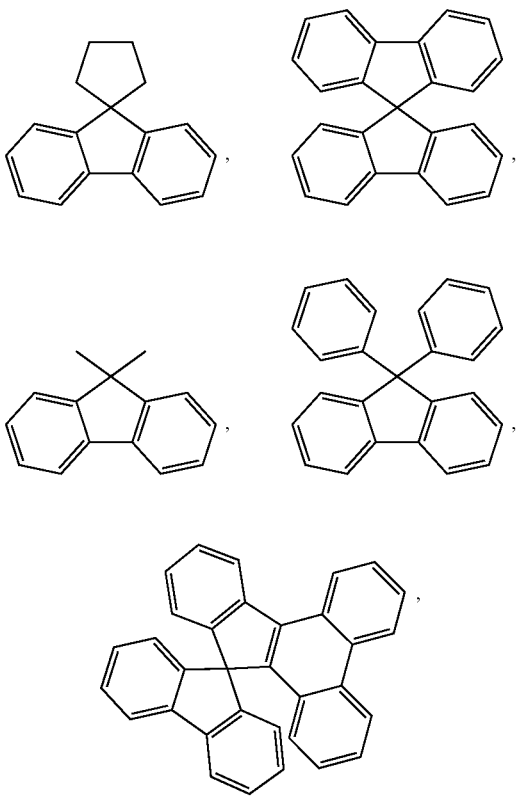

-continued

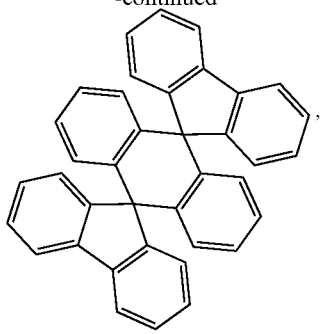

and the like, but is not limited thereto.

In the present specification, a heterocyclic group includes one or more of an atom other than carbon, that is, a heteroatom, and specifically, the heteroatom may include one or more atoms selected from the group consisting of O, N, Se, and S, and the like. The number of carbon atoms of the heterocyclic group is not particularly limited, but is preferably 2 to 60. Examples of the heterocyclic group include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a hydroacridyl group (for example,

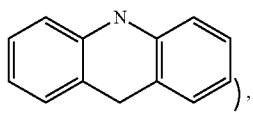 [SMILES: c1ccc2c(c1)Cc1ccccc1N2]

), a pyridazinyl group, a pyrazinyl group, a qinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a dibenzofuranyl group, a benzosilole group, a dibenzosilole group, a phenanthrolinyl group, a thiazolyl group, an isoxazolyl group, an oxadiazolyl group, a thiadiazolyl group, a benzothiazolyl group, a phenothiazinyl group, a phenoxazinyl group, and fused structures thereof, and the like, but are not limited thereto. In addition, examples of the heterocyclic group include a heterocyclic structure including a sulfonyl group, for example,

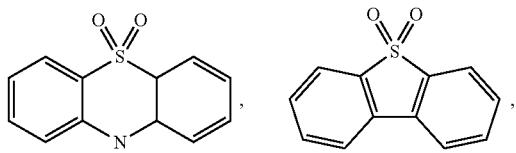 [SMILES: O=S1(=O)c2ccccc2NC2C=CC=CC21 ; O=S1(=O)c2ccccc2-c2ccccc21]

and the like.

In the present specification, the fused structure may be a structure in which an aromatic hydrocarbon ring is fused with the corresponding substituent. Examples of a fused ring of benzimidazole include

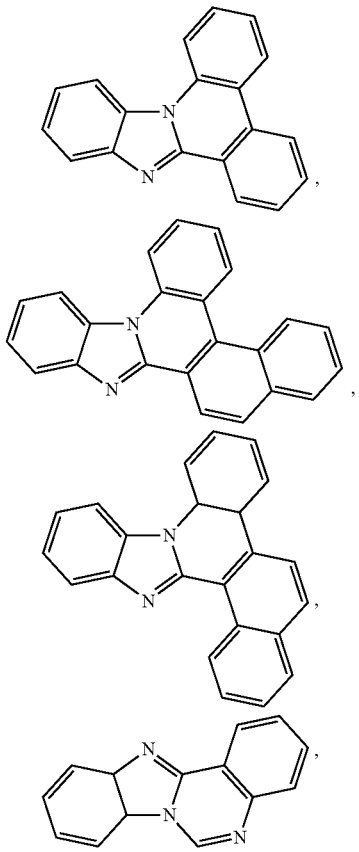

and the like, but are not limited thereto.

In the present specification, the "adjacent" group may mean a substituent substituted with an atom directly linked to an atom in which the corresponding substituent is substituted, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups combine with each other to form a ring means that adjacent groups combine with each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

According to an exemplary embodiment of the present application, $Ar_1$ is a cyano group; or a substituted or unsubstituted heterocyclic group.

According to an exemplary embodiment of the present application, $Ar_1$ is a cyano group; or a substituted or unsubstituted heterocyclic group including one or more of O, N, and S.

According to an exemplary embodiment of the present application, $Ar_1$ is a cyano group; a substituted or unsubstituted pyridyl group; a substituted or unsubstituted pyrimidyl group; a substituted or unsubstituted triazine group; a substituted or unsubstituted pyridazine group; a substituted or unsubstituted quinoline group; a substituted or unsubstituted benzimidazole group; a substituted or unsubstituted benzimidazole fused ring group; a substituted or unsubstituted quinazoline group; a substituted or unsubstituted furan group; a substituted or unsubstituted thiophene group; a substituted or unsubstituted dibenzofuran group; or a substituted or unsubstituted dibenzothiophene group.

According to an exemplary embodiment of the present application, $Ar_1$ is a cyano group; a substituted or unsubstituted pyridyl group; a substituted or unsubstituted pyrimidyl group; a substituted or unsubstituted triazine group; a substituted or unsubstituted pyridazine group; a substituted or unsubstituted quinoline group; a substituted or unsubstituted benzimidazole group; a substituted or unsubstituted benzimidazole fused ring group; a substituted or unsubstituted quinazoline group; a substituted or unsubstituted furan group; a substituted or unsubstituted thiophene group; a substituted or unsubstituted dibenzofuran group; or a substituted or unsubstituted dibenzothiophene group.

According to an exemplary embodiment of the present application, in the definition of $Ar_1$, the "substituted or unsubstituted" means being unsubstituted or substituted with at least one selected from deuterium; a halogen group; a cyano group; a $C_1$ to $C_{10}$ alkyl group; a $C_6$ to $C_{12}$ aryl group; and a $C_2$ to $C_{10}$ heterocyclic group.

According to an exemplary embodiment of the present application, in the definition of $Ar_1$, the "substituted or unsubstituted" means being unsubstituted or substituted with at least one selected from deuterium; fluorine; a cyano group; a methyl group; an ethyl group; a phenyl group; a biphenyl group; a naphthalene group; a phenanthrene group; a pyrimidine group; a quinoline group; and a pyridine group.

According to an exemplary embodiment of the present application, in the definition of $Ar_1$, the "substituted or unsubstituted" means being unsubstituted or substituted with a $C_6$ to $C_{12}$ aryl group.

According to an exemplary embodiment of the present application, in the definition of $Ar_1$, the "substituted or unsubstituted" means being unsubstituted or substituted with a phenyl group.

According to an exemplary embodiment of the present application, $L_1$ is a direct bond; or a substituted or unsubstituted arylene group.

According to an exemplary embodiment of the present application, $L_1$ is a direct bond; a substituted or unsubstituted phenylene group; a substituted or unsubstituted biphenylene group; a substituted or unsubstituted terphenyl group; a substituted or unsubstituted naphthylene group; or a substituted or unsubstituted fluorene group.

According to an exemplary embodiment of the present application, $L_1$ is a direct bond; a phenylene group which is unsubstituted or substituted with an aryl group; a biphenylene group which is unsubstituted or substituted with an aryl group; a terphenyl group; a naphthylene group; or a fluorene group which is unsubstituted or substituted with an aryl group or an alkyl group.

According to an exemplary embodiment of the present application, $L_1$ is a direct bond; a phenylene group which is unsubstituted or substituted with a phenyl group; a biphenylene group which is unsubstituted or substituted with a phenyl group; a terphenyl group; a naphthylene group; or a fluorene group which is unsubstituted or substituted with an aryl group or a phenyl group or a methyl group.

According to an exemplary embodiment of the present application, $Ar_2$ is hydrogen; a substituted or unsubstituted aryl group; or a substituted or unsubstituted heterocyclic group.

According to an exemplary embodiment of the present application, $Ar_2$ is hydrogen; a substituted or unsubstituted aryl group; or a substituted or unsubstituted heterocyclic group including N.

According to an exemplary embodiment of the present application, $Ar_2$ is hydrogen; a substituted or unsubstituted phenyl group; a substituted or unsubstituted biphenyl group; a substituted or unsubstituted naphthyl group; a substituted or unsubstituted pyrene group; a substituted or unsubstituted pyridyl group; a substituted or unsubstituted pyrimidine group; a substituted or unsubstituted pyridazine group; a substituted or unsubstituted pyrazine group; or a substituted or unsubstituted triazine group.

According to an exemplary embodiment of the present application, $Ar_2$ is a substituted or unsubstituted phenyl group; a substituted or unsubstituted biphenyl group; a substituted or unsubstituted naphthyl group; a substituted or unsubstituted pyrene group; or a substituted or unsubstituted pyridyl group.

According to an exemplary embodiment of the present application, $Ar_2$ is a phenyl group; a biphenyl group; a naphthyl group; a pyrene group; or a pyridyl group.

According to an exemplary embodiment of the present application, $R_1$ to $R_3$ are the same as or different from each other, and are each independently hydrogen; deuterium; a cyano group; a substituted or unsubstituted carbonyl group; a substituted or unsubstituted ether group; a substituted or unsubstituted silyl group; a substituted or unsubstituted alkyl group; a substituted or unsubstituted aryl group; or a substituted or unsubstituted heterocyclic group.

According to an exemplary embodiment of the present application, $R_1$ to $R_3$ are the same as or different from each other, and are each independently hydrogen; deuterium; a cyano group; a carbonyl group substituted with an aryl group; an ether group; a silyl group; a methyl group; an ethyl group; a butyl group; a phenyl group; a naphthyl group; a biphenyl group; or a pyridine group.

According to an exemplary embodiment of the present application, $R_1$ to $R_3$ are the same as or different from each other, and are each independently hydrogen; deuterium; a cyano group; a carbonyl group substituted with a phenyl group; an ether group; a silyl group; a tert-butyl group; a phenyl group; or a pyridine group.

According to an exemplary embodiment of the present application, the compound represented by Chemical Formula 1 may be any one selected among the following structural formulae.

[Compound 1]

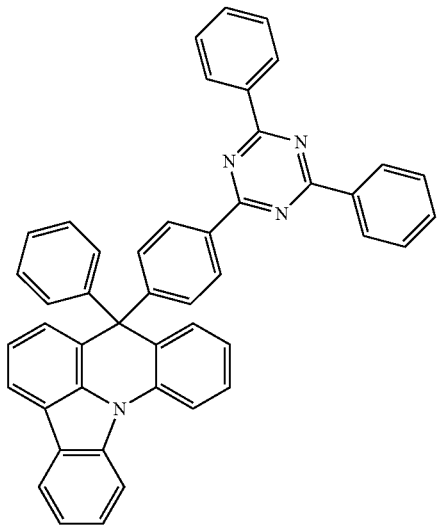

[Compound 2]
[Compound 3]
[Compound 4]
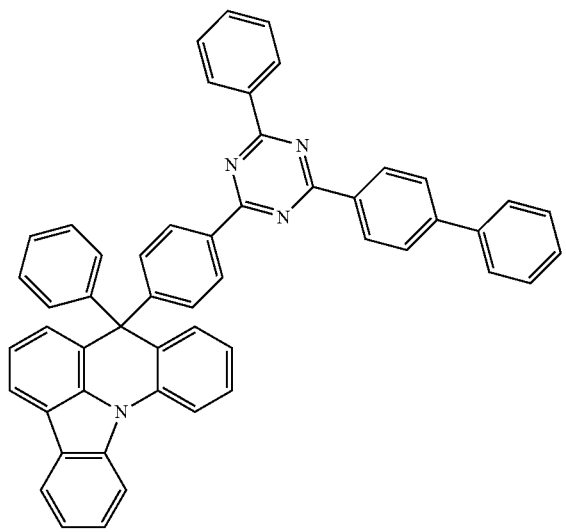
[Compound 5]
[Compound 6]
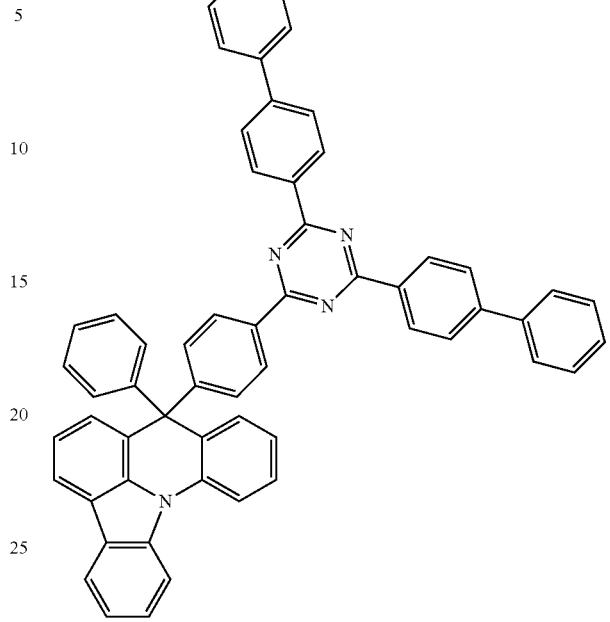
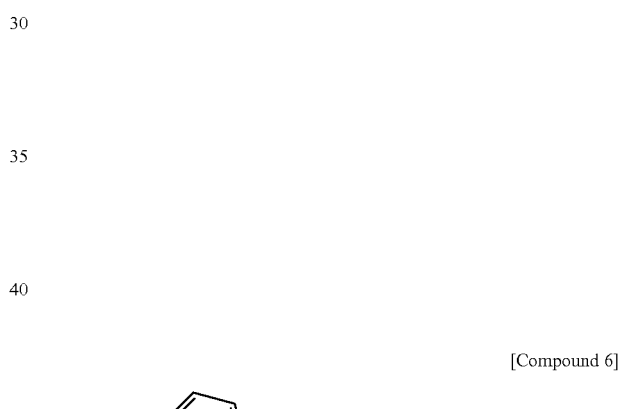
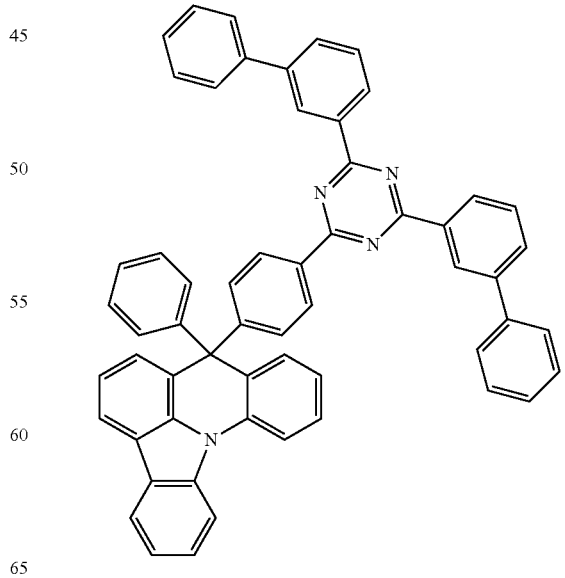

[Compound 7]
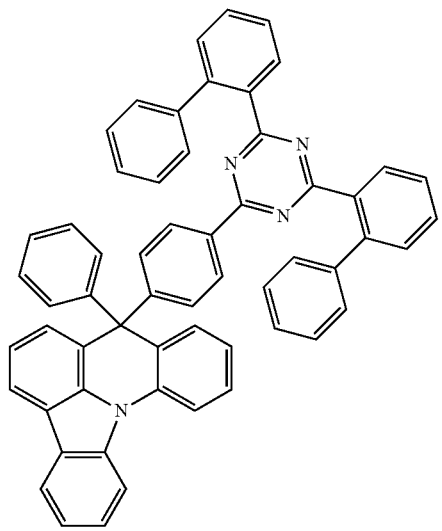
[Compound 8]
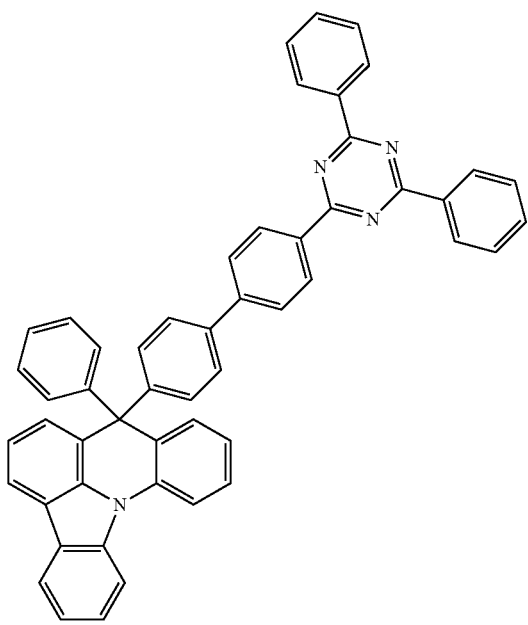
[Compound 9]
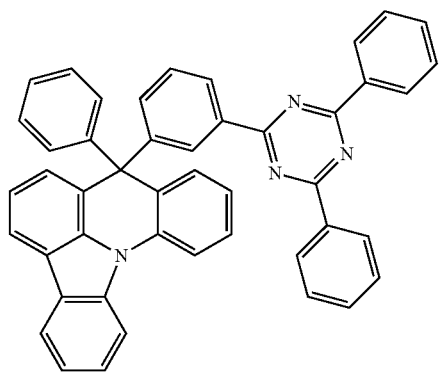
[Compound 10]
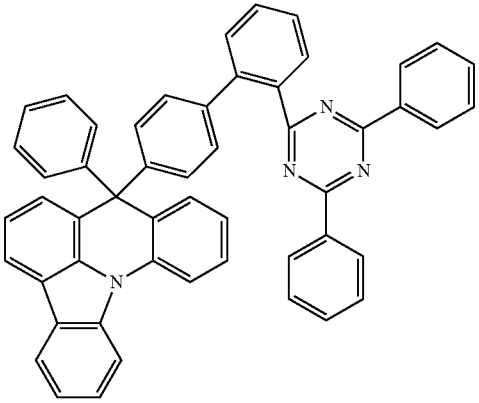
[Compound 11]
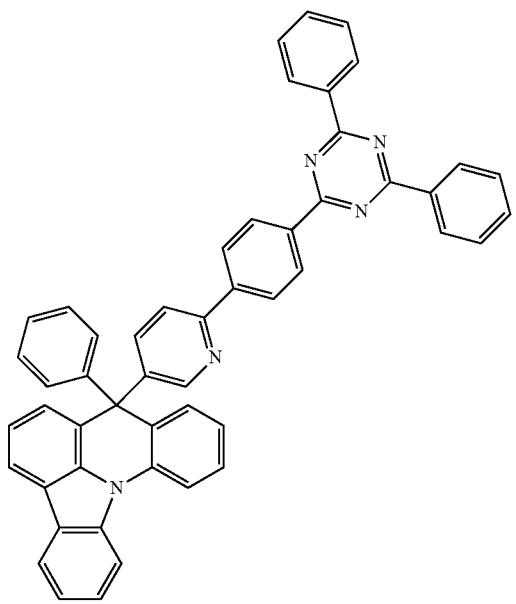
[Compound 12]
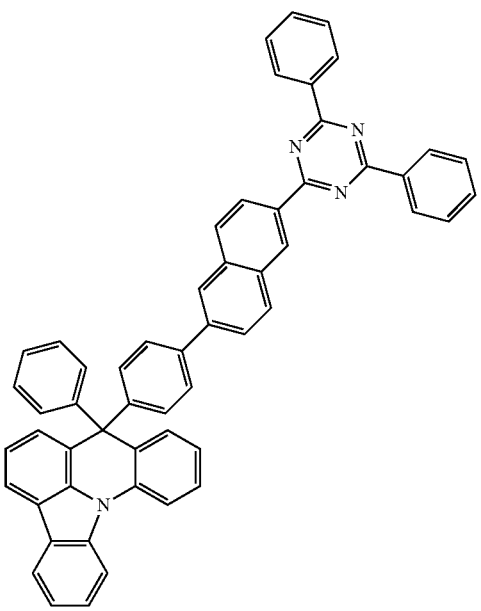

[Compound 13]
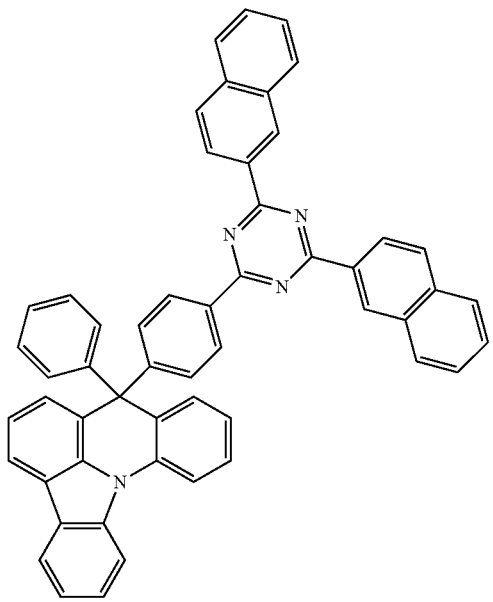
[Compound 14]
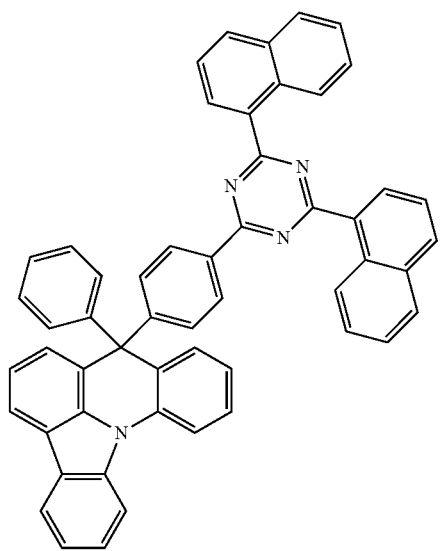
[Compound 15]
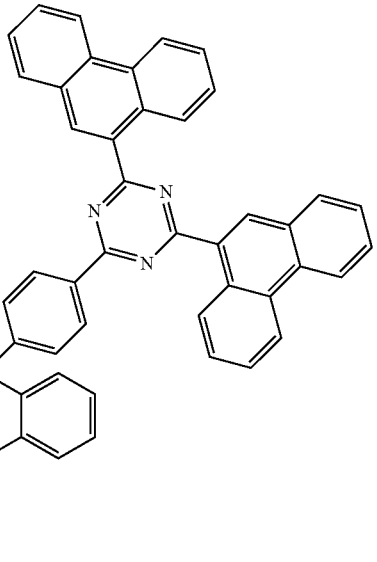
[Compound 16]
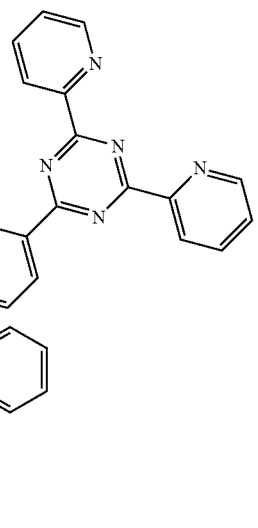
[Compound 17]
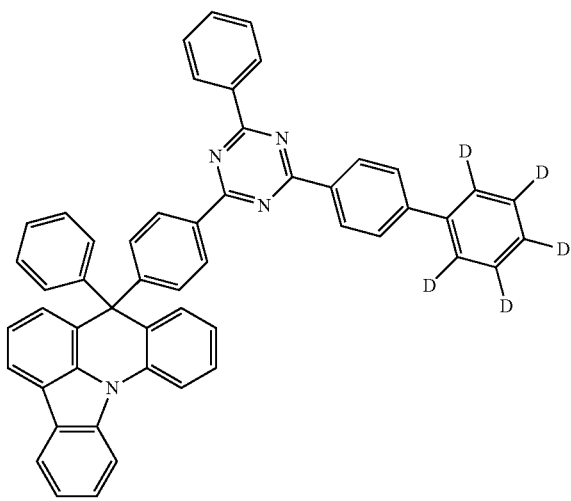

[Compound 18]
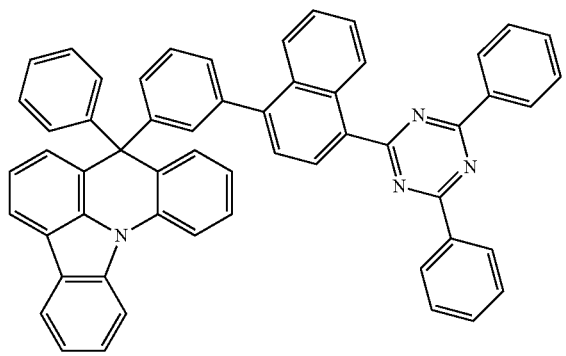
[Compound 19]
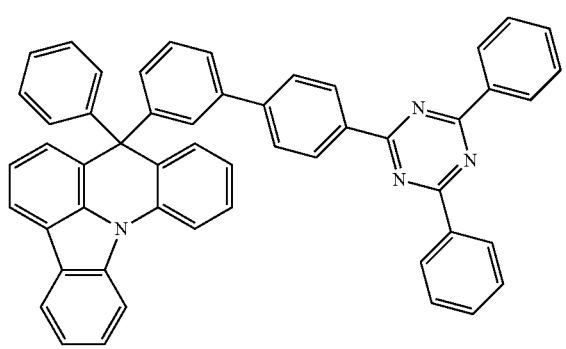
[Compound 20]
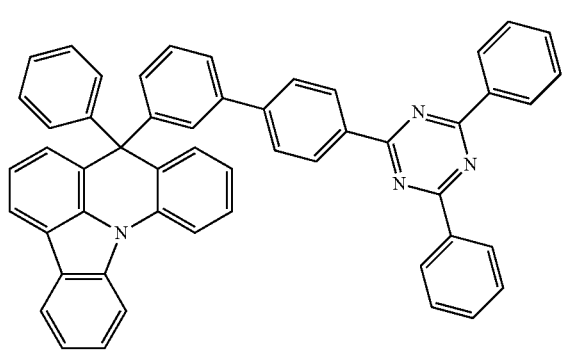
[Compound 21]
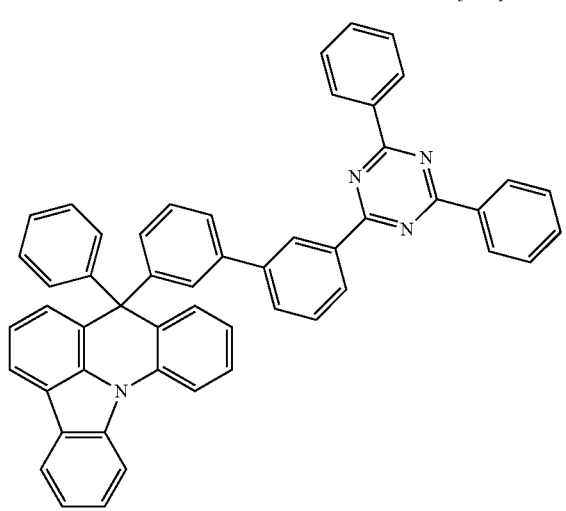
[Compound 22]
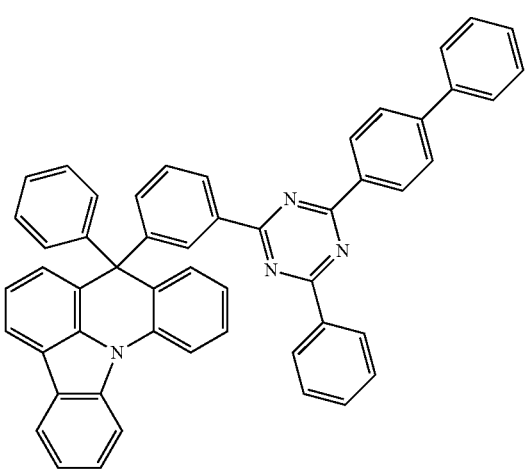
[Compound 23]
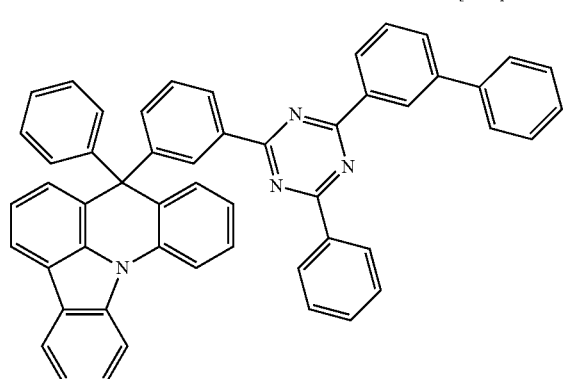
[Compound 24]
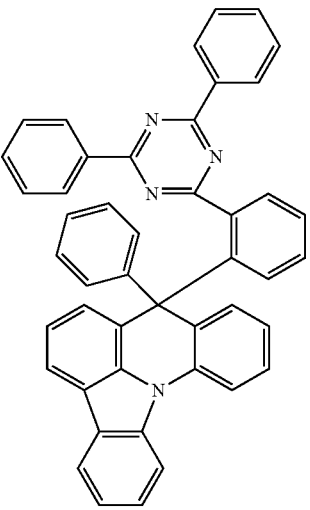

[Compound 25]
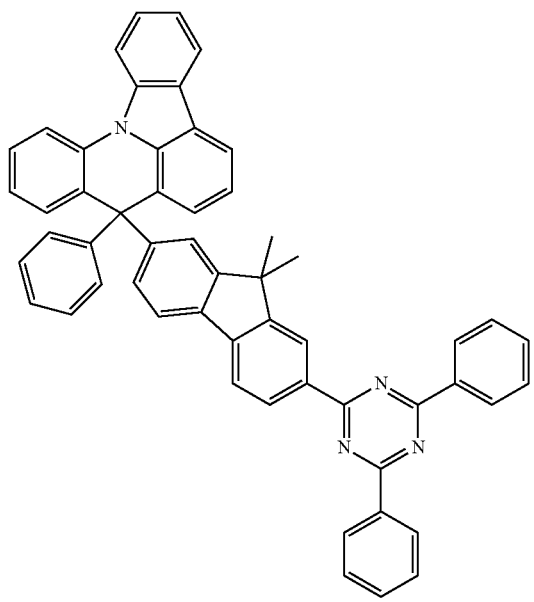
[Compound 27]
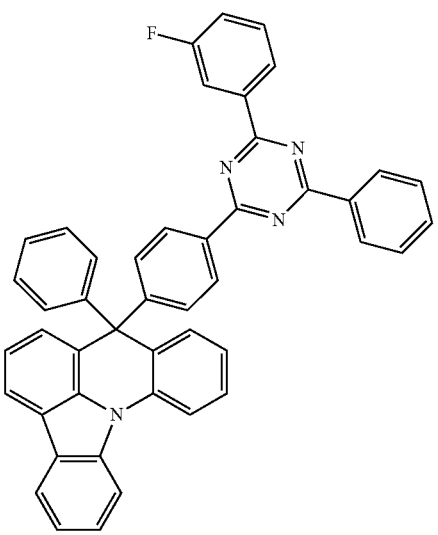
[Compound 26]
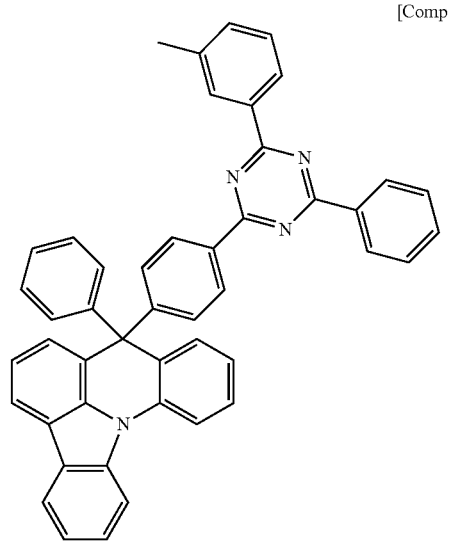
[Compound 28]
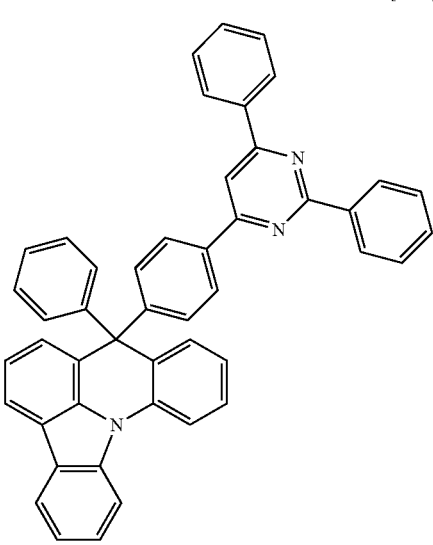

[Compound 29]
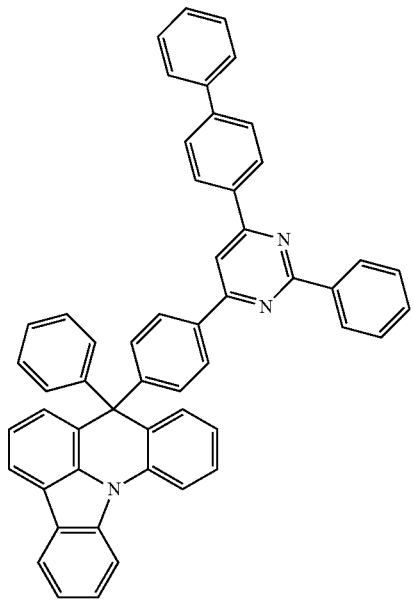
[Compound 31]
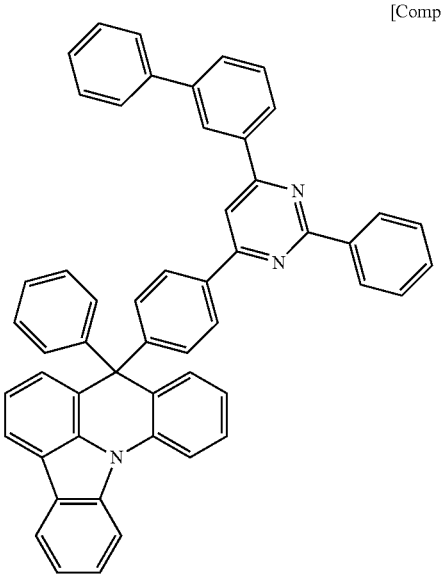
[Compound 30]
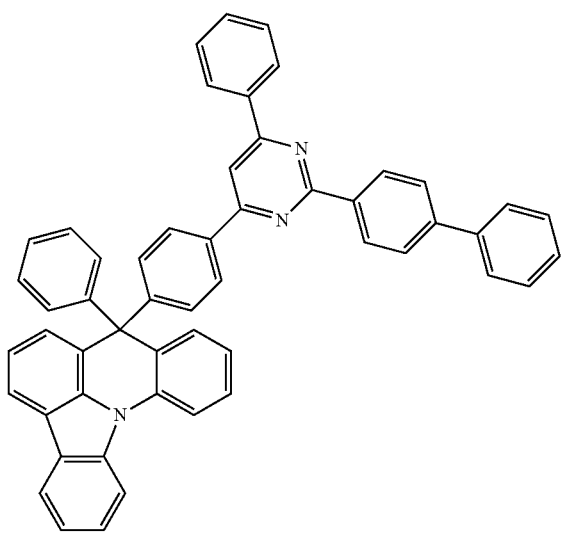
[Compound 32]
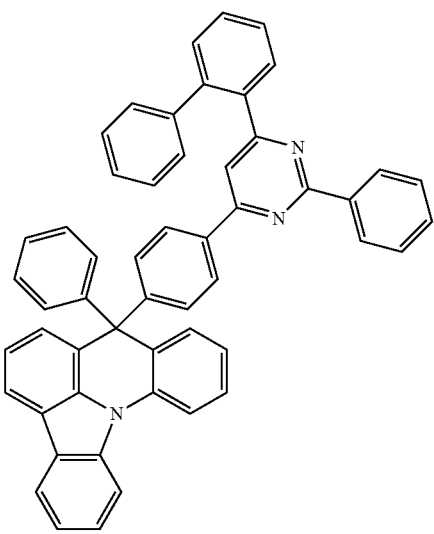

[Compound 33]
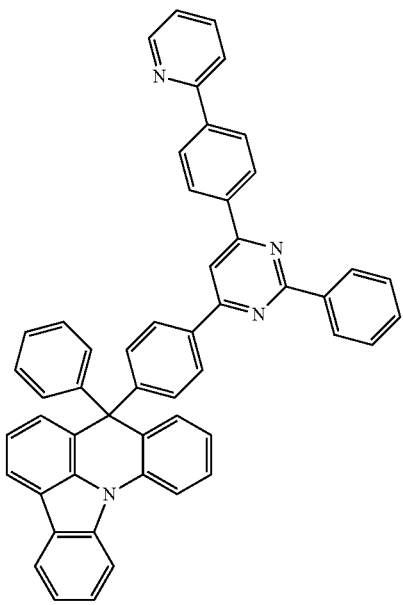
[Compound 34]
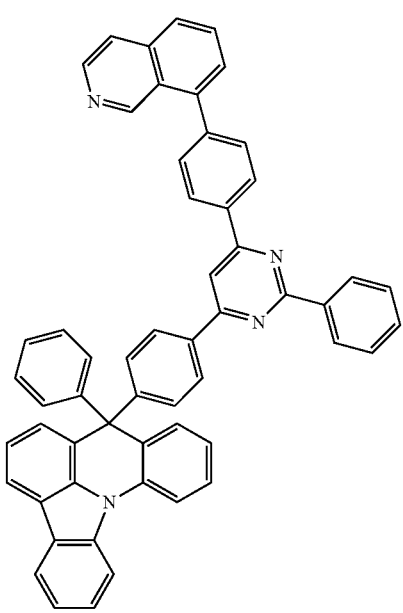
[Compound 35]
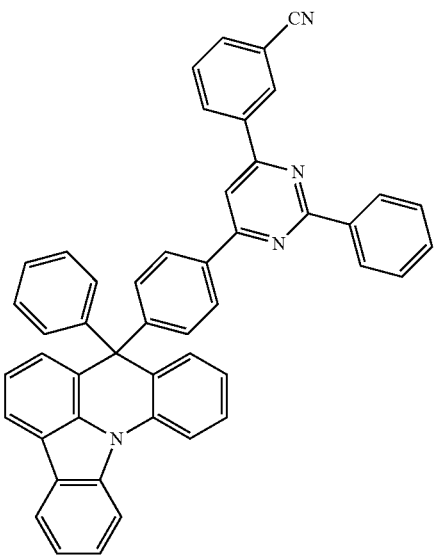
[Compound 36]
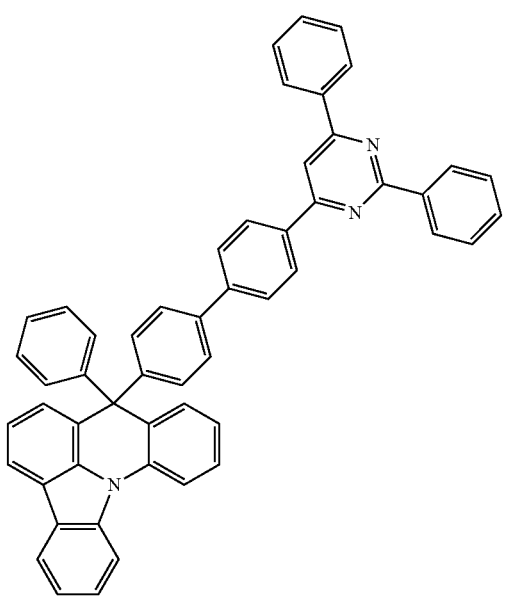

[Compound 37]
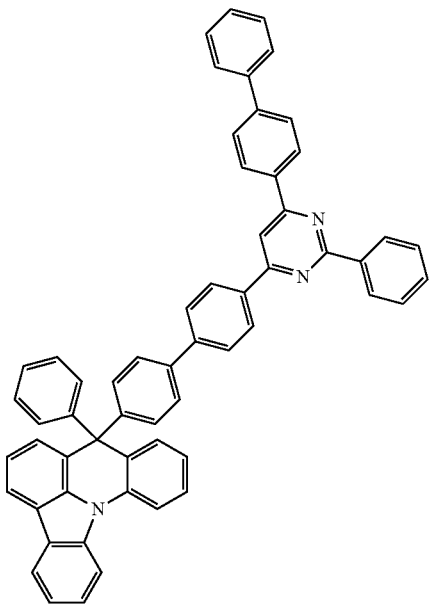
[Compound 40]
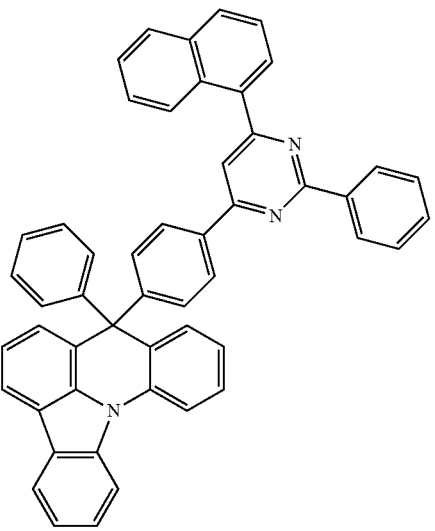
[Compound 38]
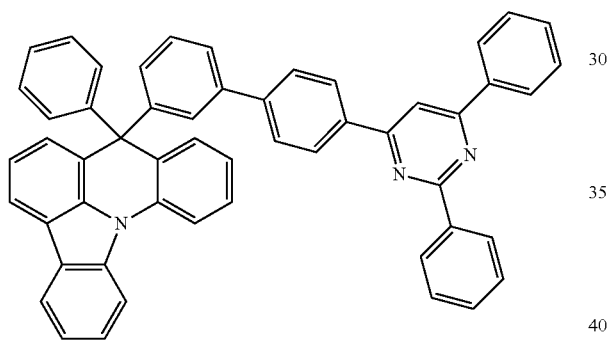
[Compound 39]
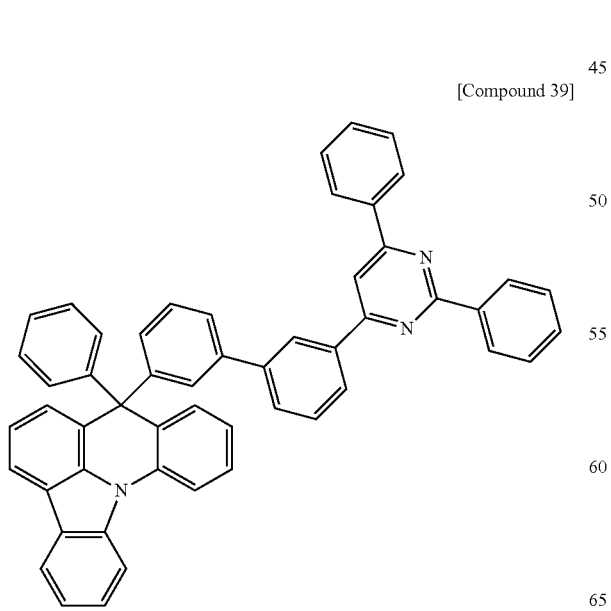
[Compound 41]
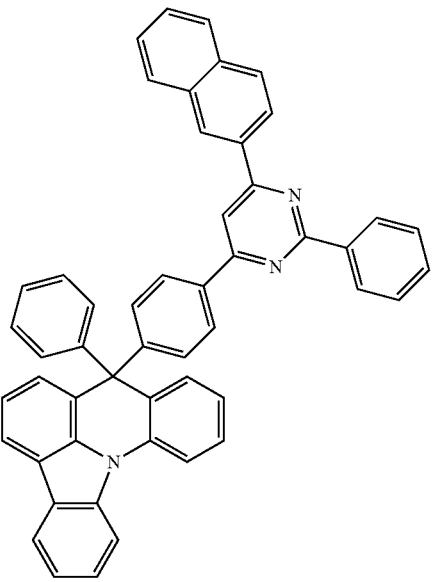

[Compound 42]
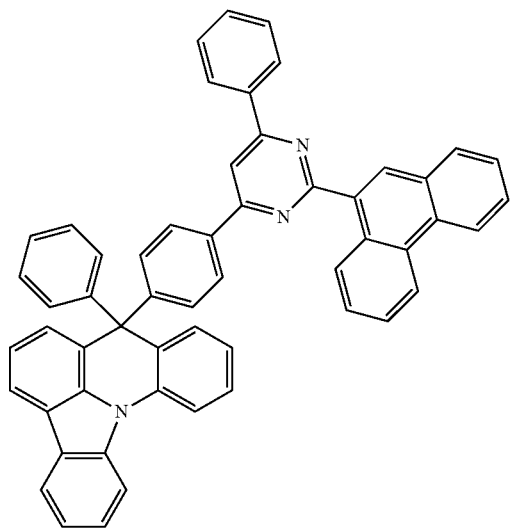
[Compound 45]
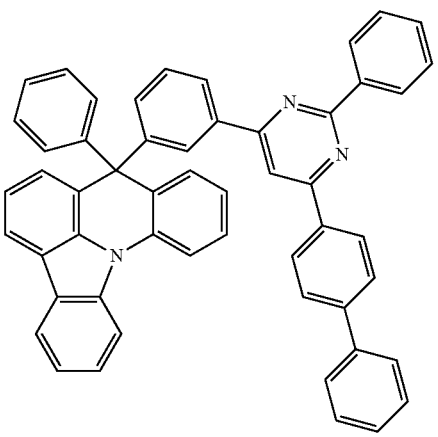
[Compound 43]
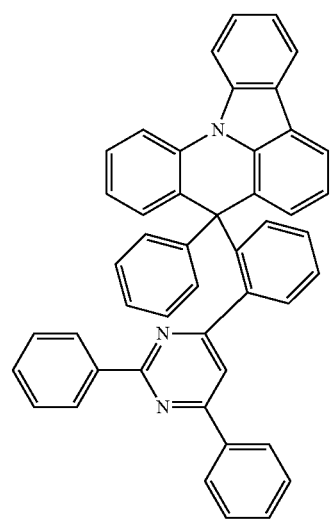
[Compound 46]
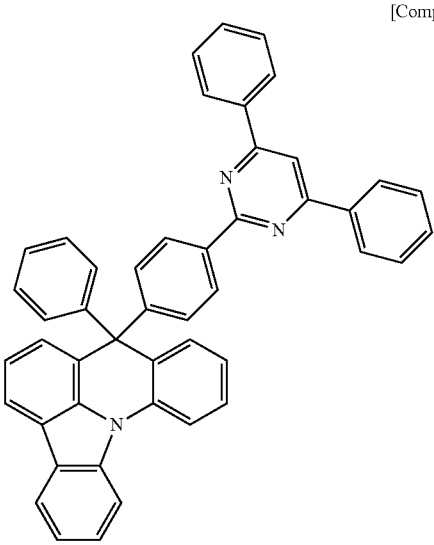
[Compound 44]
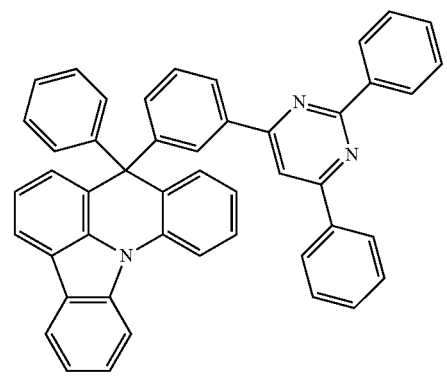
[Compound 47]
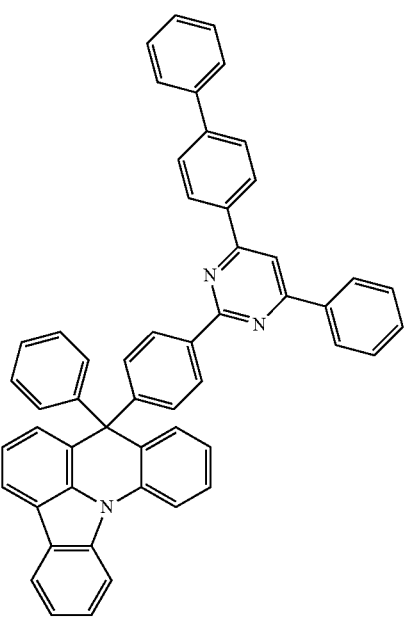

[Compound 48]
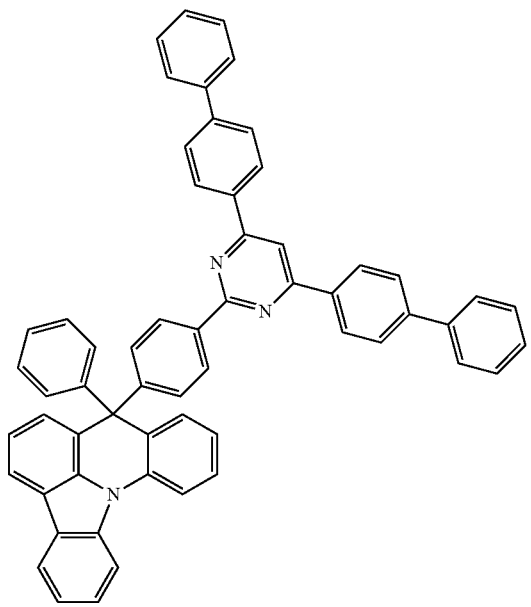
[Compound 49]
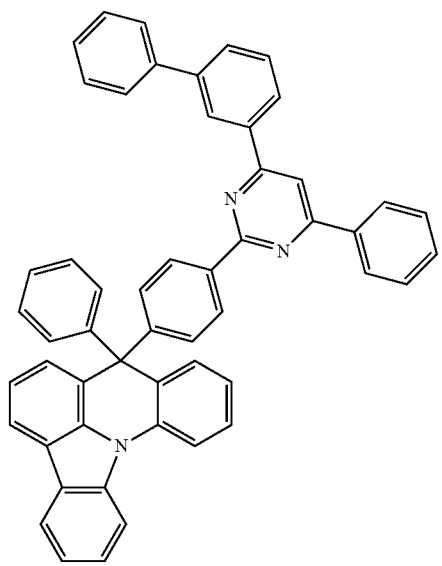
[Compound 50]
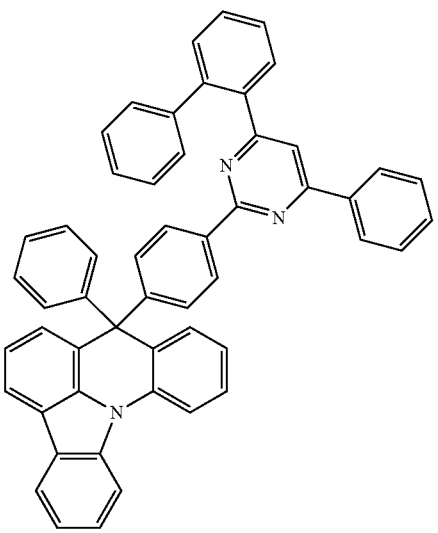
[Compound 51]
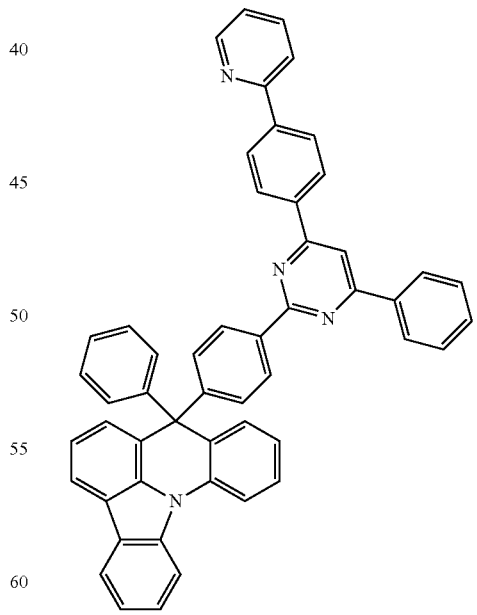

[Compound 52]
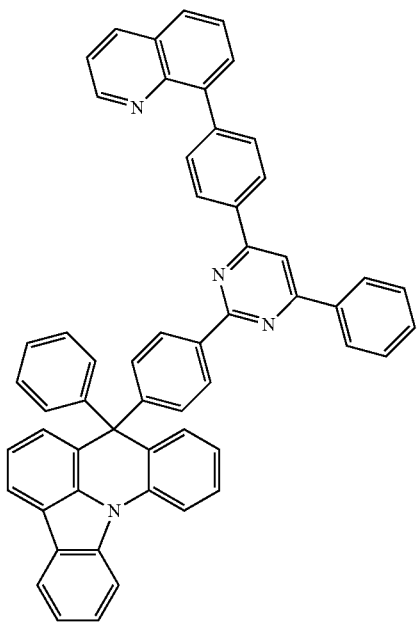
[Compound 53]
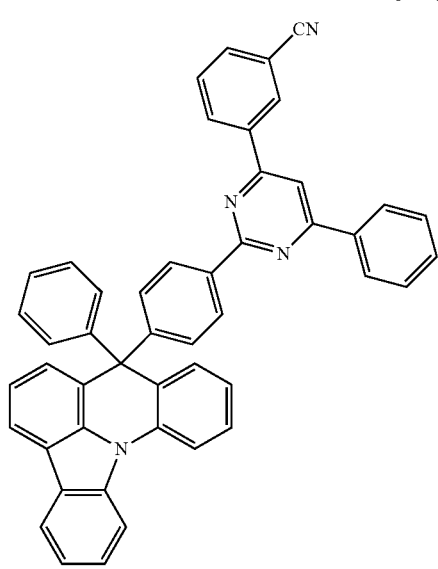
[Compound 54]
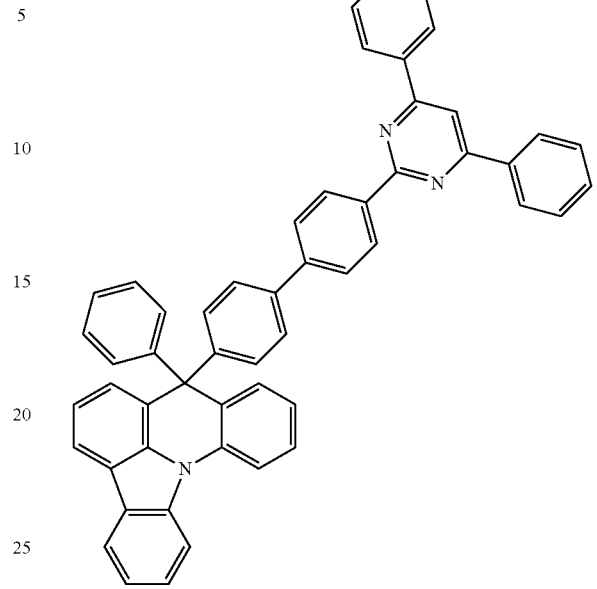
[Compound 55]
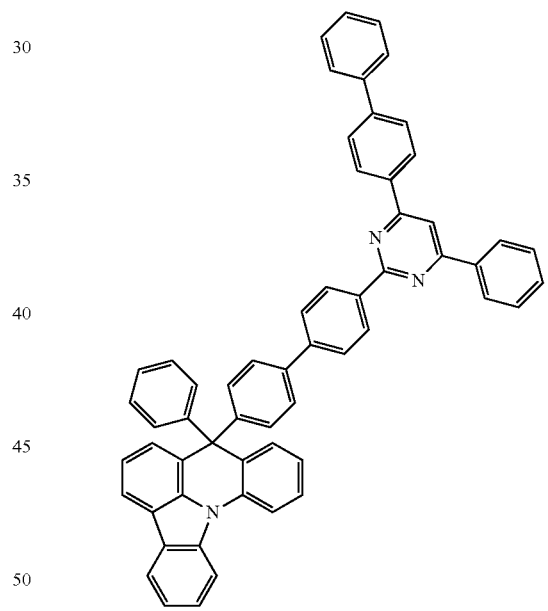
[Compound 56]
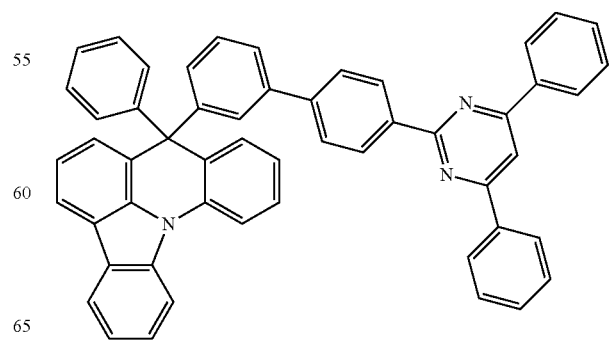

[Compound 57]
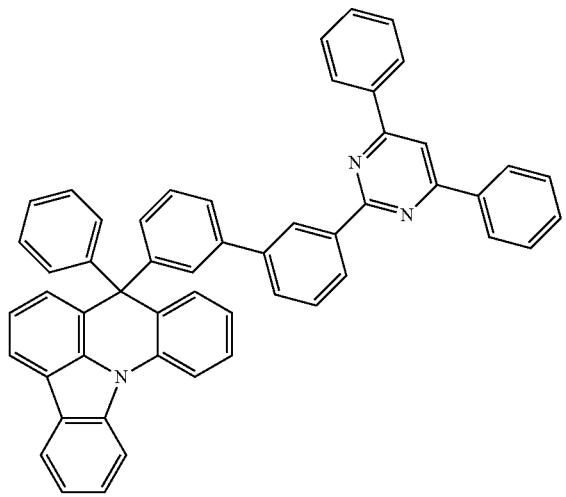
[Compound 58]
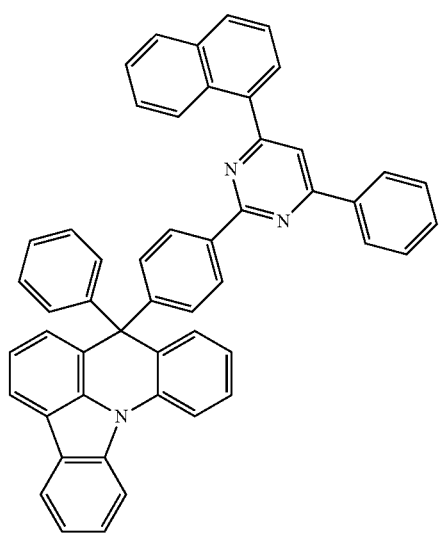
[Compound 59]
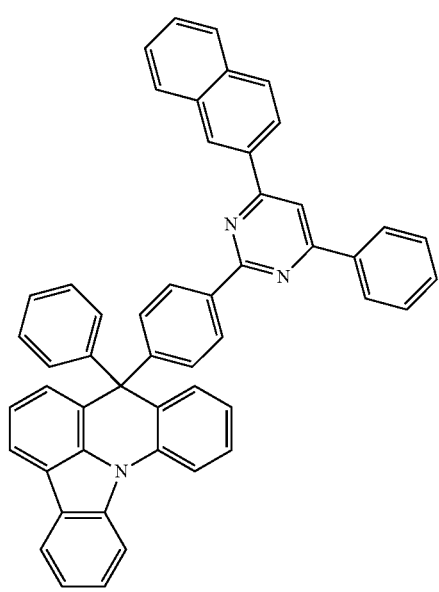
[Compound 60]
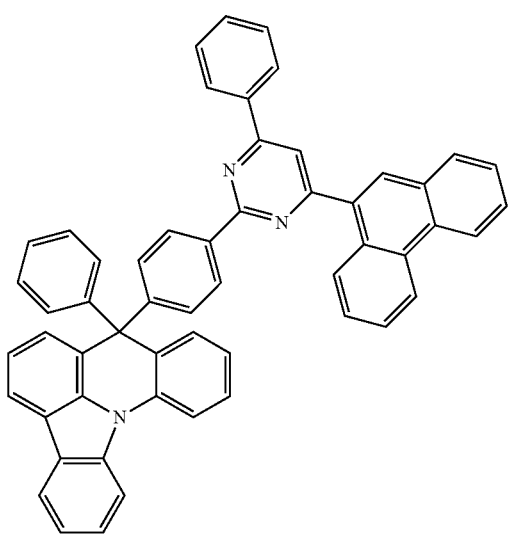
[Compound 61]
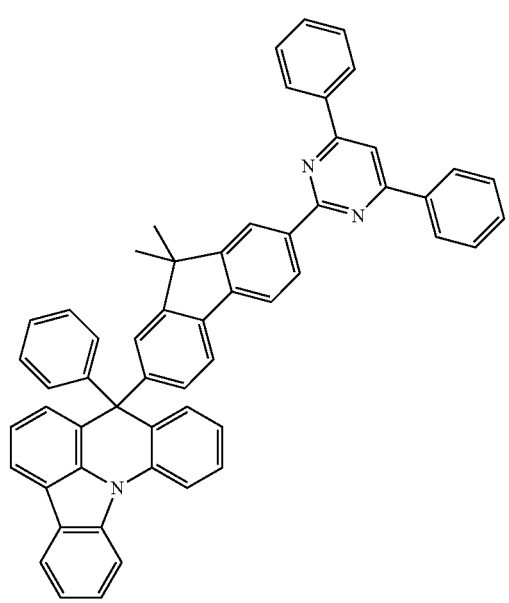

[Compound 62]
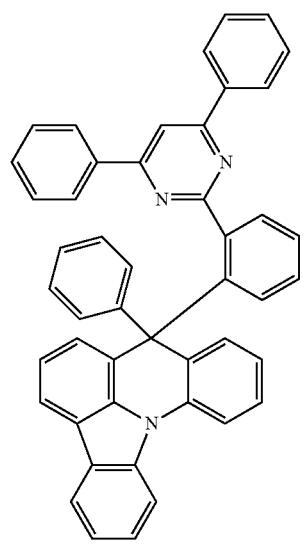
[Compound 65]
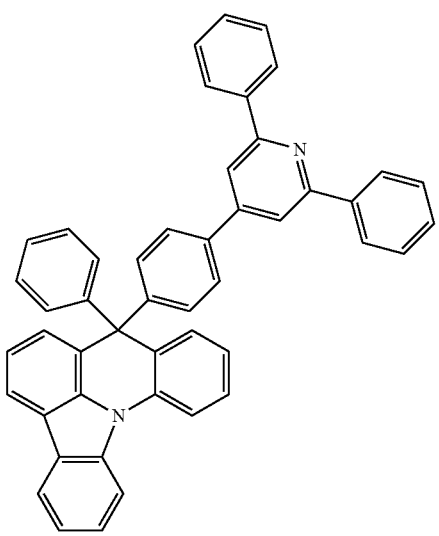
[Compound 63]
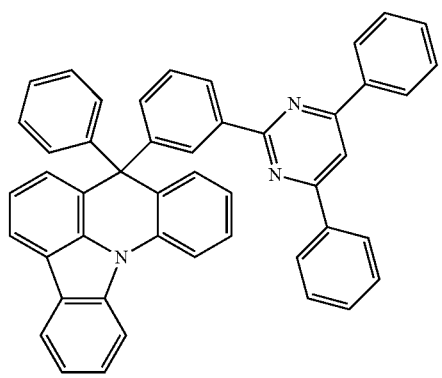
[Compound 66]
[Compound 64]
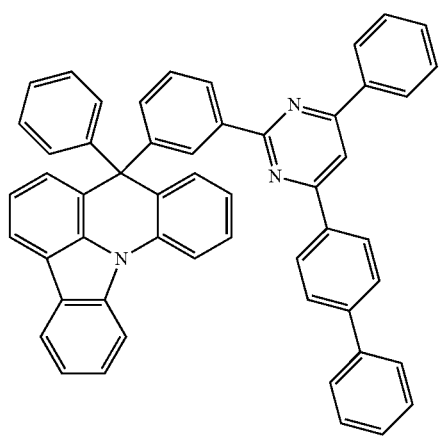
[Compound 67]
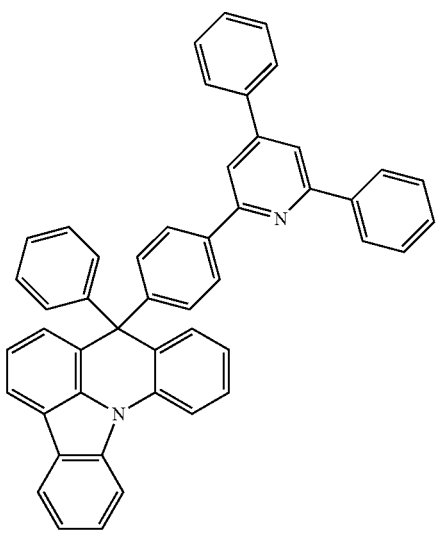

[Compound 68]
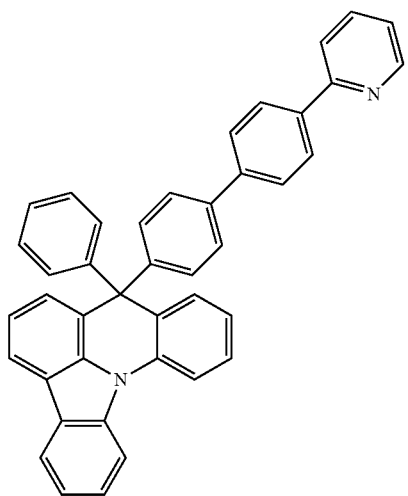
[Compound 69]
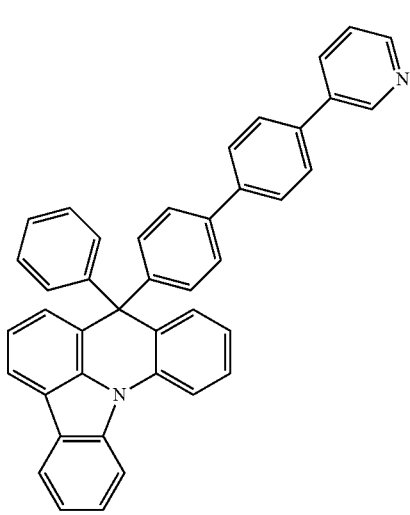
[Compound 70]
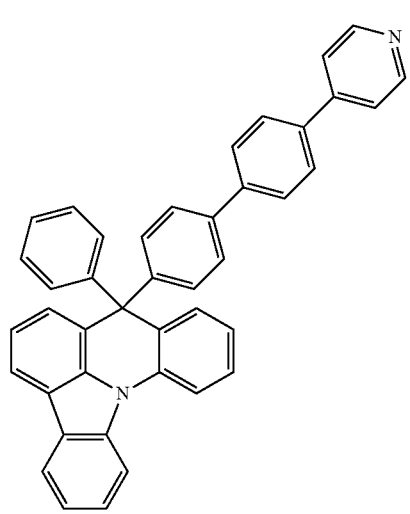
[Compound 71]
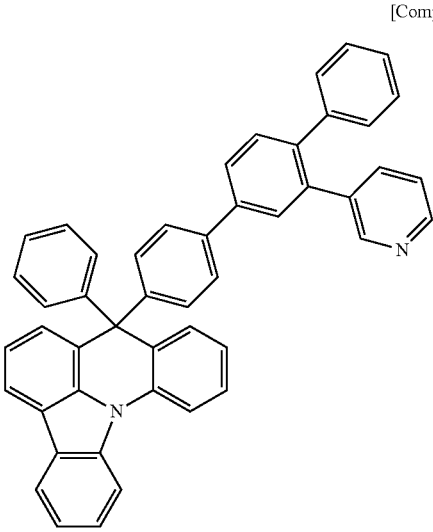
[Compound 72]
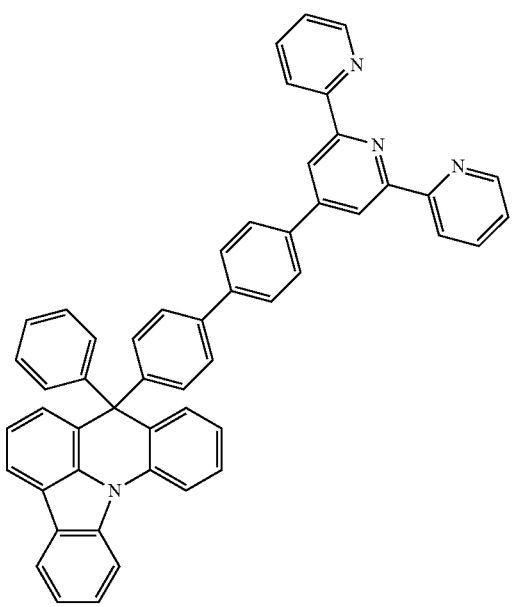

[Compound 73]
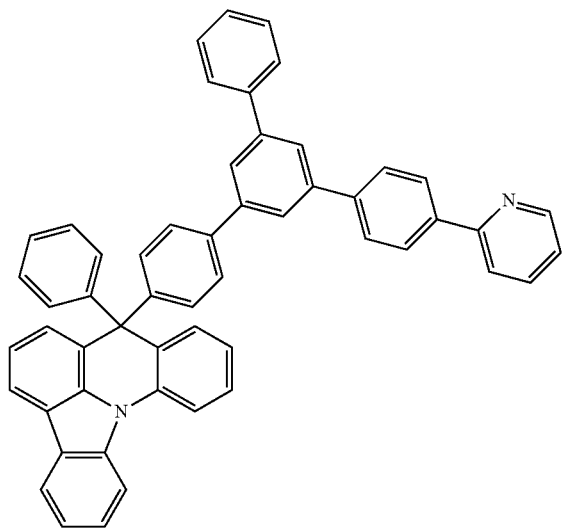
[Compound 74]
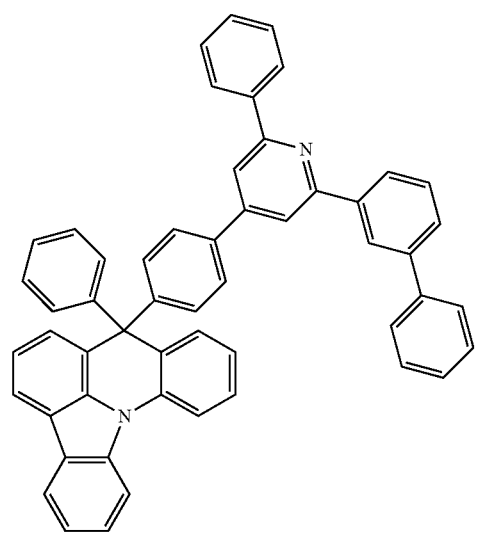
[Compound 75]
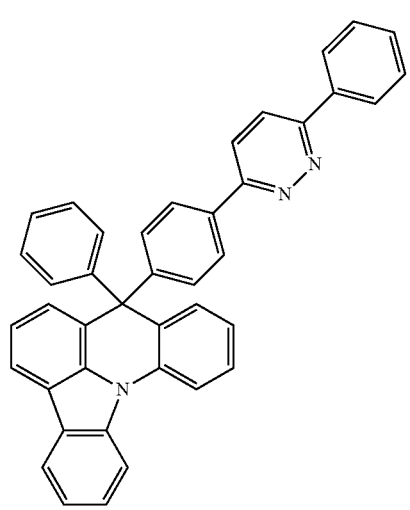
[Compound 76]
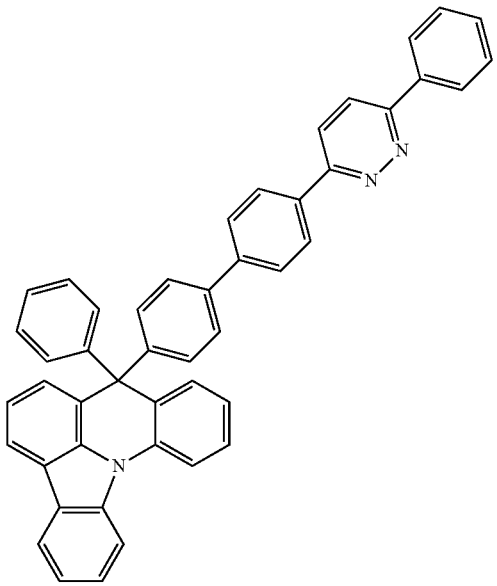
[Compound 77]
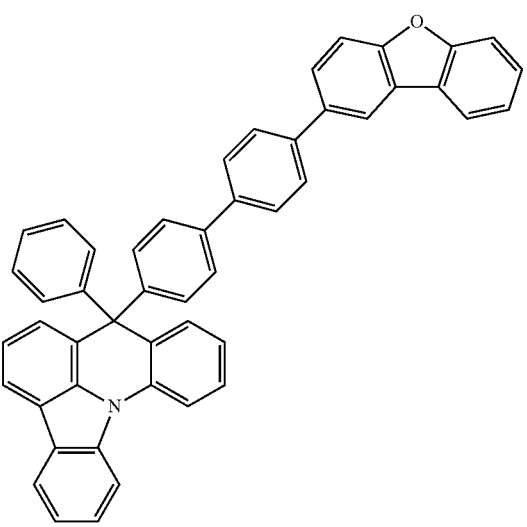
[Compound 78]
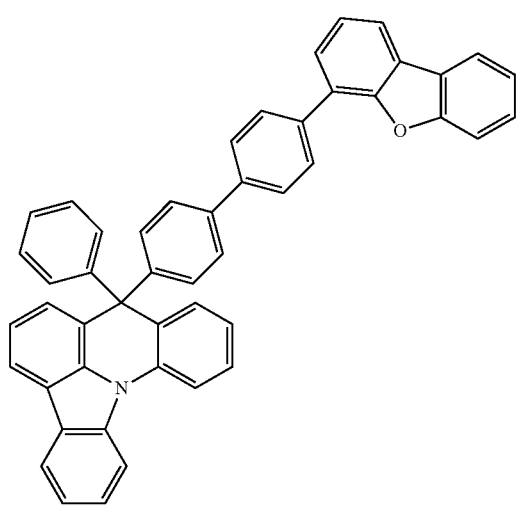

[Compound 79]
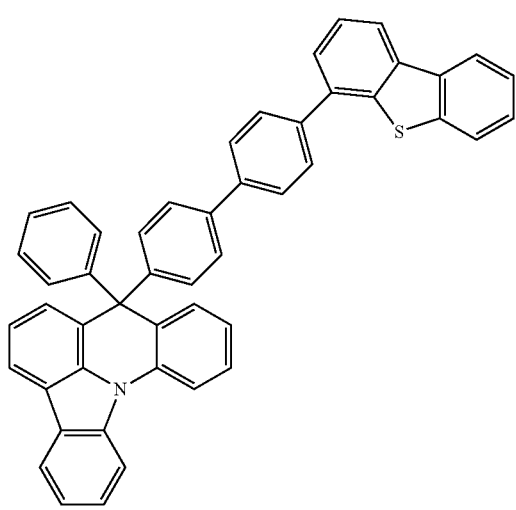
[Compound 80]
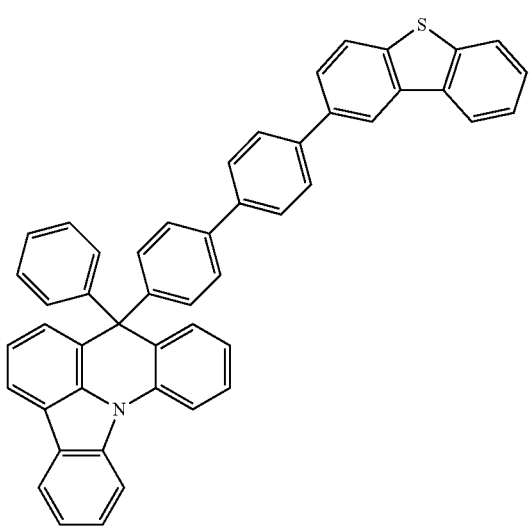
[Compound 81]
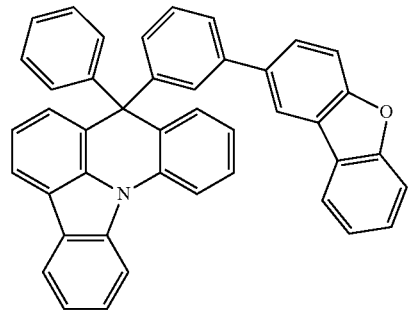
[Compound 82]
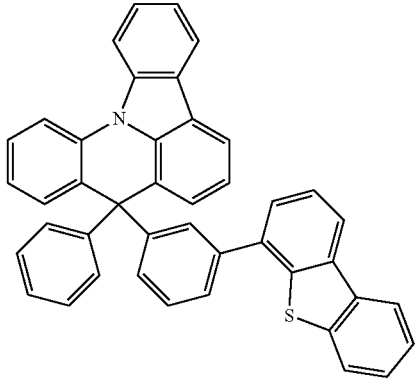
[Compound 83]
[Compound 84]
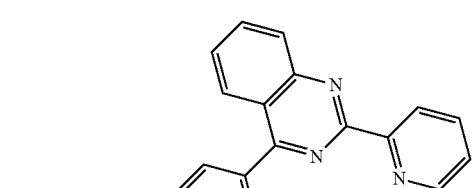

[Compound 85]
[Compound 86]
[Compound 87]
[Compound 88]
[Compound 89]
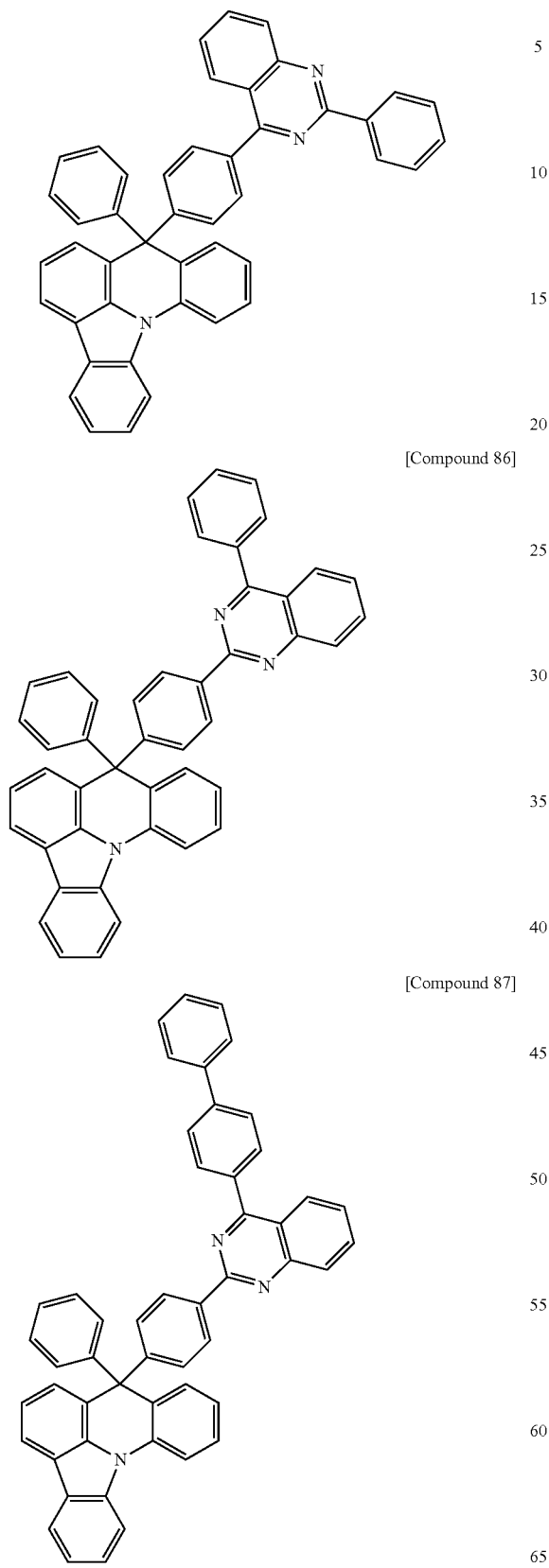
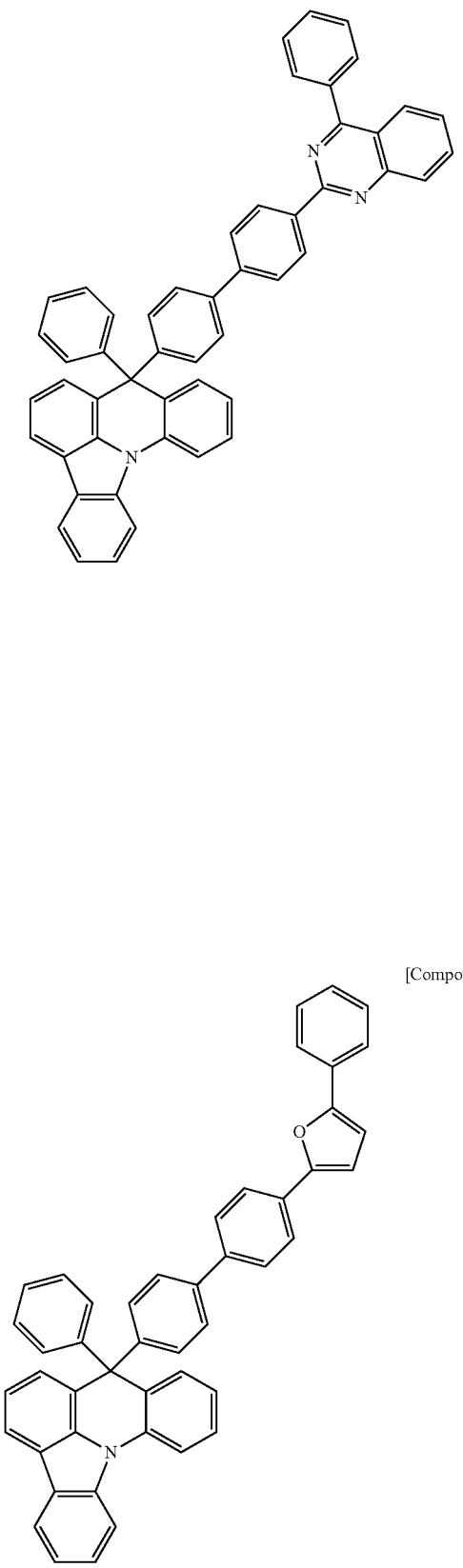

[Compound 90]
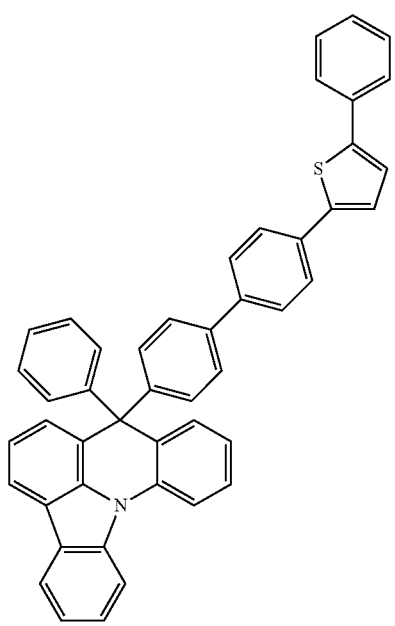
[Compound 91]
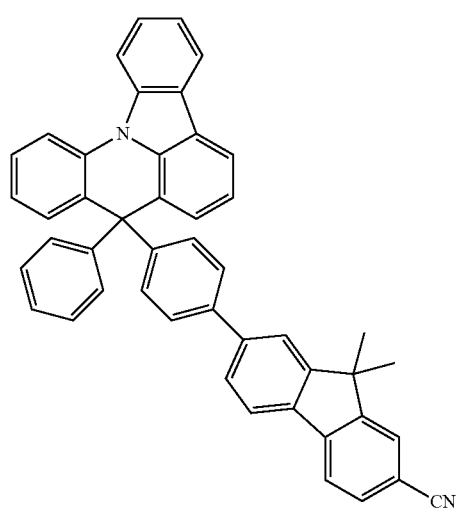
[Compound 92]
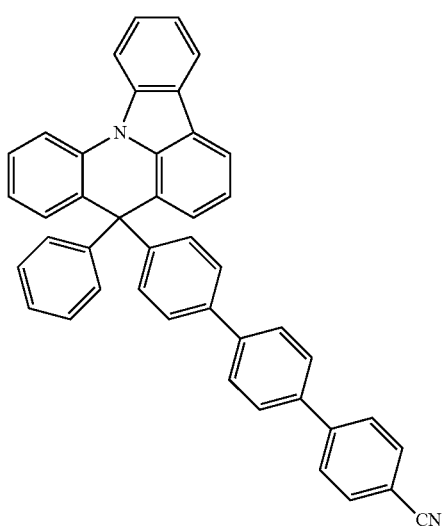
[Compound 93]
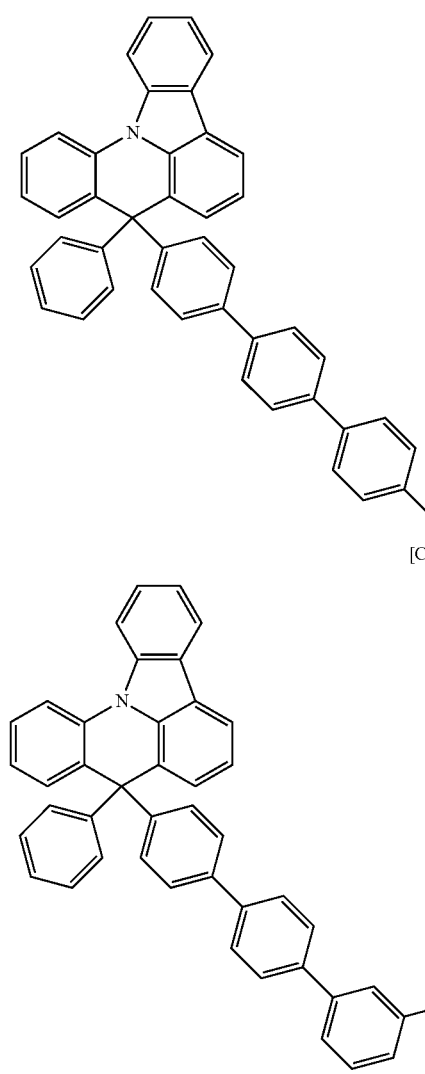
[Compound 94]
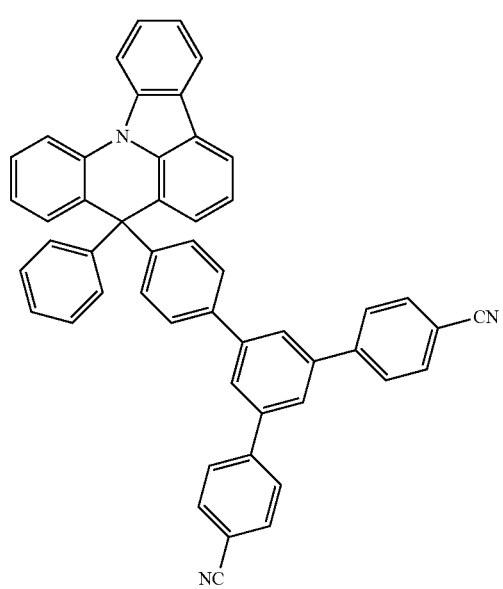

[Compound 95]
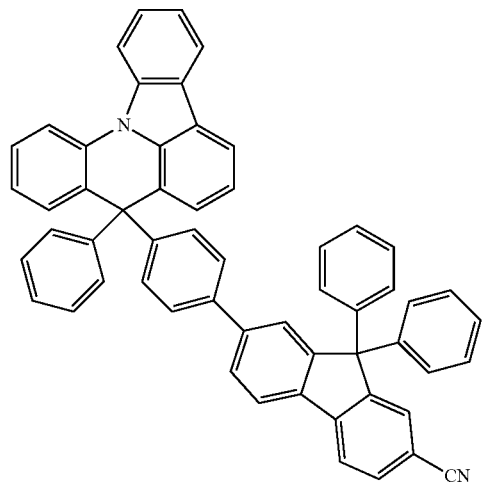
[Compound 98]
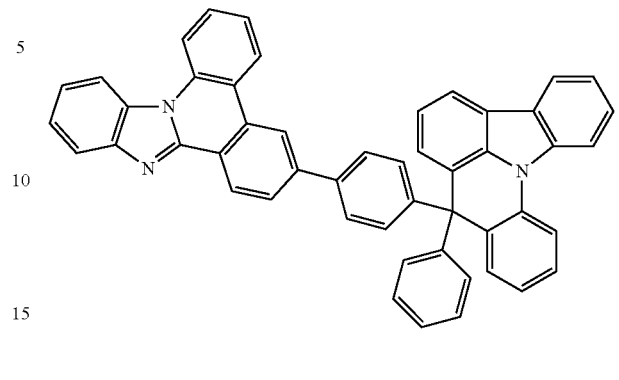
[Compound 96]
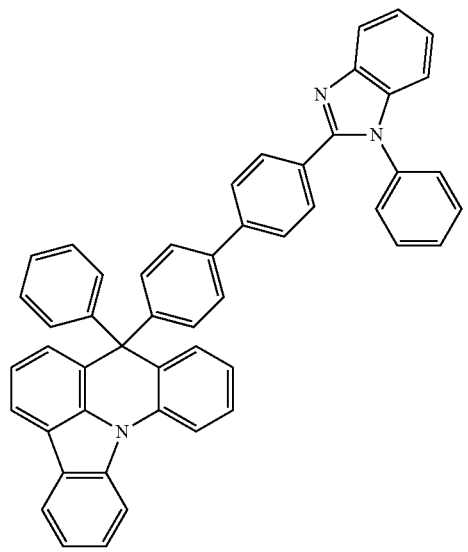
[Compound 99]
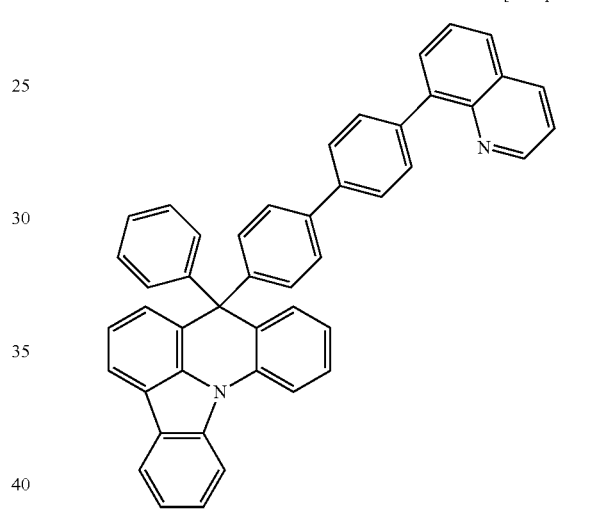
[Compound 97]
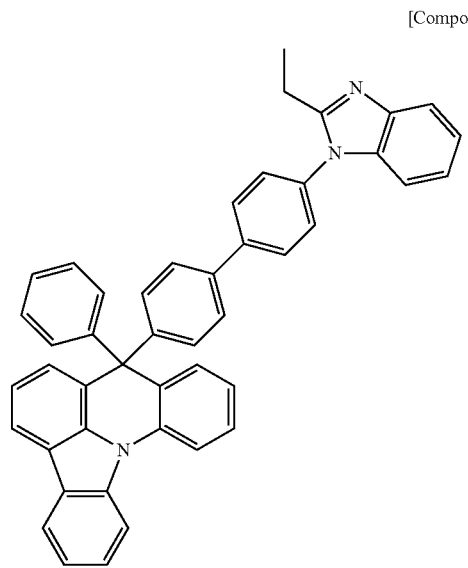
[Compound 100]
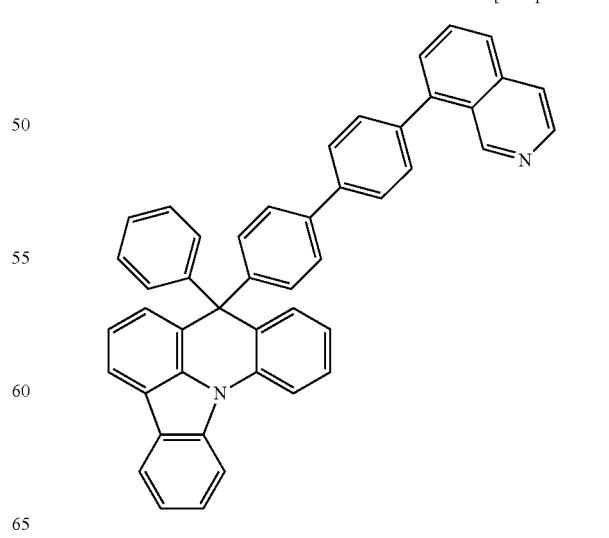

[Compound 101]
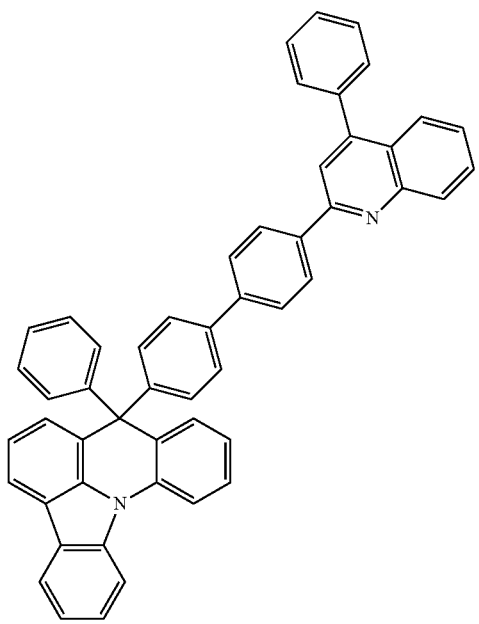
[Compound 102]
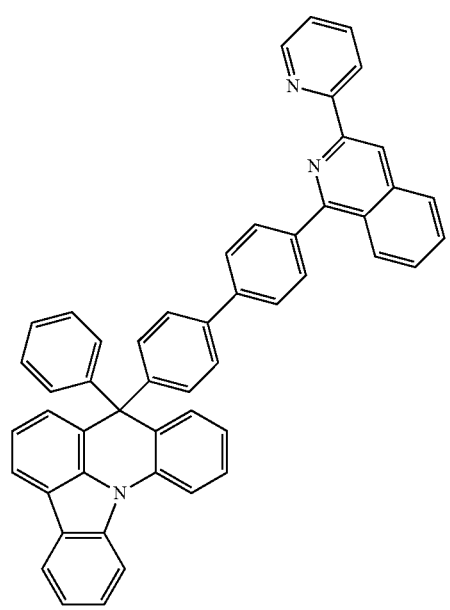
[Compound 103]
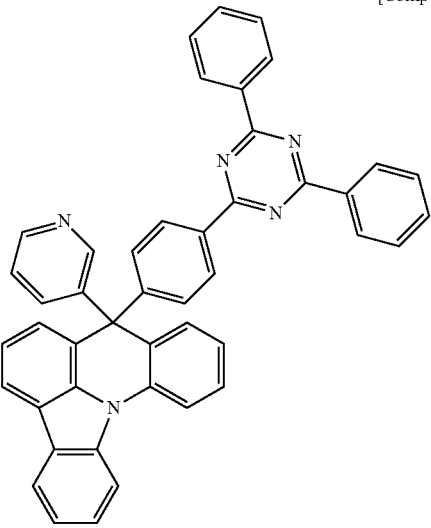
[Compound 104]
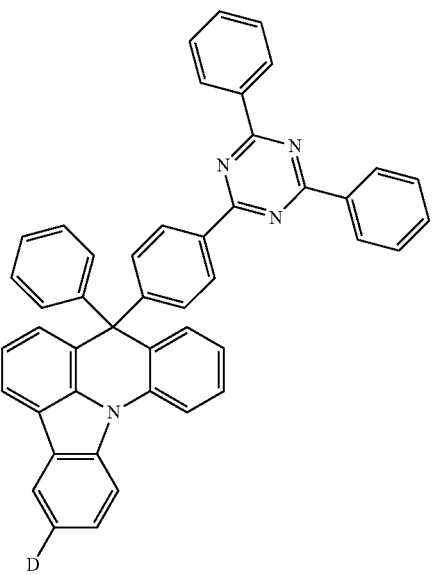

-continued
[Compound 105]
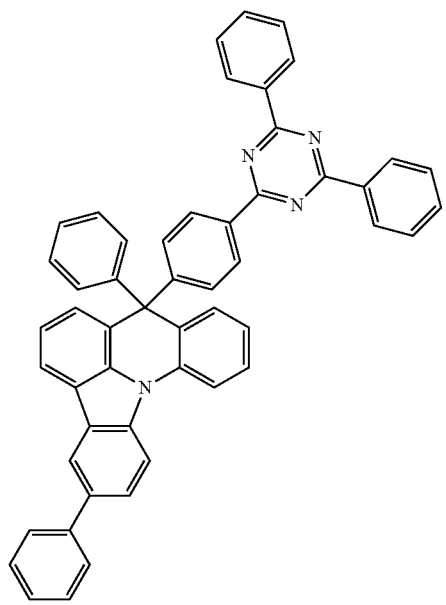
[Compound 107]
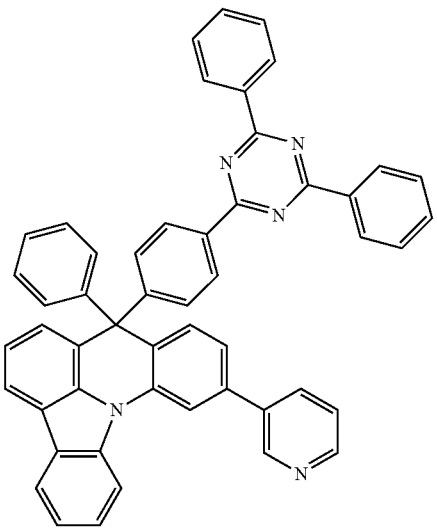
[Compound 106]
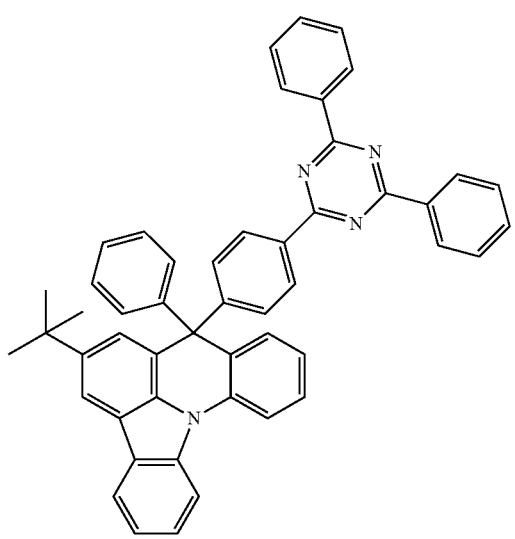
[Compoundn 108]
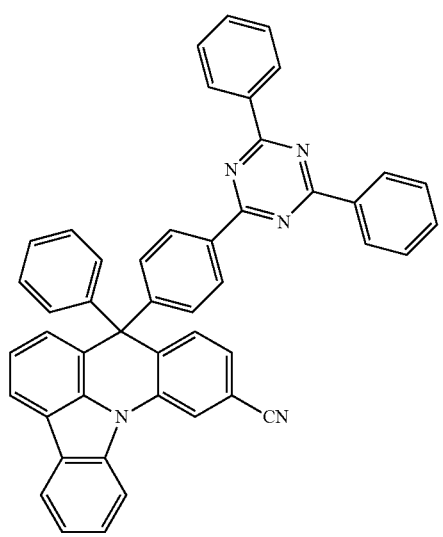

[Compound 109]
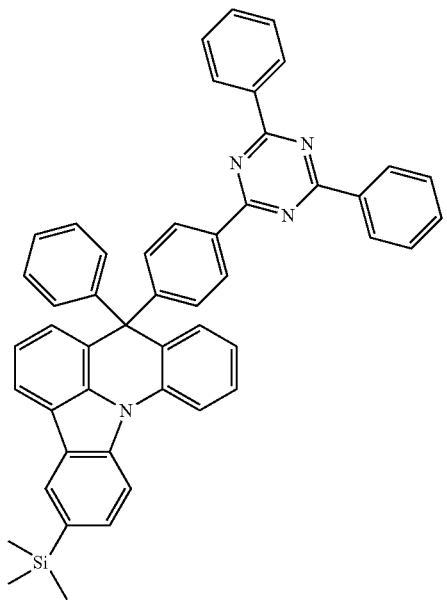
[Compound 110]
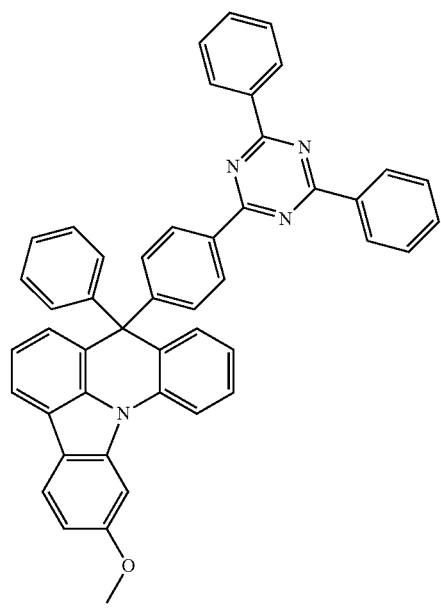
[Compound 111]
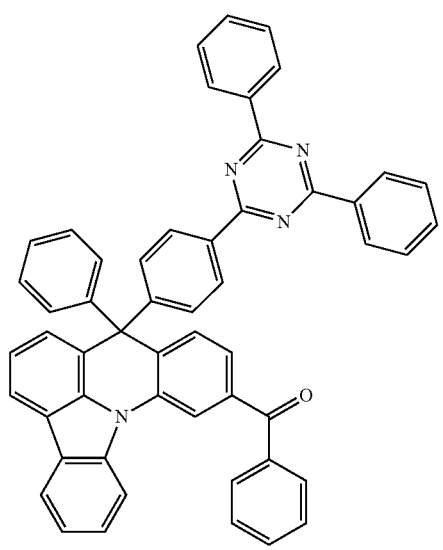
[Compound 112]
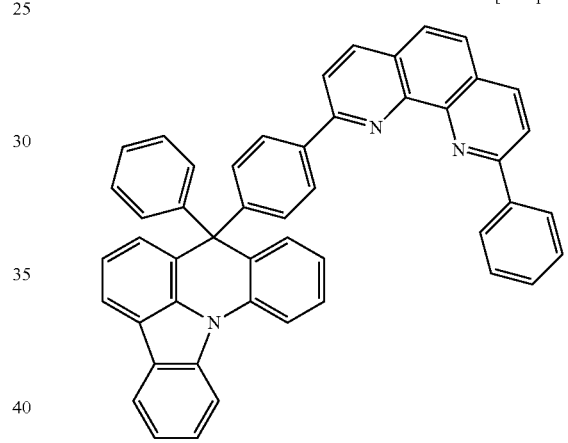
[Compound 113]
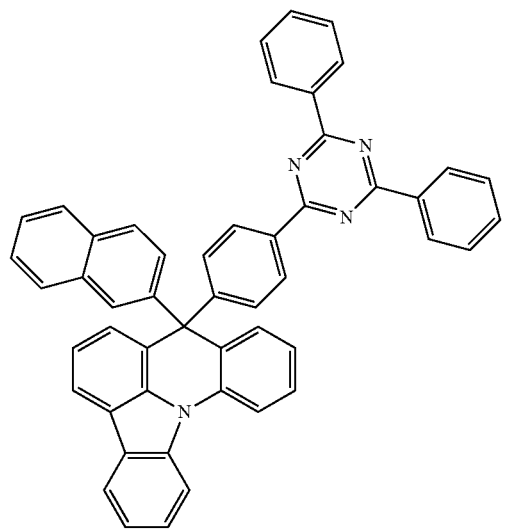

[Compound 114]
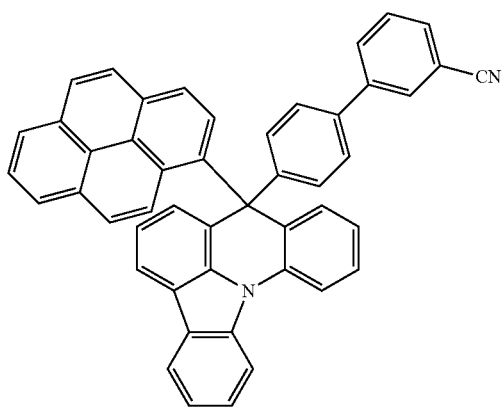
[Compound 115]
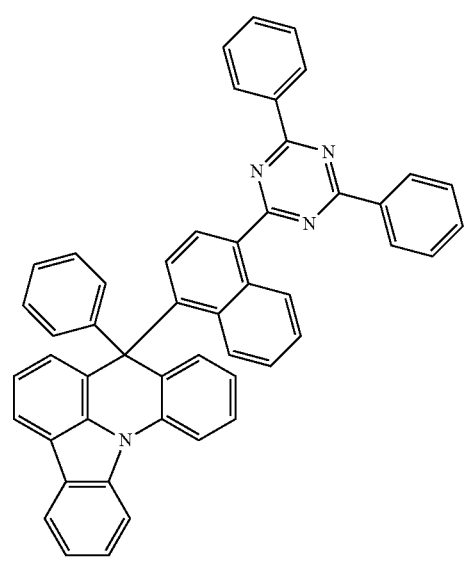
[Compound 116]
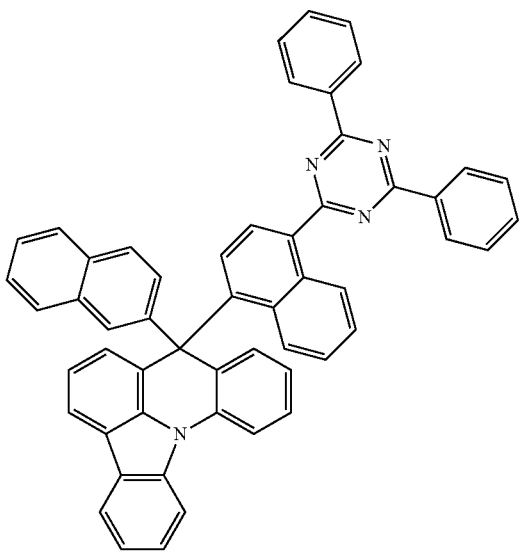
[Compound 117]
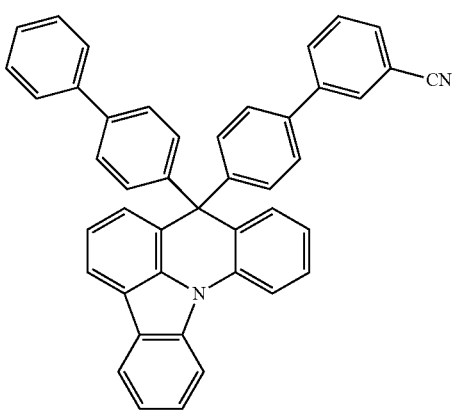
The compound according to an exemplary embodiment of the present application may be prepared by a preparation method to be described below.
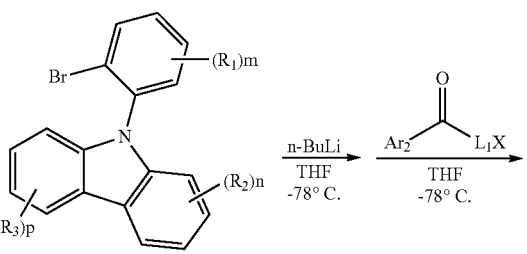
[Chemical Formula A-1]
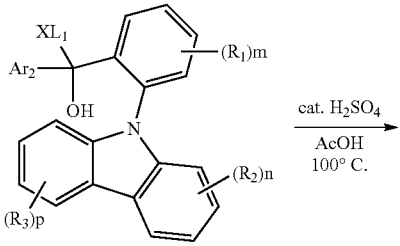
[Chemical Formula A-2]
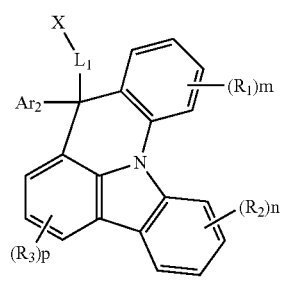
[Chemical Formula A-3]

-continued

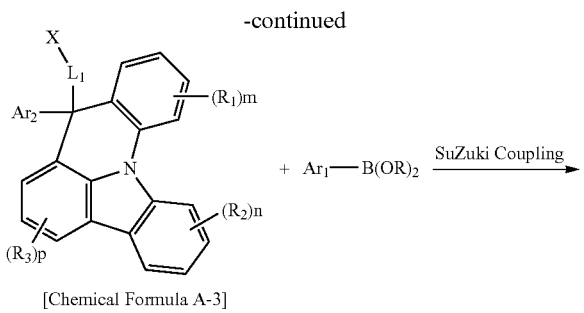

[Chemical Formula A-3]

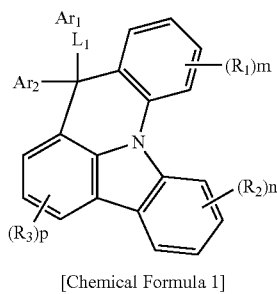

[Chemical Formula 1]

First, Chemical Formula A-1 is lithiated through a low-temperature reaction, and then a carbonyl compound is added dropwise thereto to prepare a compound of Chemical Formula A-2. Chemical Formula A-3 is prepared through a cyclization reaction under an acid catalyst condition. Chemical Formula 1 may be prepared by a Suzuki coupling reaction of the prepared Chemical Formula A-3 and a boron compound.

Further, the present specification provides an organic light emitting device including the above-described compound.

An exemplary embodiment of the present application provides an organic light emitting device including: a first electrode; a second electrode provided to face the first electrode; and one or more organic material layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic light emitting device of the present application may also be composed of a single-layered structure, but may be composed of a multi-layered structure in which two or more organic material layers are stacked. For example, as a representative example of the organic light emitting device of the present invention, an organic light emitting device may have a structure including a hole injection layer, a hole transport layer, a light emitting layer, an electron transport layer, an electron injection layer, and the like as organic material layers. However, the structure of the organic light emitting device is not limited thereto, and may include a fewer number of organic material layers.

In an exemplary embodiment of the present application, the organic material layer includes a light emitting layer, and the light emitting layer includes the compound.

In an exemplary embodiment of the present application, the organic material layer includes a hole injection layer or a hole transport layer, and the hole injection layer or the hole transport layer includes the compound.

In another exemplary embodiment, the organic material layer includes a light emitting layer, and the light emitting layer includes the compound.

In an exemplary embodiment of the present application, the organic material layer includes an electron transport layer or an electron injection layer, and the electron transport layer or the electron injection layer includes the compound.

In an exemplary embodiment of the present application, the organic material layer includes an electron blocking layer or a hole blocking layer, and the electron blocking layer or the hole blocking layer includes the compound.

In an exemplary embodiment of the present application, the organic light emitting device includes: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the compound.

In an exemplary embodiment of the present application, as the two or more organic material layers, two or more may be selected from the group consisting of an electron transport layer, an electron injection layer, a layer which transports and injects electrons simultaneously, and a hole blocking layer.

In an exemplary embodiment of the present application, the organic material layer includes two or more electron transport layers, and at least one of the two or more electron transport layers includes the compound. Specifically, in an exemplary embodiment of the present specification, the compound may also be included in one layer of the two or more electron transport layers, and may be included in each of the two or more electron transport layers.

In addition, in an exemplary embodiment of the present application, when the compound is included in each of the two or more electron transport layers, the other materials except for the compound may be the same as or different from each other.

In an exemplary embodiment of the present application, the organic material layer further includes a hole injection layer or a hole transport layer, which includes a compound including an arylamino group, a carbazole group, or a benzocarbazole group, in addition to the organic material layer including the compound.

In another exemplary embodiment, the organic light emitting device may be an organic light emitting device having a normal type structure in which a positive electrode, one or more organic material layers, and a negative electrode are sequentially stacked on a substrate.

In still another exemplary embodiment, the organic light emitting device may be an organic light emitting device having an inverted type structure in which a negative electrode, one or more organic material layers, and a positive electrode are sequentially stacked on a substrate.

For example, the structure of the organic light emitting device according to an exemplary embodiment of the present application is exemplified in FIGS. 1 and 2.

FIG. 1 exemplifies a structure of an organic light emitting device in which a substrate 1, a positive electrode 2, a light emitting layer 3, and a negative electrode 4 are sequentially stacked. In the structure as described above, the compound may be included in the light emitting layer 3.

FIG. 2 exemplifies a structure of an organic light emitting device in which a substrate 1, a positive electrode 2, a hole injection layer 5, a hole transport layer 6, a light emitting layer 3, an electron transport layer 7, and a negative electrode 4 are sequentially stacked. In the structure as described above, the compound may be included in one or more layers of the hole injection layer 5, the hole transport layer 6, the light emitting layer 3, and the electron transport layer 7.

In the structure as described above, the compound may be included in one or more layers of the hole injection layer, the hole transport layer, the light emitting layer, and the electron transport layer.

The organic light emitting device of the present application may be manufactured by the materials and methods known in the art, except that one or more layers of the organic material layers include the compound of the present application, that is, the compound.

When the organic light emitting device includes a plurality of organic material layers, the organic material layers may be formed of the same material or different materials.

The organic light emitting device of the present application may be manufactured by the materials and methods known in the art, except that one or more layers of the organic material layers include the compound, that is, the compound represented by Chemical Formula 1.

For example, the organic light emitting device of the present application may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto. In an exemplary embodiment of the present application, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto. The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

The electron transport layer is a layer which receives electrons from an electron injection layer and transports the electrons to a light emitting layer, and an electron transport material is a material which may receive electrons well from a negative electrode and transfer the electrons to a light emitting layer, and is suitably a material having a large mobility for electrons. Specific examples thereof include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a positive electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

MODE FOR INVENTION

Hereinafter, the present specification will be described in detail with reference to Examples in order to specifically explain the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

Preparation Examples

<Preparation Example 1> Preparation of [Compound 1]

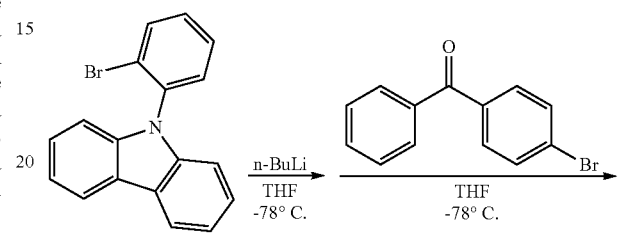

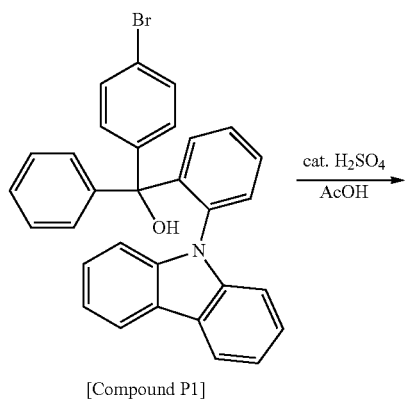

[Compound P1]

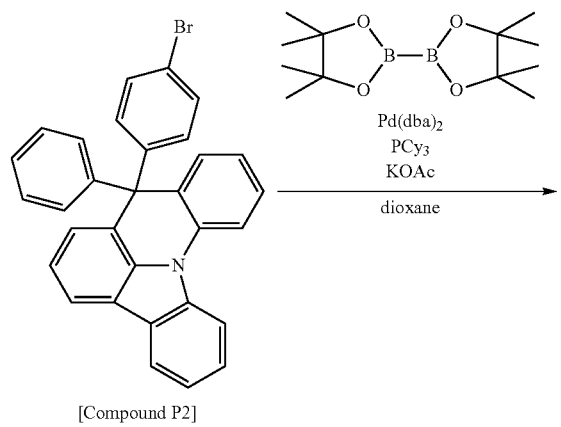

[Compound P2]

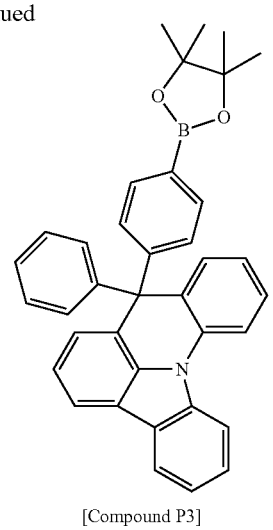

[Compound P3]

9-(2-bromophenyl)-9H-carbazole (30 g, 93 mmol) was dissolved in 300 ml of an anhydrous tetrahydrofuran (THF) solution, and then the resulting solution was stirred at −78° C. under nitrogen atmosphere. 2.5 M of n-BuLi (37 mL, 93 mmol) was slowly added dropwise to the reaction solution. After 1 hour, (4-bromophenyl) (phenyl)methanone (24 g, 93 mmol) was dissolved in 100 mL of anhydrous THF, and the resulting solution was slowly added dropwise thereto. After 1 hour, the reaction solution was warmed to normal temperature, and then 200 mL of water was added thereto, and the resulting mixture was stirred. The THF layer was distilled to prepare [Compound P1] (40.3 g, yield 86%, MS: [M+H]$^+$=505).

[Compound P1] (40.3 g, 80 mmol) and 0.1 mL of sulfuric acid were put into 500 mL of acetic acid, and then the resulting mixture was stirred and refluxed for 2 hours. After the mixture was cooled to normal temperature, a solid produced was filtered and washed with water, and then dried, thereby preparing [Compound P2] (34 g, yield 88%, MS: [M+H]$^+$=487).

[Compound P2] (15 g, 31 mmol), bis(pinacolato) diboron (8.7 g, 34 mmol), and KOAc (9.1 g, 93 mmol) were put into 200 mL of dioxane, and then the resulting mixture was stirred and refluxed. Pd(dba)$_2$ (0.5 g, 0.93 mmol) and PCy3 (0.5 g, 1.8 mmol) were put thereinto, and then the resulting mixture was stirred and refluxed for 3 hours. The mixture was cooled to normal temperature, and then the reaction solution was filtered and distilled. The distilled sample was dissolved in CHCl$_3$ to perform a work-up. The organic material layer was recrystallized with ethanol to prepare [Compound P3] (13.7 g, 83%, MS: [M+H]$^+$=534).

[Compound P3] (10 g, 19 mmol) and 2-chloro-4,6-diphenyl-1,3,5-triazine (5.1 g, 19 mmol) were put into 150 mL of THF. 75 mL of 2 M K$_2$CO$_3$ and 0.4 g of Pd(PPh$_3$)$_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 1] (9.5 g, yield 78%, MS: [M+H]$^+$=639).

<Preparation Example 2> Preparation of [Compound 2]

[Compound P3] (10 g, 19 mmol) and 2-([1,1'-biphenyl]-4-yl)-4-chloro-6-phenyl-1,3,5-triazine (6.5 g, 19 mmol) were put into 150 mL of THF. 75 mL of 2 M K$_2$CO$_3$ and 0.4 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 2] (9.9 g, yield 73%, MS: [M+H]$^+$=715).

<Preparation Example 3> Preparation of [Compound 9]

[Compound P3] (10 g, 19 mmol) and 2-(3-bromophenyl)-4,6-diphenyl-1,3,5-triazine (7.4 g, 19 mmol) were put into 150 mL of THF. 75 mL of 2 M K$_2$CO$_3$ and 0.4 g of Pd(PPh$_3$)$_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 9] (9.5 g, yield 70%, MS: [M+H]$^+$=715).

<Preparation Example 4> Preparation of [Compound 14]

[Compound P3] (10 g, 19 mmol) and 2-chloro-4,6-di(naphthalen-1-yl)-1,3,5-triazine (7.0 g, 19 mmol) were put into 150 mL of THF. 75 mL of 2 M K$_2$CO$_3$ and 0.4 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 14] (10.5 g, yield 75%, MS: [M+H]$^+$=739).

<Preparation Example 5> Preparation of [Compound 22]

[Compound P4] was prepared in the same manner as in the preparation method of Compound P3 in <Preparation Example 1>, except that (3-bromophenyl) (phenyl)methanone was used instead of (4-bromophenyl) (phenyl)methanone. (MS: [M+H]$^+$=534)

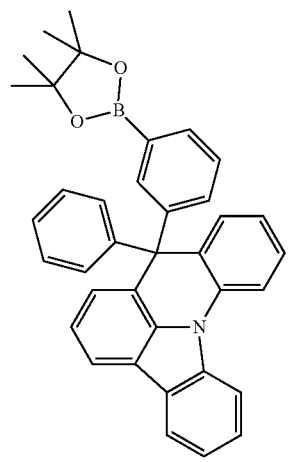

[Compound P4]

[Compound P4] (10 g, 19 mmol) and 2-([1,1'-biphenyl]-3-yl)-4-chloro-6-phenyl-1,3,5-triazine (6.5 g, 19 mmol) were put into 150 mL of THF. 75 mL of 2 M K$_2$CO$_3$ and 0.4 g of Pd(PPh$_3$)$_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 22] (9.2 g, yield 68%, MS: $[M+H]^+=715$).

<Preparation Example 6> Preparation of [Compound 29]

[Compound P3] (10 g, 19 mmol) and 4-([1,1'-biphenyl]-4-yl)-6-chloro-2-phenylpyrimidine (6.5 g, 19 mmol) were put into 150 mL of THF. 75 mL of 2 M $K_2CO_3$ and 0.4 g of $Pd(PPh_3)_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 29] (9.5 g, yield 70%, MS: $[M+H]^+=714$).

<Preparation Example 7> Preparation of [Compound 33]

[Compound P3] (10 g, 19 mmol) and 4-chloro-2-phenyl-6-(4-(pyridin-2-yl)phenyl)pyrimidine (6.5 g, 19 mmol) were put into 150 mL of THF. 75 mL of 2 M $K_2CO_3$ and 0.4 g of $Pd(PPh_3)_4$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 33] (8.6 g, yield 63%, MS: $[M+H]^+=715$).

<Preparation Example 8> Preparation of [Compound 54]

[Compound P3] (10 g, 19 mmol) and 2-(4-bromophenyl)-4,6-diphenylpyrimidine (7.4 g, 19 mmol) were put into 150 mL of THF. 75 mL of 2 M $K_2CO_3$ and 0.4 g of $Pd(PPh_3)_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 54] (8.1 g, yield 60%, MS: $[M+H]^+=714$).

<Preparation Example 9> Preparation of [Compound 66]

[Compound P3] (10 g, 19 mmol) and 4'-bromo-2,2':6',2''-terpyridine (5.9 g, 19 mmol) were put into 150 mL of THF. 75 mL of 2 M $K_2CO_3$ and 0.4 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 66] (9.7 g, yield 80%, MS: $[M+H]^+=639$).

<Preparation Example 10> Preparation of [Compound 78]

[Compound P3] (10 g, 19 mmol) and 4-(4-bromophenyl)dibenzo[b,d]furan (6.1 g, 19 mmol) were put into 150 mL of THF. 75 mL of 2 M $K_2CO_3$ and 0.4 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 78] (9.1 g, yield 74%, MS: $[M+H]^+=650$).

<Preparation Example 11> Preparation of [Compound 88]

[Compound P3] (10 g, 19 mmol) and 2-(4-chlorophenyl)-4-phenylquinazoline (6.0 g, 19 mmol) were put into 150 mL of THF. 75 mL of 2 M $K_3PO_4$ and 0.2 g of $Pd(PtBu_3)_2$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 88] (9.2 g, yield 70%, MS: $[M+H]^+=688$).

<Preparation Example 12> Preparation of [Compound 92]

[Compound P3] (10 g, 19 mmol) and 4'-chloro-[1,1'-biphenyl]-4-carbonitrile (4.1 g, 19 mmol) were put into 150 mL of THF. 75 mL of 2 M $K_3PO_4$ and 0.2 g of $Pd(PtBu_3)_2$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 92] (8.9 g, yield 80%, MS: $[M+H]^+=585$).

<Preparation Example 13> Preparation of [Compound 96]

[Compound P3] (10 g, 19 mmol) and 2-(4-chlorophenyl)-1-phenyl-1H-benzo[d]imidazole (5.8 g, 19 mmol) were put into 150 mL of THF. 75 mL of 2 M $K_3PO_4$ and 0.2 g of $Pd(PtBu_3)_2$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 96] (8.2 g, yield 64%, MS: $[M+H]^+=676$).

<Preparation Example 14> Preparation of [Compound 103]

[Compound P5] was prepared in the same manner as in the preparation method of Compound P3 in <Preparation Example 1>, except that (4-bromophenyl) (pyridin-3-yl)methanone was used instead of (4-bromophenyl) (phenyl)methanone. (MS: $[M+H]^+=535$)

[Compound P5]

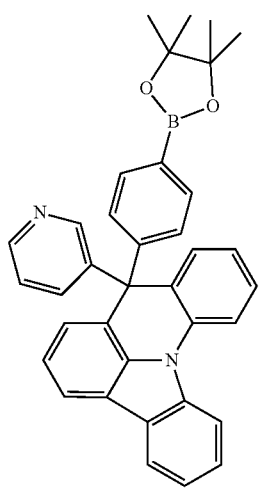

[Compound P6]

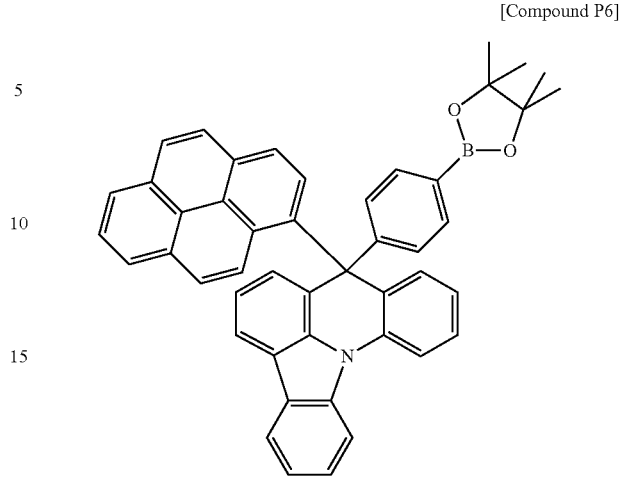

[Compound P5] (10 g, 19 mmol) and 2-chloro-4,6-diphenyl-1,3,5-triazine (5.8 g, 19 mmol) were put into 150 mL of THF. 75 mL of 2 M $K_3PO_4$ and 0.2 g of $Pd(PtBu_3)_2$ were put thereinto, and then the resulting mixture was stirred and refluxed for 10 hours. The mixture was cooled to normal temperature, and then a solid produced by filtering the mixture was recrystallized with chloroform and ethanol, thereby preparing [Compound 103] (8.2 g, yield 64%, MS: [M+H]$^+$=676).

<Preparation Example 15> Preparation of [Compound 112]

[Compound P3] (10 g, 19 mmol) and 2-chloro-9-phenyl-1,10-phenanthroline (5.5 g, 19 mmol) were put into 150 mL of THF. 75 mL of 2 M $K_2CO_3$ and 0.4 g of $Pd(PPh_3)_4$ were put thereinto, and the resulting mixture was stirred and refluxed for 7 hours. The mixture was cooled to room temperature, and then a solid produced by filtrating the mixture was recrystallized with chloroform and ethanol, thereby preparing [Compound 112] (8.6 g, yield 68%, MS: [M+H]+=662).

<Preparation Example 16> Preparation of [Compound 114]

[Compound P6] was prepared in the same manner as in the preparation method of Compound P3 in <Preparation Example 1>, except that (4-bromophenyl) (pyren-1-yl) methanone was used instead of (4-bromophenyl) (phenyl) methanone. (MS: [M+H]$^+$=658)

[Compound P6] (12.5 g, 19 mmol) and 3-bromobenzonitrile (3.5 g, 19 mmol) were put into 150 mL of THF. 75 mL of 2 M $K_2CO_3$ and 0.4 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 114] (9.1 g, yield 76%, MS: [M+H]$^+$=633).

EXAMPLES

Example 1-1

A glass substrate thinly coated with indium tin oxide (ITO) to have a thickness of 1,300 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

The following Compound [HI-A] was thermally vacuum deposited to have a thickness of 600 Å on the transparent ITO electrode, which was prepared as described above, thereby forming a hole injection layer. The following Compound [HAT-CN] (50 Å) and the following Compound [HT-A](600 Å) were sequentially vacuum deposited on the hole injection layer, thereby forming a hole transport layer. Subsequently, the following Compounds [BH] and [BD] were vacuum deposited at a weight ratio of 25:1 to have a film thickness of 200 Å on the hole transporting layer, thereby forming a light emitting layer.

[Compound 1] and the LiQ compound were deposited at a weight ratio of 1:1 to have a thickness of 350 Å on the light emitting layer, thereby forming an electron injection and transport layer. Lithium fluoride (LiF) and aluminum were sequentially deposited to have a thickness of 10 Å and 1,000 Å, respectively, on the electron injection and transport layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec, and at 2 Å/sec, respectively, and the degree of vacuum during the deposition was maintained at 1×10$^{-7}$ to 5×10$^{-8}$ torr, thereby manufacturing an organic light emitting device.

[HI-A]
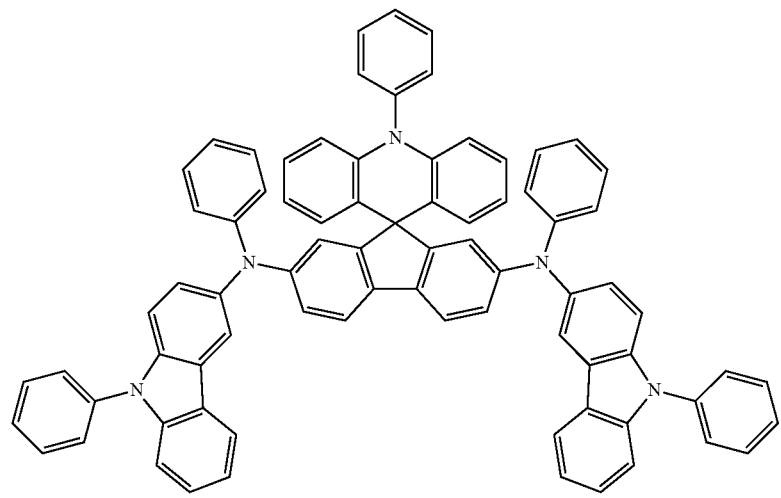
[HAT-CN]
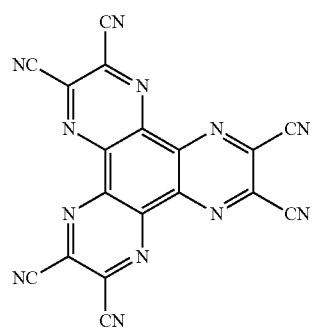
[HT-A]
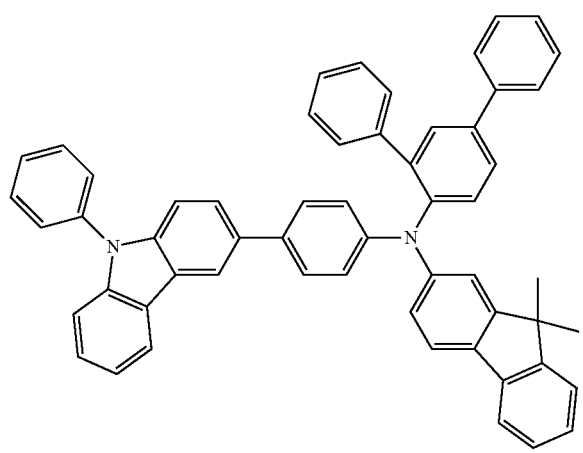
[BH]
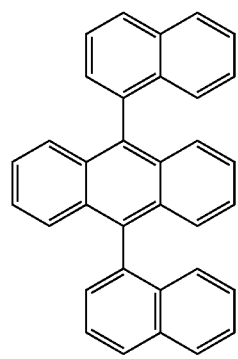
[LiQ]
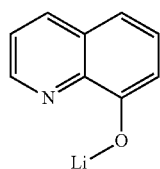

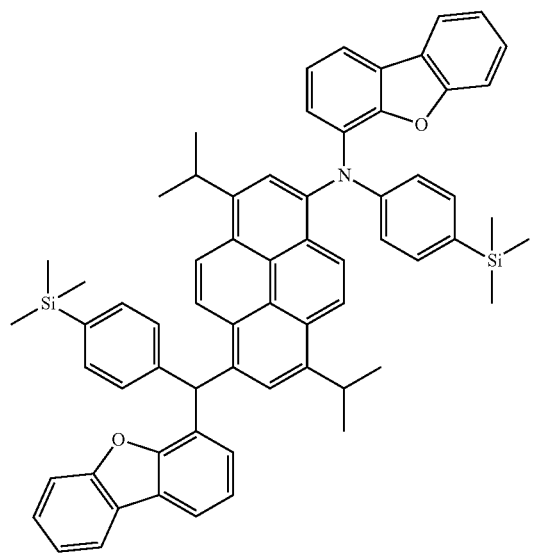
[BD]

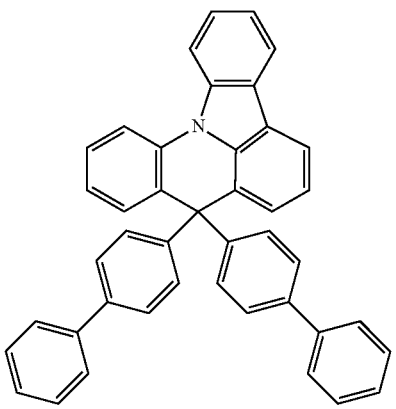
{ET-A}

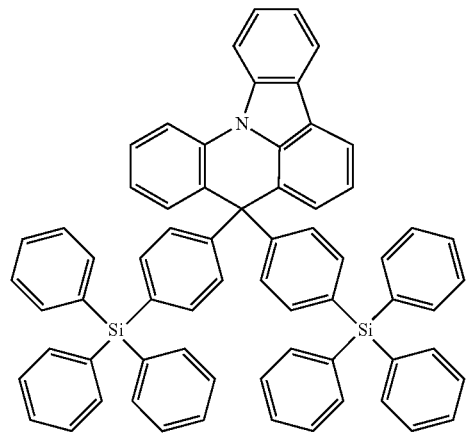
[ET-B]

Example 1-2

An organic light emitting device was manufactured in the same manner as in <Example 1-1>, except that [Compound 2] was used instead of [Compound 1] of <Example 1-1>.

Example 1-3

An organic light emitting device was manufactured in the same manner as in <Example 1-1>, except that [Compound 9] was used instead of [Compound 1] of <Example 1-1>.

Example 1-4

An organic light emitting device was manufactured in the same manner as in <Example 1-1>, except that [Compound 14] was used instead of [Compound 1] of <Example 1-1>.

Example 1-5

An organic light emitting device was manufactured in the same manner as in <Example 1-1>, except that [Compound 22] was used instead of [Compound 1] of <Example 1-1>.

Example 1-6

An organic light emitting device was manufactured in the same manner as in <Example 1-1>, except that [Compound 29] was used instead of [Compound 1] of <Example 1-1>.

Example 1-7

An organic light emitting device was manufactured in the same manner as in <Example 1-1>, except that [Compound 33] was used instead of [Compound 1] of <Example 1-1>.

Example 1-8

An organic light emitting device was manufactured in the same manner as in <Example 1-1>, except that [Compound 54] was used instead of [Compound 1] of <Example 1-1>.

Example 1-9

An organic light emitting device was manufactured in the same manner as in <Example 1-1>, except that [Compound 66] was used instead of [Compound 1] of <Example 1-1>.

Example 1-10

An organic light emitting device was manufactured in the same manner as in <Example 1-1>, except that [Compound 88] was used instead of [Compound 1] of <Example 1-1>.

Example 1-11

An organic light emitting device was manufactured in the same manner as in <Example 1-1>, except that [Compound 103] was used instead of [Compound 1] of <Example 1-1>.

Comparative Example 1-1

An organic light emitting device was manufactured in the same manner as in <Example 1-1>, except that [ET-A] was used instead of [Compound 1] of <Example 1-1>.

Comparative Example 1-2

An organic light emitting device was manufactured in the same manner as in <Example 1-1>, except that [ET-B] was used instead of [Compound 1] of <Example 1-1>.

Example 2-1

An organic light emitting device was manufactured in the same manner as in <Example 1-1>, except that [Compound 92] was used alone instead of a mixture of [Compound 1] and the LiQ compound of <Example 1-1>.

Example 2-2

An organic light emitting device was manufactured in the same manner as in <Example 2-1>, except that [Compound 96] was used instead of [Compound 92] of <Example 2-1>.

Example 2-3

An organic light emitting device was manufactured in the same manner as in <Example 2-1>, except that [Compound 112] was used instead of [Compound 92] of <Example 2-1>.

Example 2-4

An organic light emitting device was manufactured in the same manner as in <Example 2-1>, except that [Compound 114] was used instead of [Compound 92] of <Example 2-1>.

Comparative Example 2-1

An organic light emitting device was manufactured in the same manner as in <Example 2-1>, except that [ET-B] was used instead of [Compound 92] of <Example 2-1>.

Example 3-1

An organic light emitting device was manufactured in the same manner as in <Example 1-1>, except that [Compound 92] and [Compound 78] were used instead of [Compound 1] and the Liq compound of <Example 1-1>, respectively.

Comparative Example 3-1

An organic light emitting device was manufactured in the same manner as in <Example 3-1>, except that [ET-A] and [ET-B] were used instead of [Compound 92] and [Compound 78] of [Example 3-1], respectively.

For the organic light emitting devices manufactured by the above-described method, the driving voltage and the light emitting efficiency were measured at a current density of 10 mA/cm$^2$, and a time ($T_{90}$) for reaching a 90% value compared to the initial luminance was measured at a current density of 20 mA/cm$^2$. The results are shown in the following Table 1.

TABLE 1

| | Voltage (V) | Efficiency (Cd/A) | Color coordinate (x, y) | Lifetime (h) $T_{90}$ at 20 mA/cm$^2$ |
|---|---|---|---|---|
| Example 1-1 | 4.52 | 5.86 | (0.131, 0.131) | 157 |
| Example 1-2 | 4.61 | 5.58 | (0.131, 0.132) | 183 |
| Example 1-3 | 4.49 | 5.97 | (0.131, 0.130) | 148 |
| Example 1-4 | 4.68 | 5.50 | (0.131, 0.133) | 190 |
| Example 1-5 | 4.55 | 5.83 | (0.131, 0.131) | 166 |
| Example 1-6 | 4.32 | 6.32 | (0.131, 0.130) | 135 |
| Example 1-7 | 4.50 | 5.92 | (0.131, 0.131) | 144 |
| Example 1-8 | 4.63 | 5.61 | (0.131, 0.132) | 176 |
| Example 1-9 | 4.40 | 6.10 | (0.131, 0.130) | 147 |
| Example 1-10 | 4.70 | 5.69. | (0.131, 0.130) | 152 |
| Example 1-11 | 4.58 | 5.91 | (0.131, 0.131) | 149 |
| Comparative Example 1-1 | 5.80 | 3.90 | (0.131, 0.133) | 35 |
| Comparative Example 1-2 | 5.51 | 4.20 | (0.131, 0.133) | 62 |
| Example 2-1 | 4.21 | 6.52 | (0.131, 0.133) | 115 |
| Example 2-2 | 4.30 | 6.43 | (0.131, 0.132) | 132 |
| Example 2-3 | 4.18 | 6.60 | (0.131, 0.133) | 109 |
| Example 2-4 | 4.25 | 6.49 | (0.131, 0.132) | 139 |
| Comparative Example 2-1 | 6.40 | 3.22 | (0.131, 0.135) | 45 |
| Example 3-1 | 4.66 | 5.71 | (0.131, 0.131) | 160 |
| Comparative Example 3-1 | 6.62 | 2.90 | (0.131, 0.133) | 53 |

From the results of Table 1, the compound represented by Chemical Formula 1 according to the present invention may be used for an organic material layer of the organic light emitting device which may inject and transport electrons simultaneously. The organic light emitting device using the same has low driving voltage and high efficiency, and may improve stability of the device by hole stability of the compound.

The invention claimed is:
1. A compound represented by the following Chemical Formula 1:

[Chemical Formula 1]

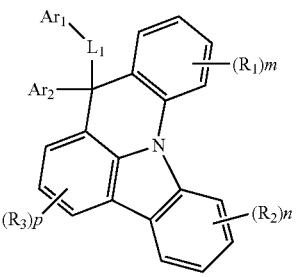

in Chemical Formula 1,
L1 is a substituted or unsubstituted arylene group; or a substituted or unsubstituted divalent heterocyclic group, with the proviso that the divalent heterocyclic group is not a dibenzofuranyl group, Ar₁ is cyano; pyridyl; pyrimidyl; triazinyl; pyridazinyl; quinolinyl; benzimidazolyl; benzimidazolyl fused ring; quinazolinyl; furanyl; thiophenyl; dibenzofuranyl; or dibenzothiophenyl, which is optionally substituted, R₁ to R₃ and Ar₂ are the same as or different from each other, and are each independently hydrogen; deuterium; a halogen group; a cyano group; a nitro group; a hydroxy group; a substituted or unsubstituted carbonyl group; a substituted or unsubstituted ether group; a substituted or unsubstituted ester group; a substituted or unsubstituted amino group; a substituted or unsubstituted alkyl group; a substituted or unsubstituted silyl group; a substituted or unsubstituted phosphoryl group; a substituted or unsubstituted amine group; a substituted or unsubstituted aryl group; or a substituted or unsubstituted heterocyclic group, p is an integer of 0 to 3, m and n are the same as or different from each other, and are each independently an integer of 0 to 4, and when m, n and p are each an integer of 2 or more, a plurality of structures in the parenthesis are the same as or different from each other.

2. The compound of claim 1, wherein Ar₁ is optionally substituted with at least one selected from deuterium; a halogen group; a cyano group; a C₁ to C₁₀ alkyl group; a C₆ to C₁₂ aryl group; or a C₂ to C₁₀ heterocyclic group.

3. The compound of claim 1, wherein L₁ is a substituted or unsubstituted arylene group.

4. The compound of claim 1, wherein Are is hydrogen; an aryl group; or a heterocyclic group.

5. The compound of claim 1, wherein R₁ to R₃ are the same as or different from each other, and are each independently hydrogen; deuterium; a cyano group; a substituted or unsubstituted carbonyl group; a substituted or unsubstituted ether group; a substituted or unsubstituted silyl group; a substituted or unsubstituted alkyl group; a substituted or unsubstituted aryl group; or a substituted or unsubstituted heterocyclic group.

6. A compound represented by any one selected among the following structural formulae:

[Compound 1]

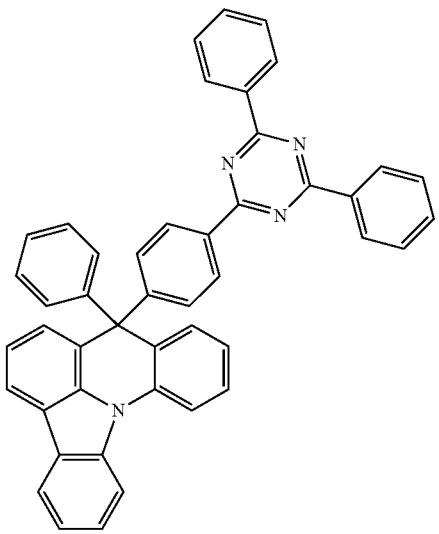

[Compound 2]

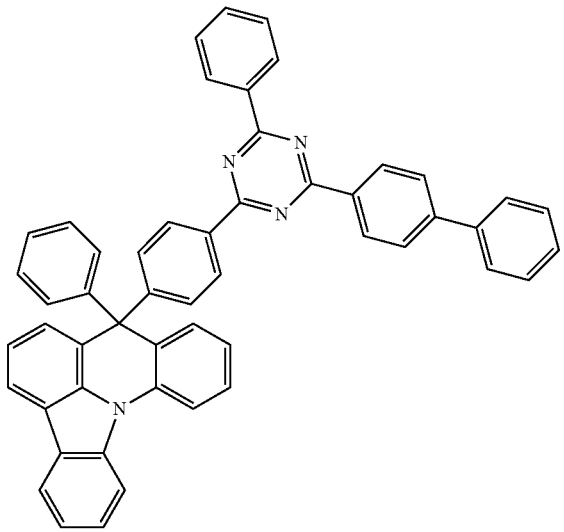

[Compound 3]

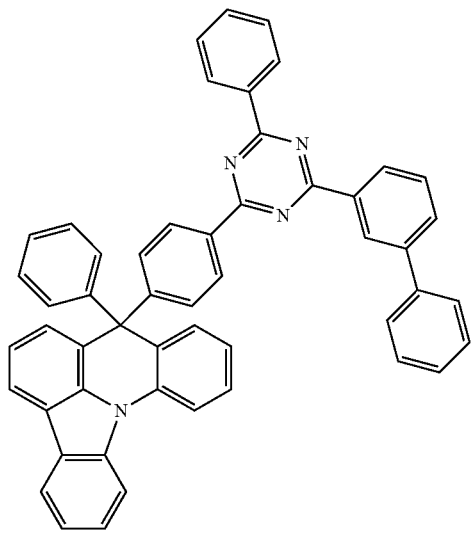

[Compoiund 4]

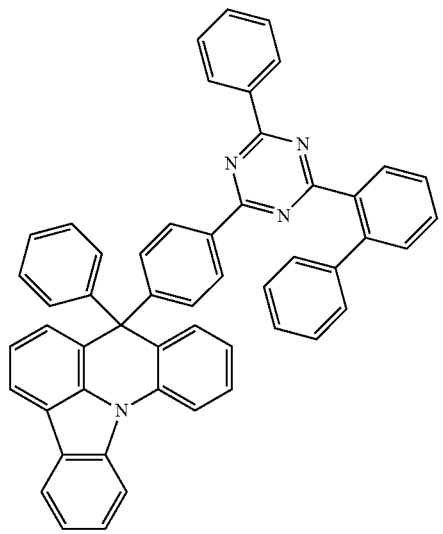

[Compound 5]
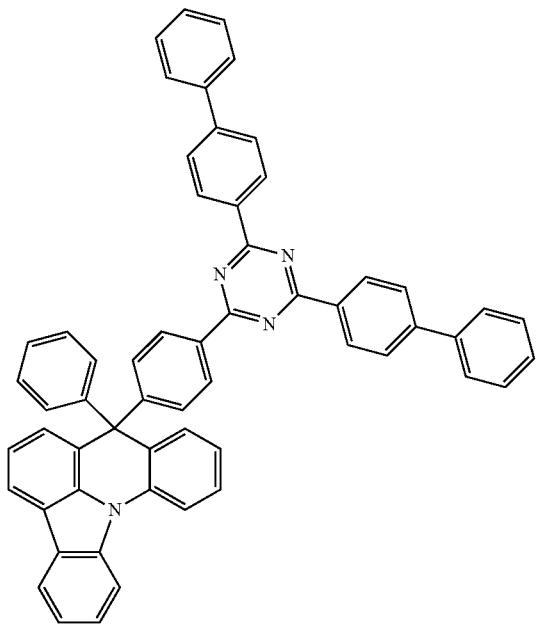
[Compound 6]
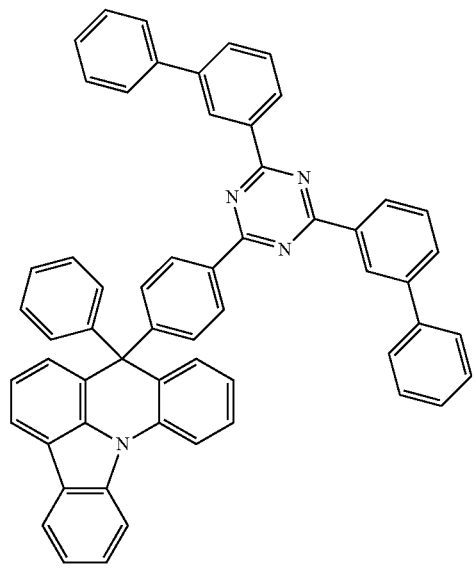
[Compound 7]
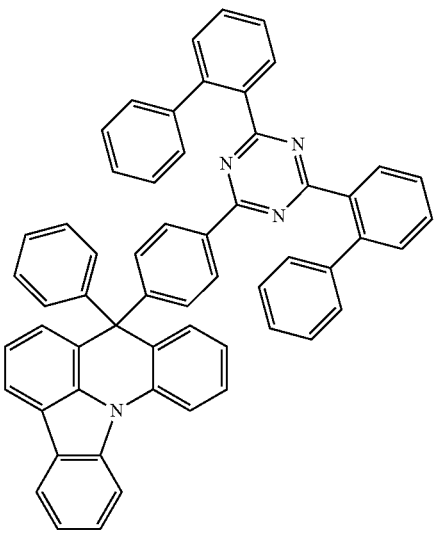
[Compound 8]
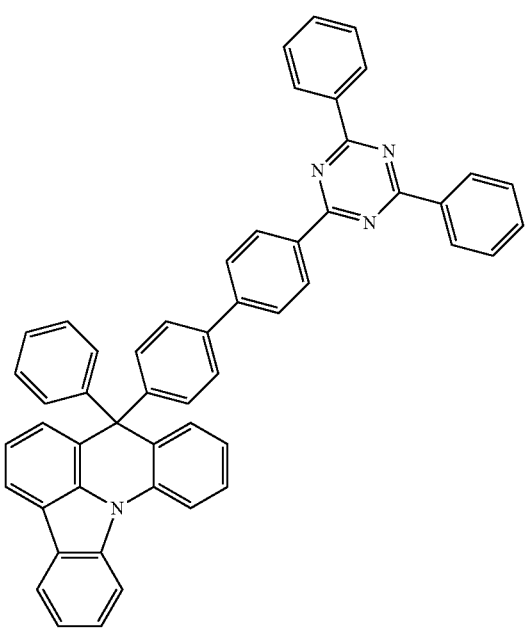

[Compound 9]
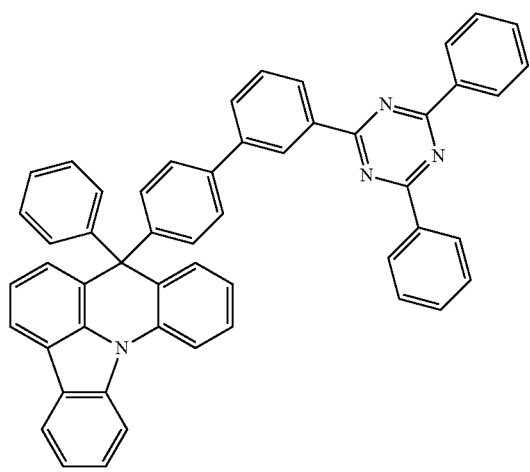
[Compound 10]
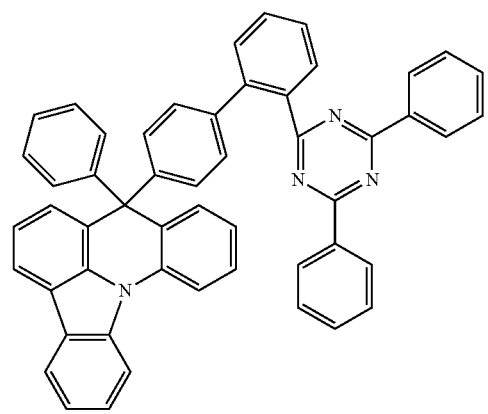
[Compound 11]
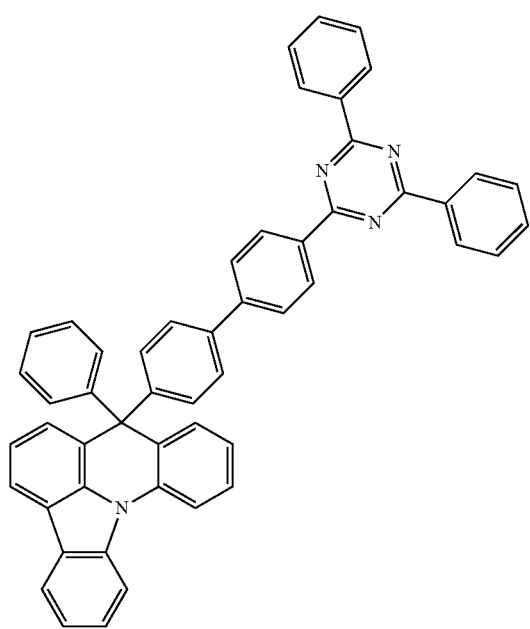
[Compound 12]
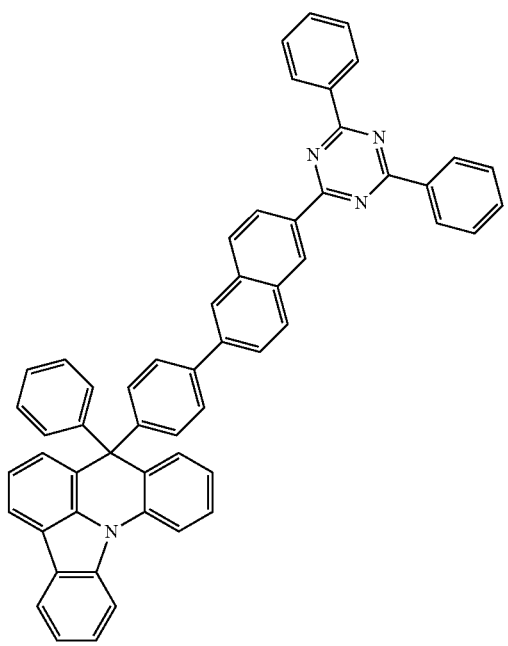
[Compound 13]
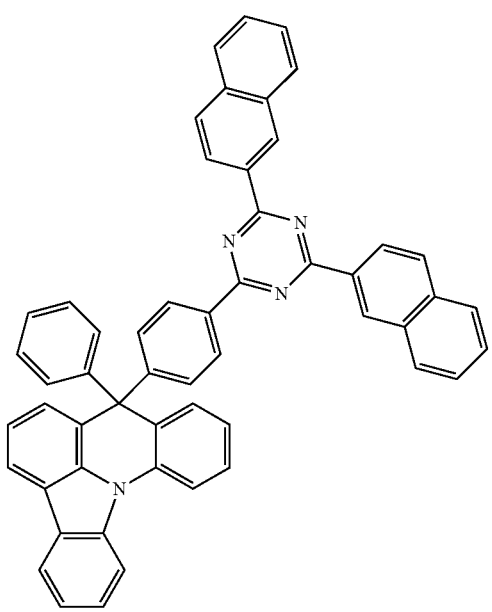

[Compound 14]
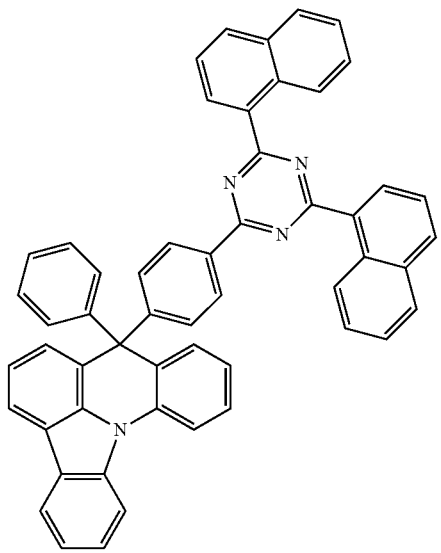
[Compound 15]
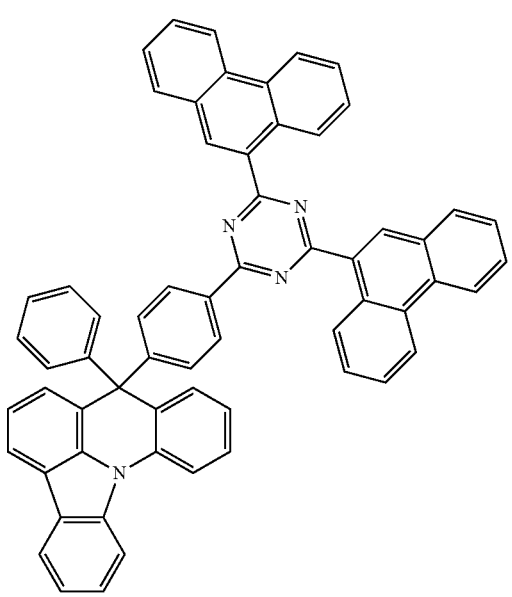
[Compound 16]
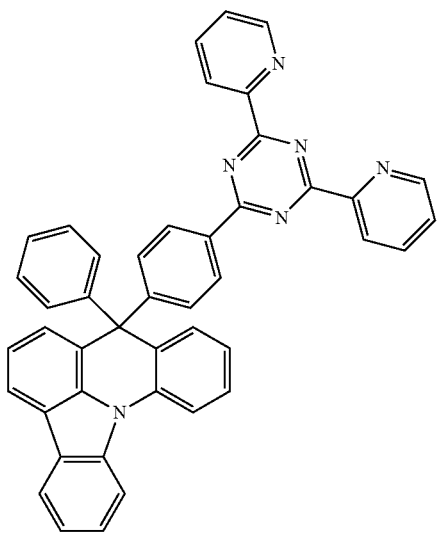
[Compound 17]
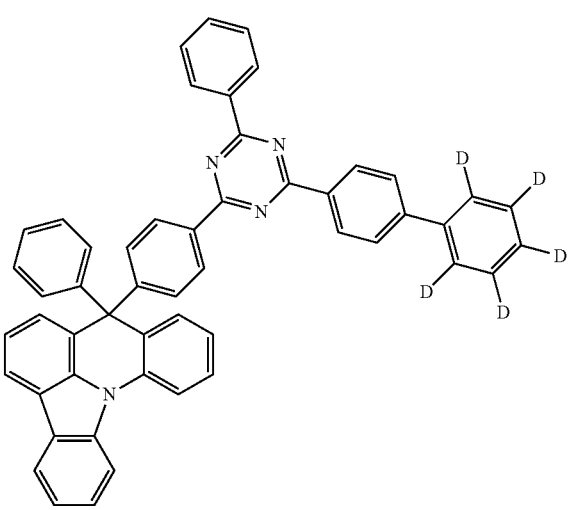
[Compound 18]
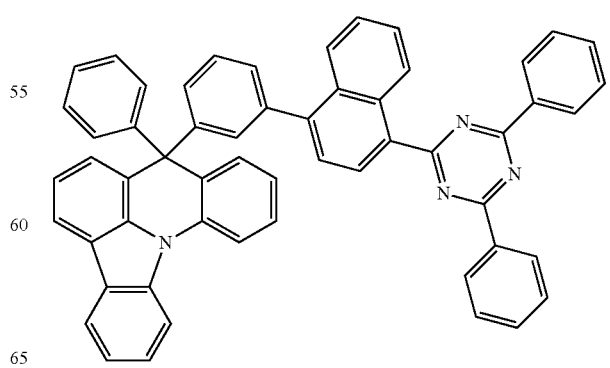

-continued
[Compound 19]
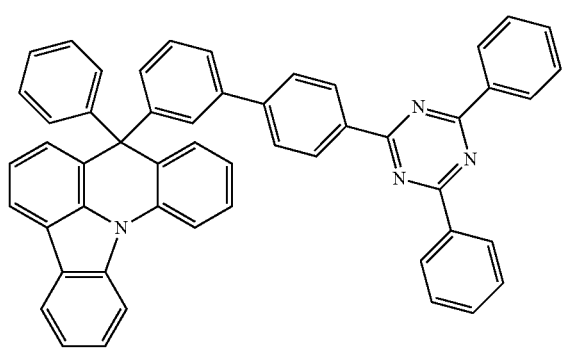
[Compound 20]
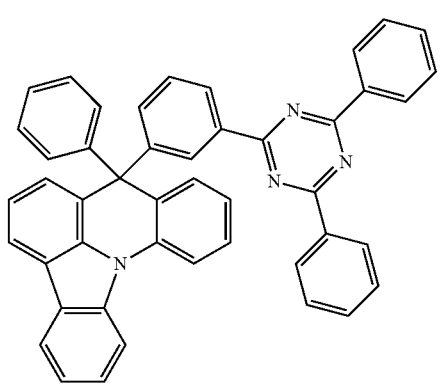
[Compound 21]
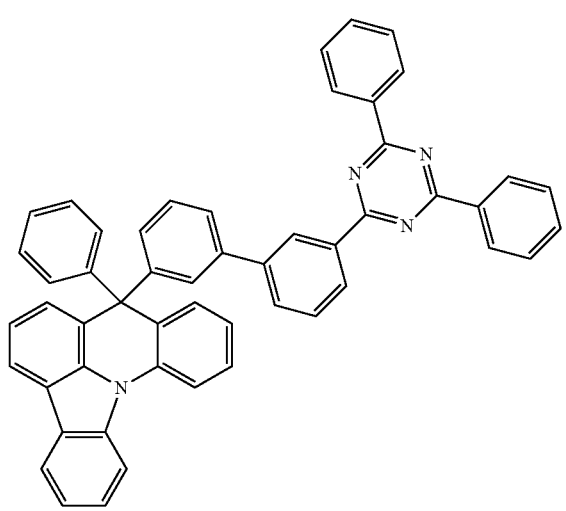
[Compound 22]
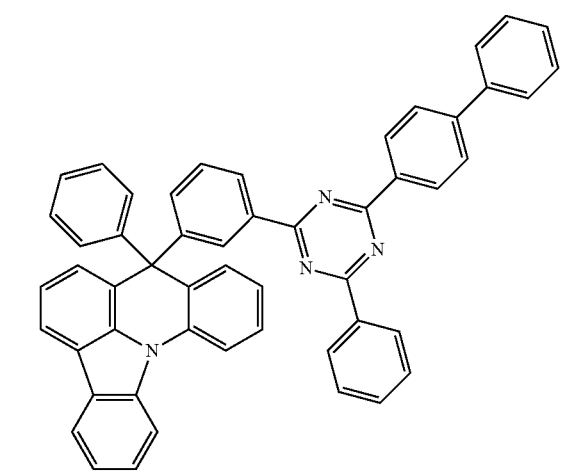
[Compound 23]
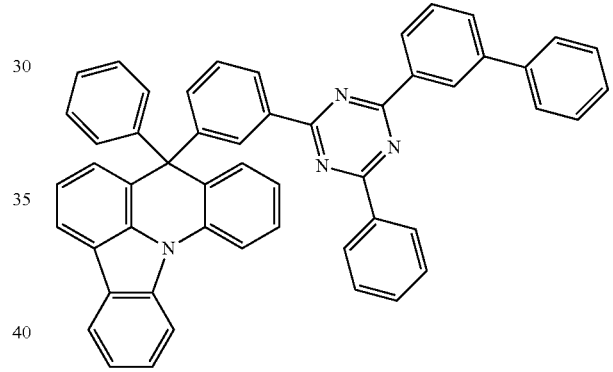
[Compound 24]
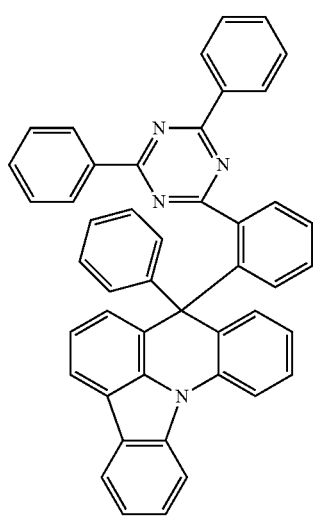

[Compound 25]
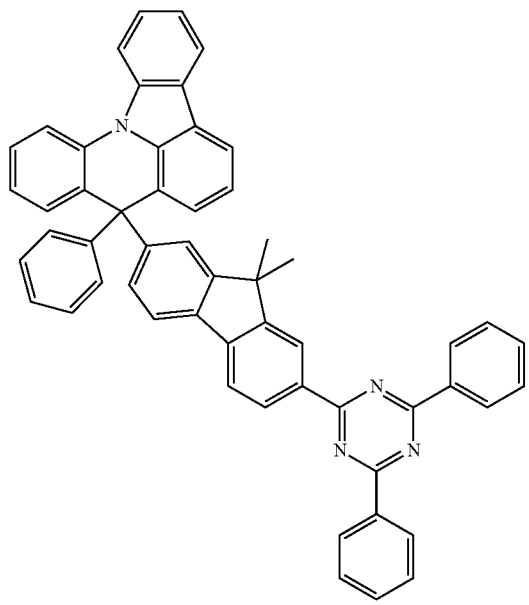
[Compound 27]
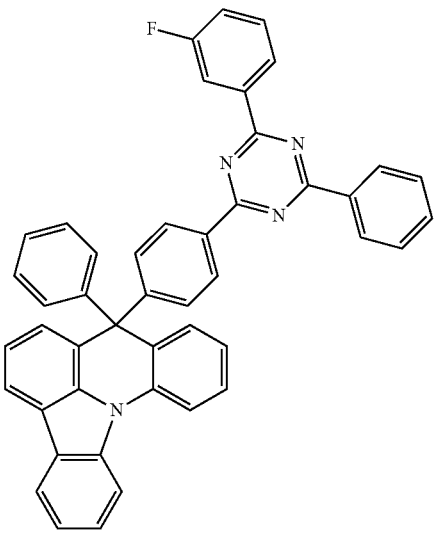
[Compound 26]
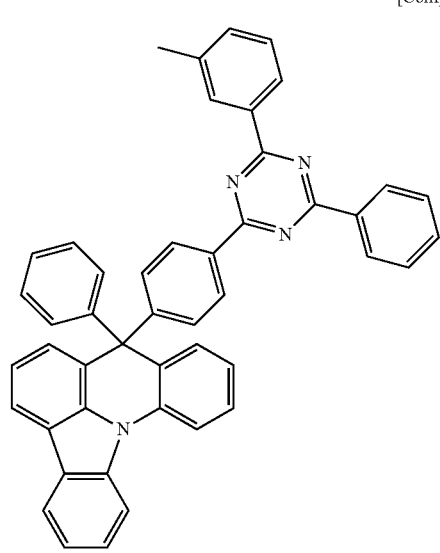
[Compound 28]
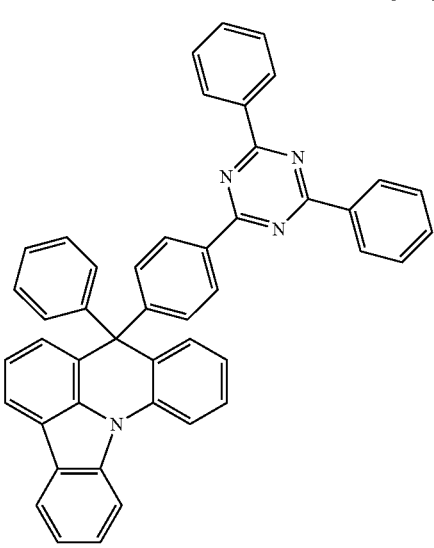

[Compound 29]
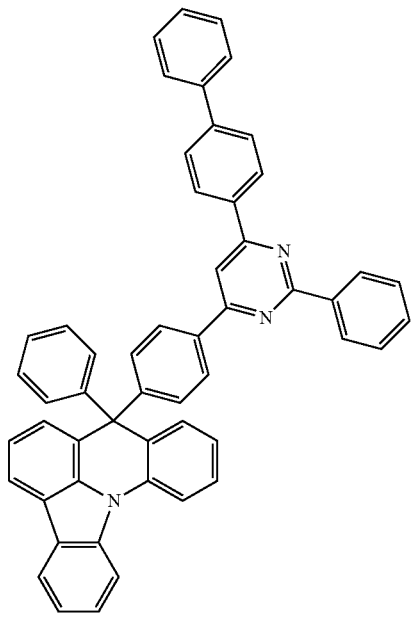
[Compound 30]
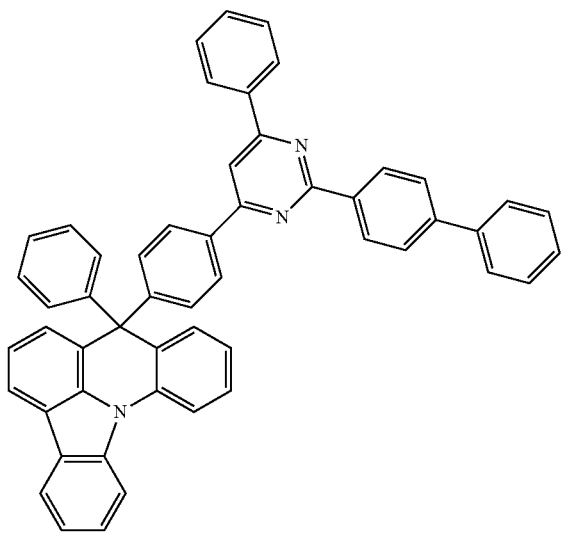
[Compound 31]
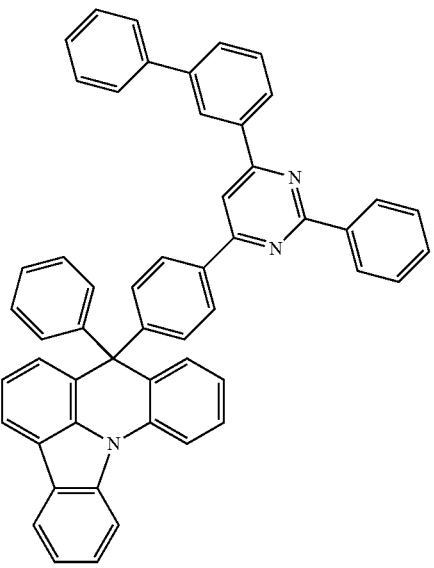
[Compound 32]
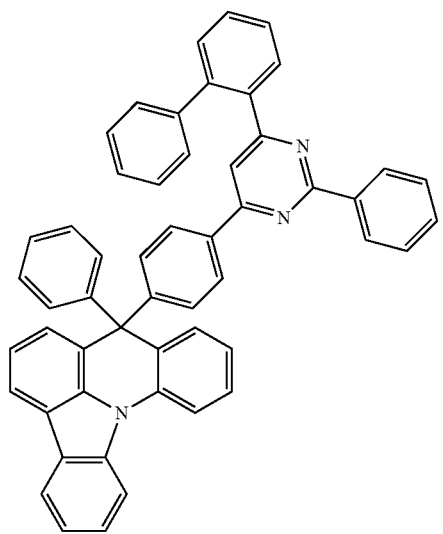

[Compound 33]
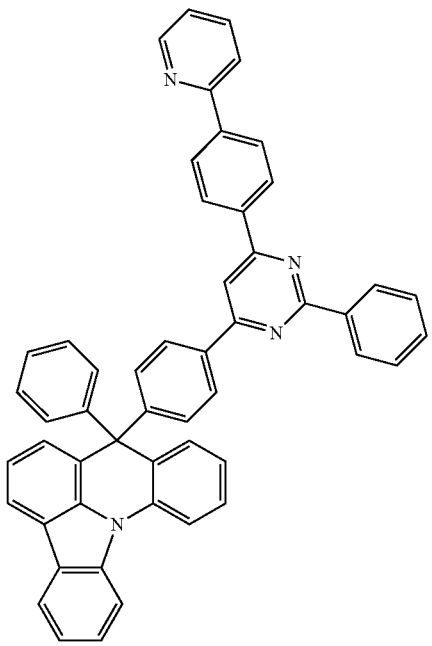
[Compound 34]
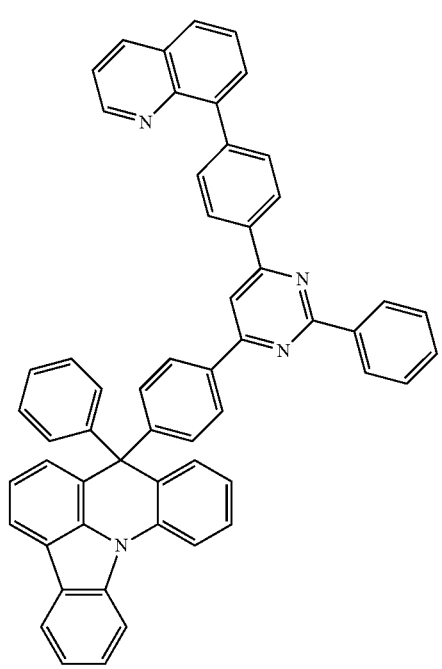
[Compound 35]
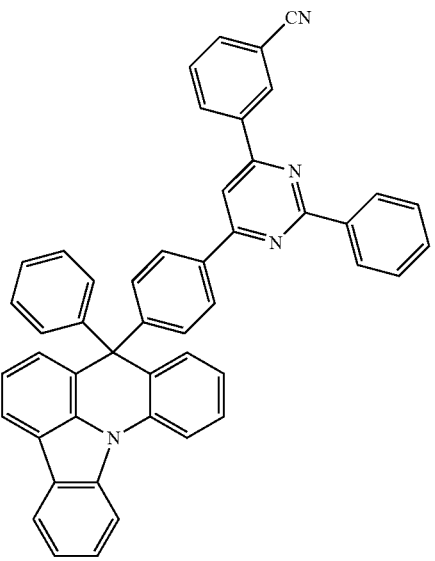
[Compound 36]
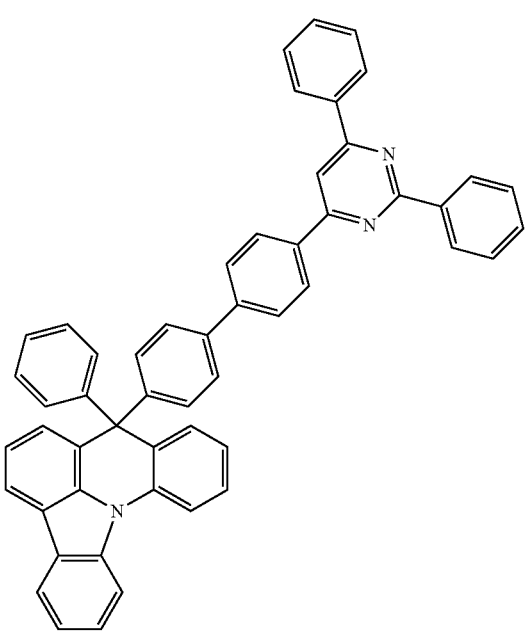

-continued
[Compound 37]
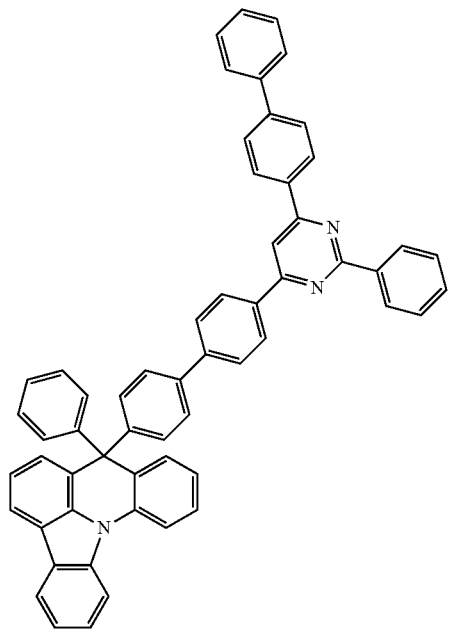
[Compound 38]
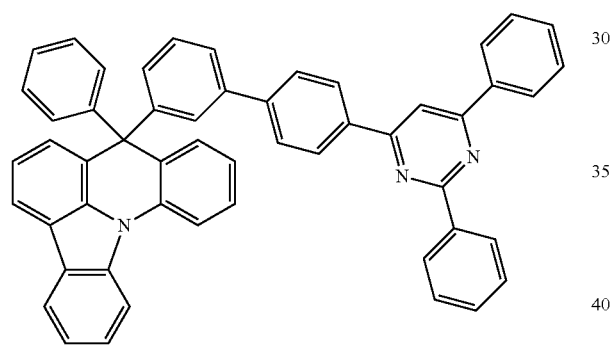
[Compound 39]
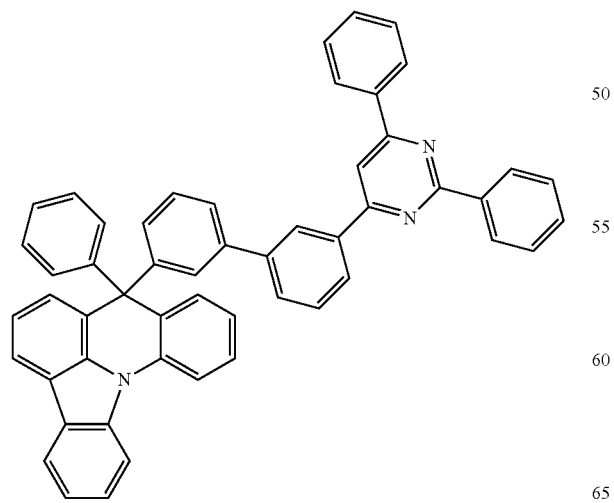
-continued
[Compound 40]
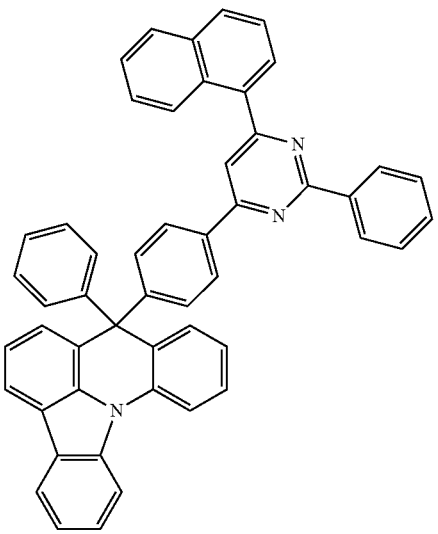
[Compound 41]
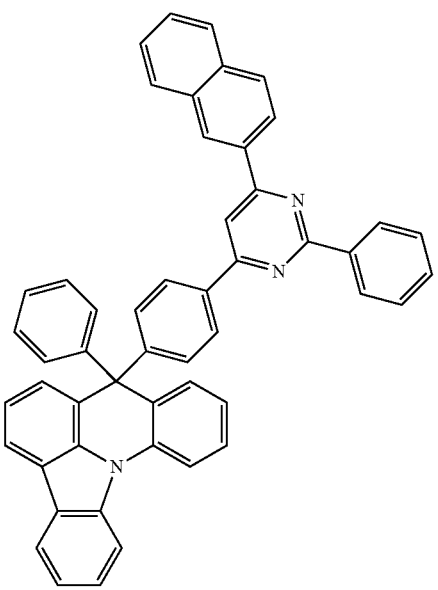

[Compound 42]
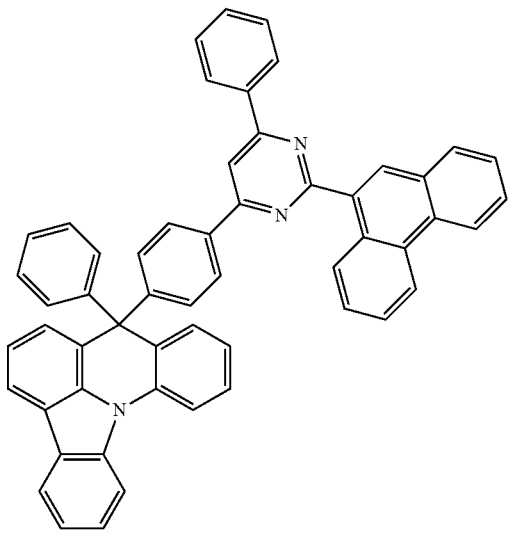
[Compound 43]
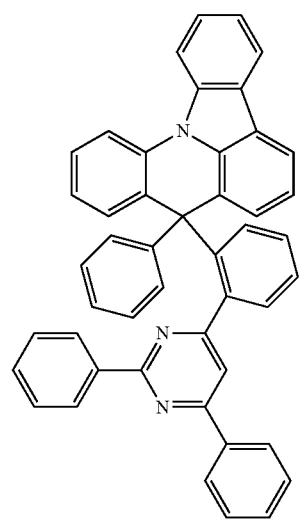
[Compound 44]
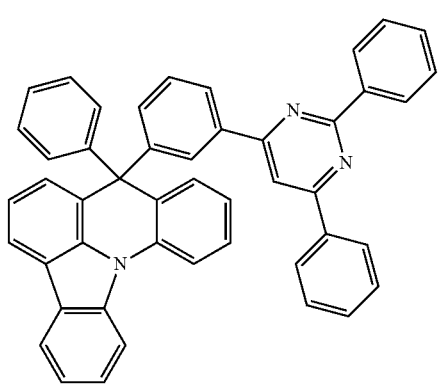
[Compound 45]
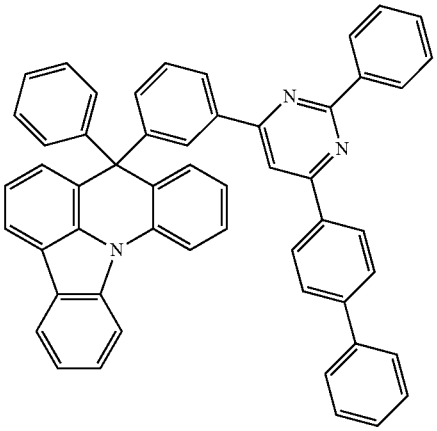
[Compound 46]
[Compound 47]
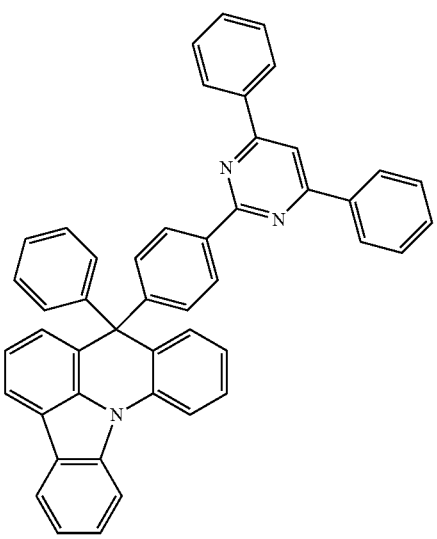

[Compound 48]
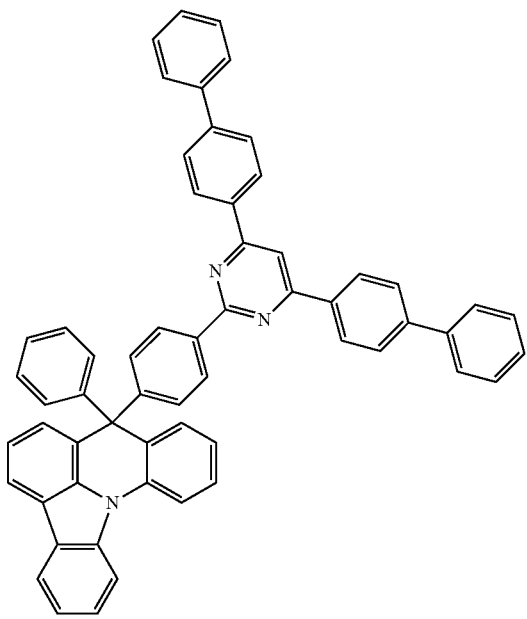
[Compound 49]
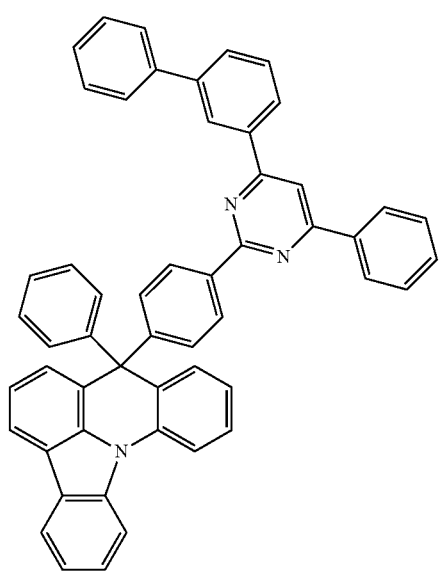
[Compound 50]
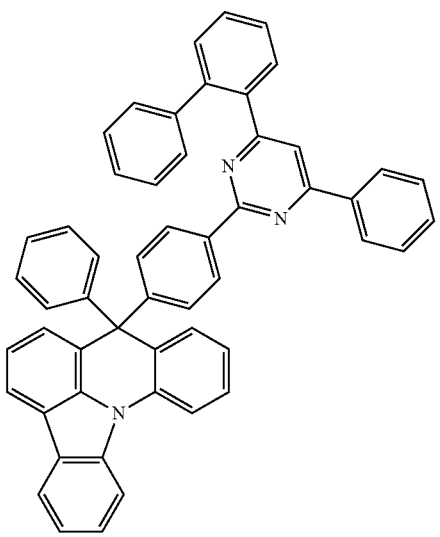
[Compound 51]
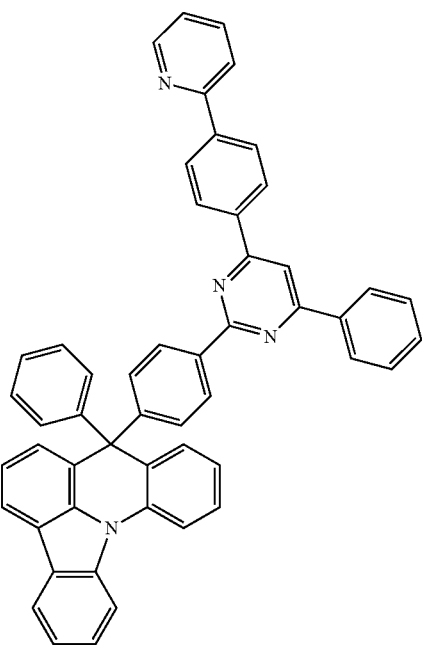

[Compound 52]
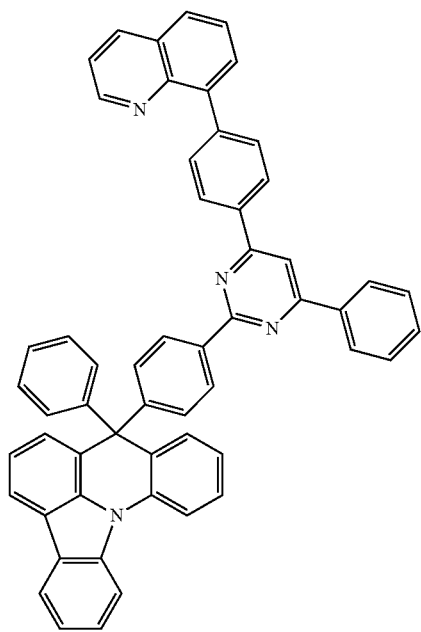
[Compound 53]
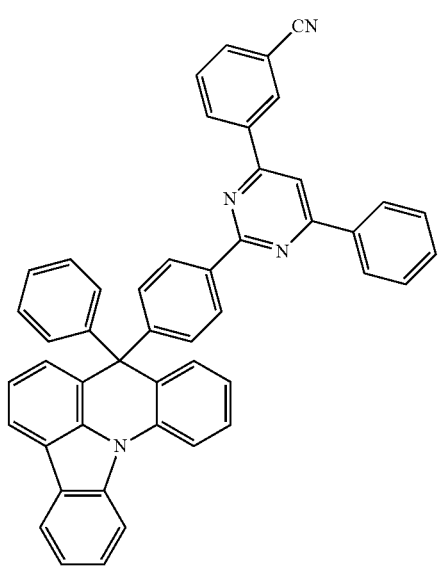
[Compound 54]
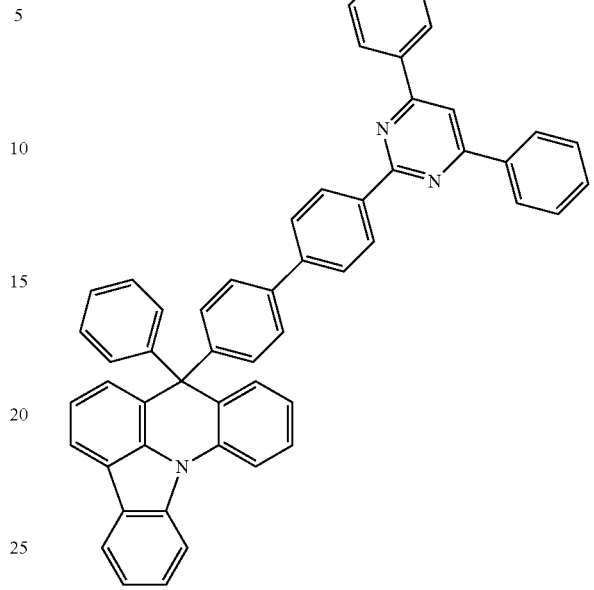
[Compound 55]
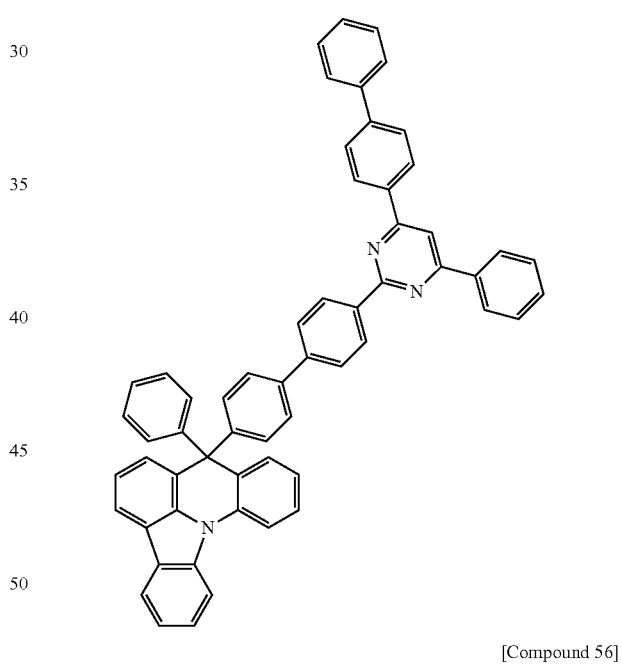
[Compound 56]
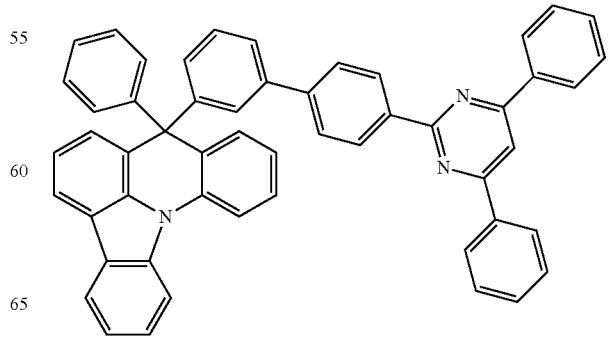

[Compound 57]
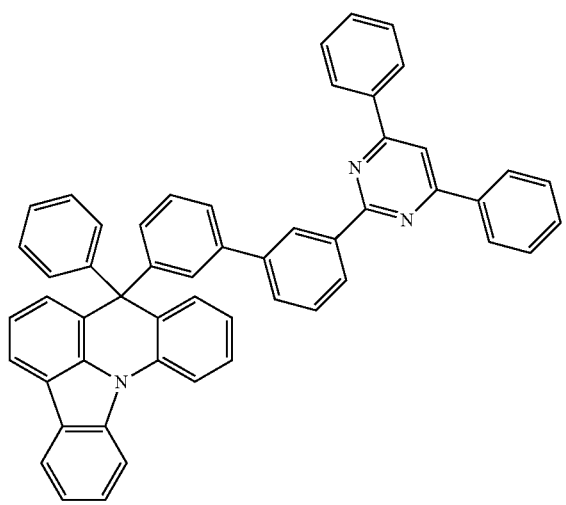
[Compound 58]
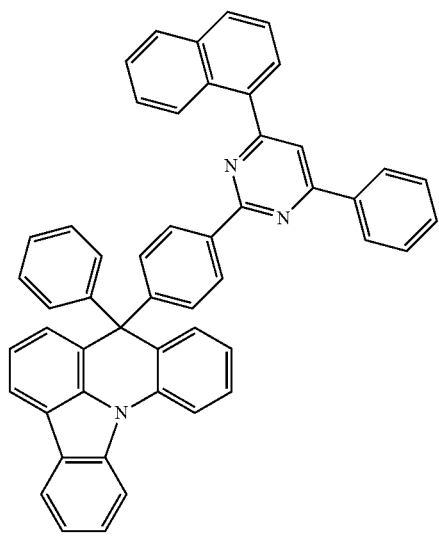
[Compound 59]
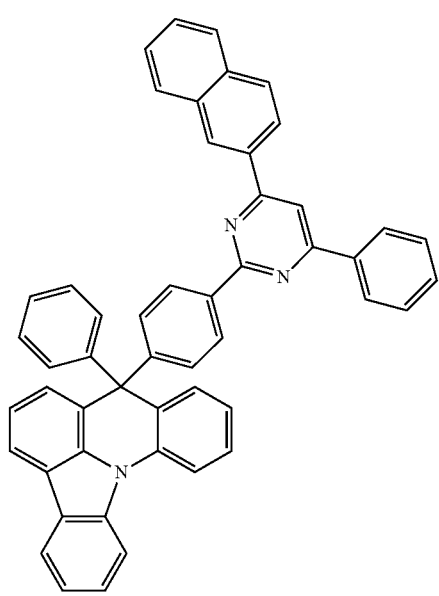
[Compound 60]
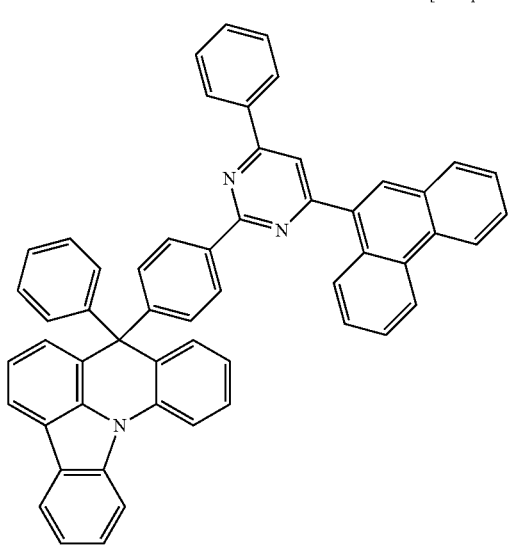
[Compound 61]
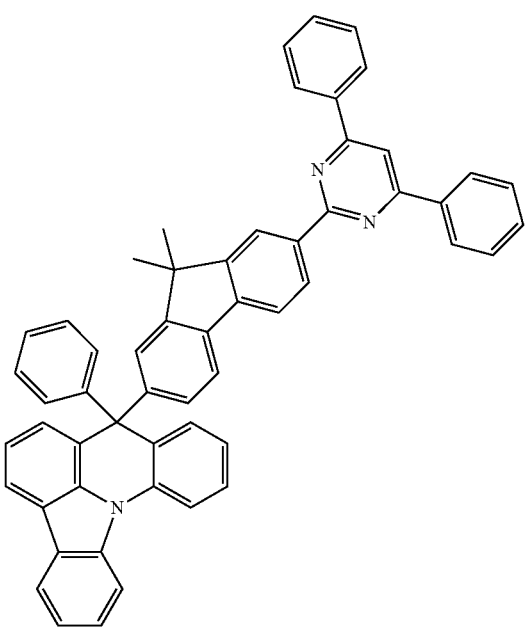

[Compound 62]
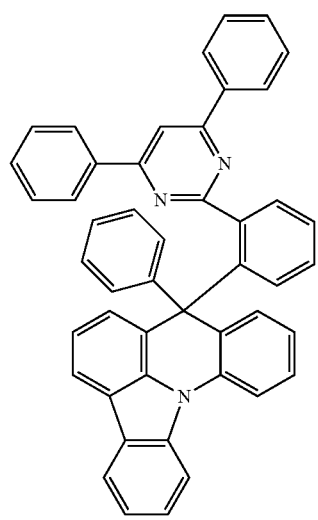
[Compound 63]
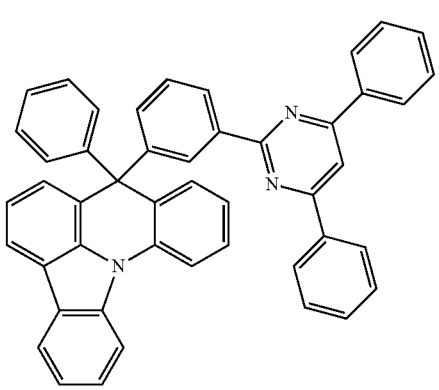
[Compound 64]
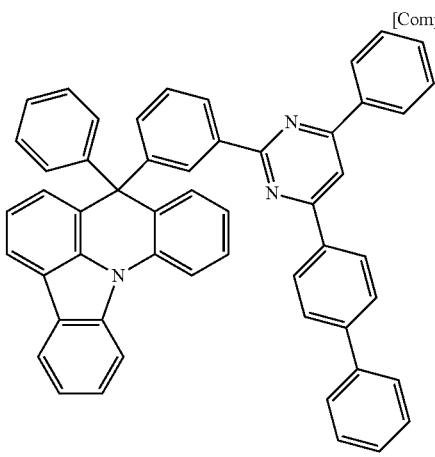
[Compound 65]
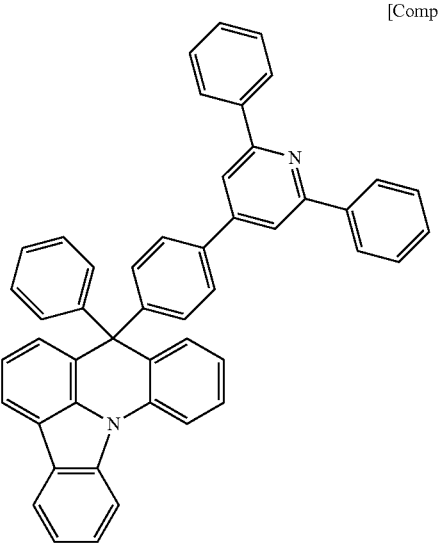
[Compound 66]
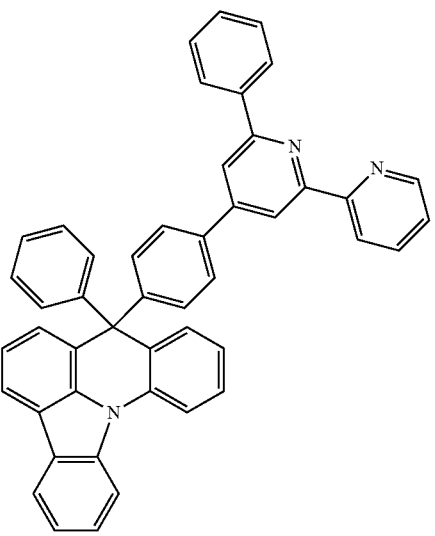
[Compound 67]
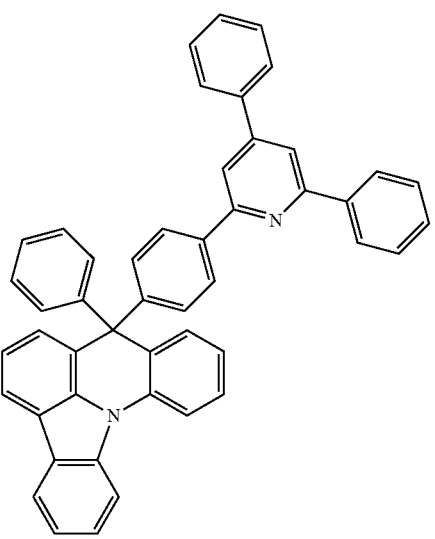

[Compound 68]
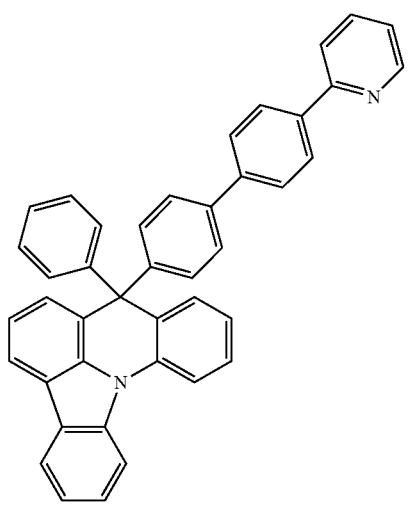
[Compound 69]
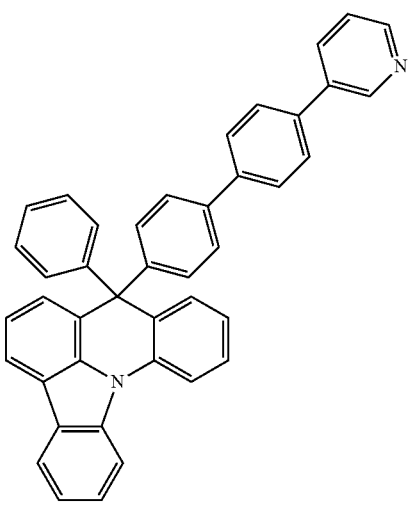
[Compound 70]
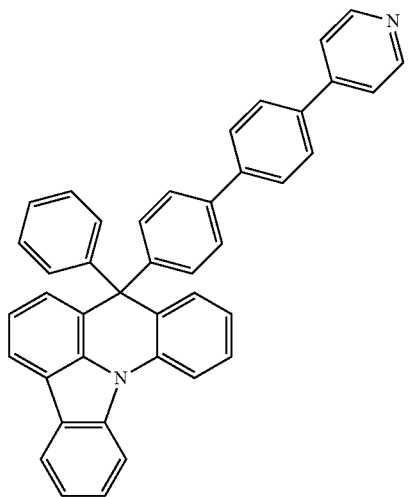
[Compound 71]
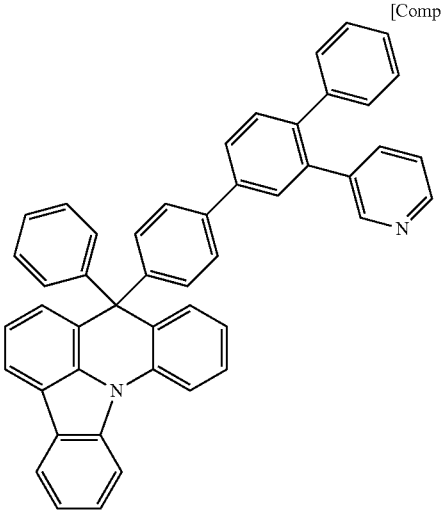
[Compound 72]
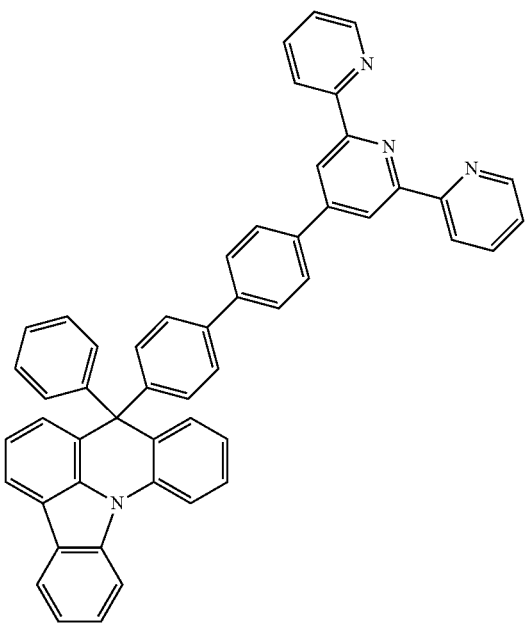

[Compound 73]
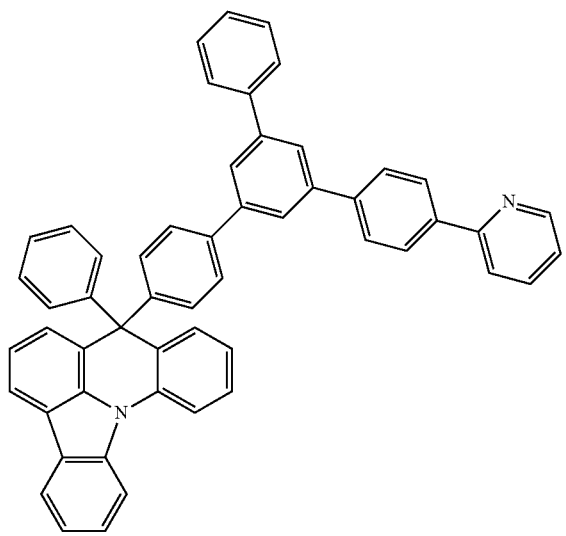
[Compound 74]
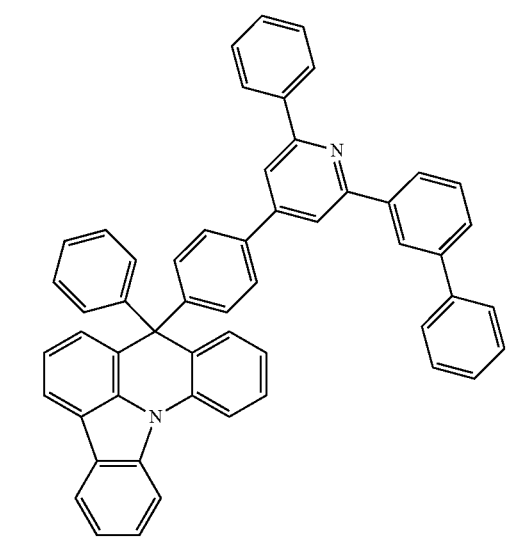
[Compound 75]
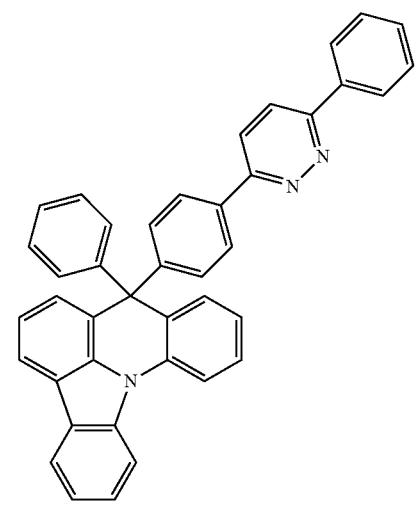
[Compound 76]
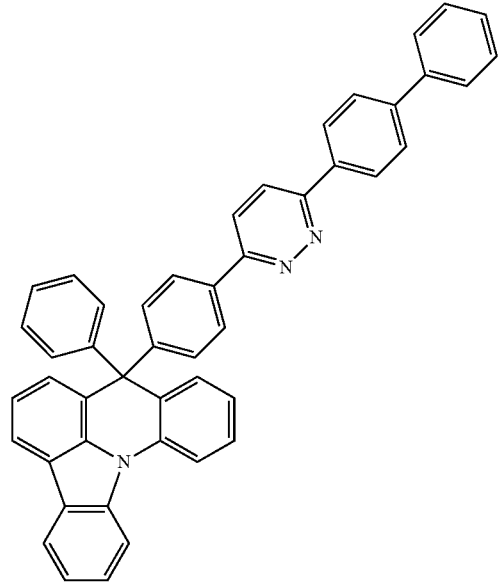
[Compound 77]
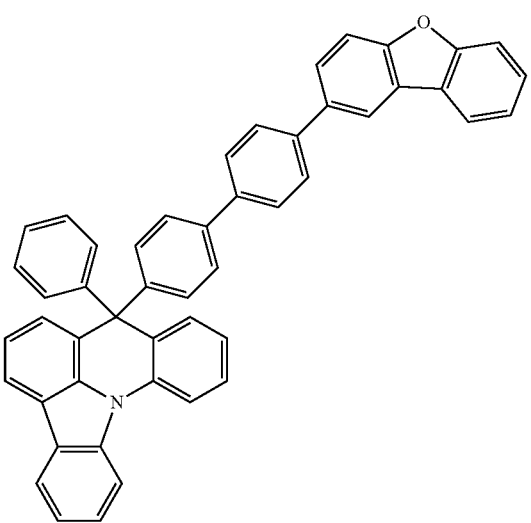
[Compound 78]
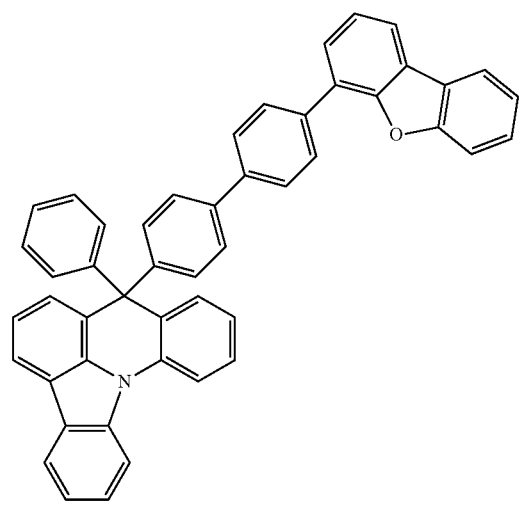

[Compound 79]
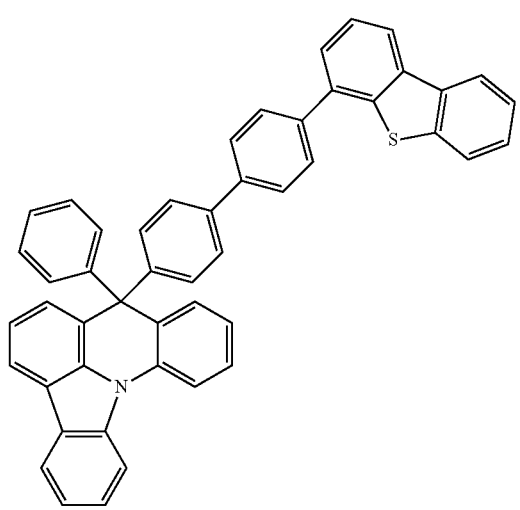
[Compound 80]
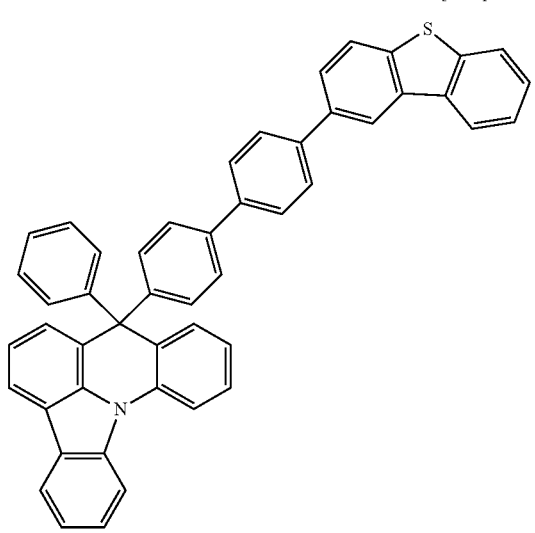
[Compound 81]
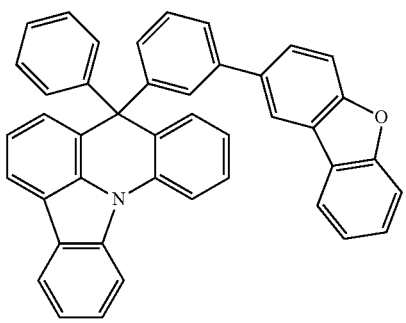
[Compound 82]
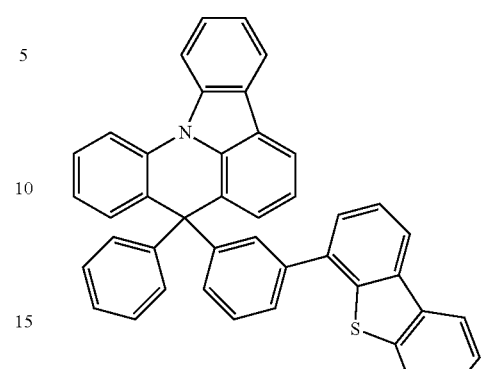
[Compound 83]
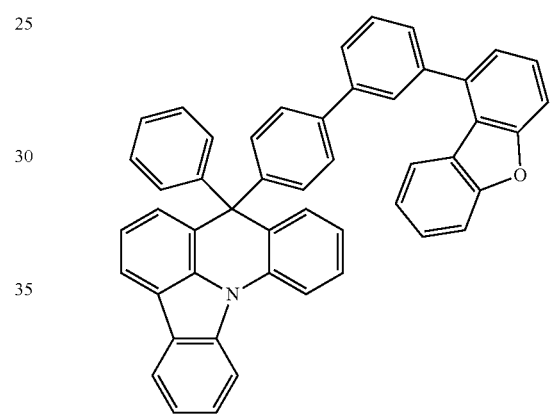
[Compound 84]
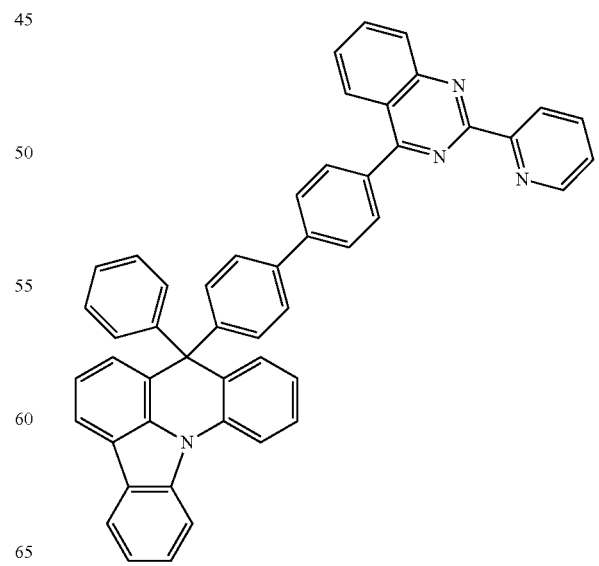

[Compound 85]
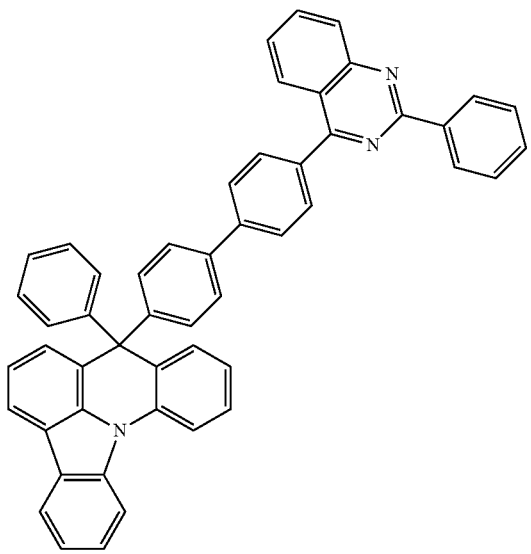
[Compound 86]
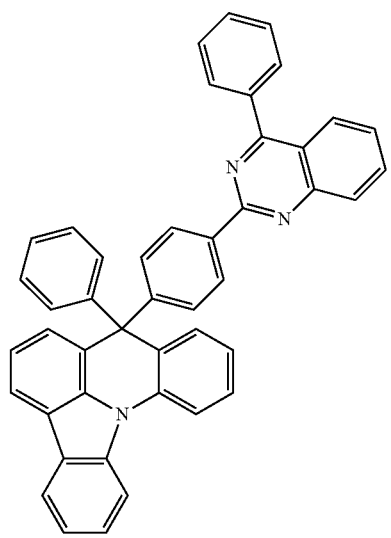
[Compound 87]
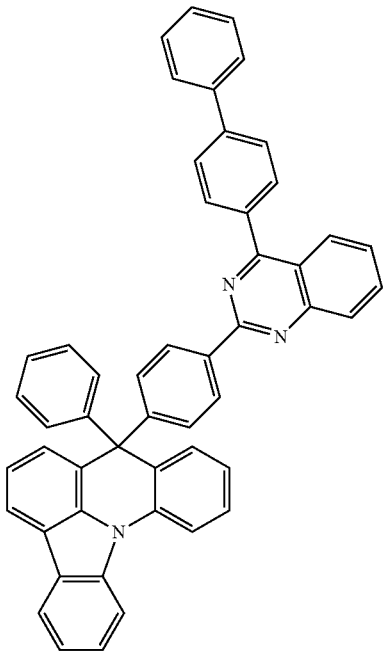
[Compound 88]
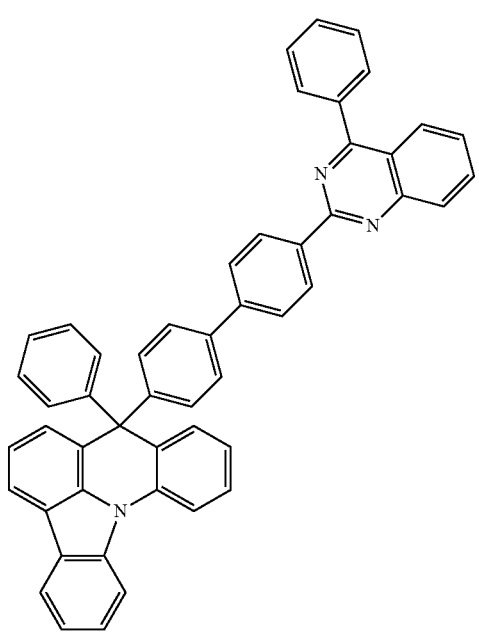

[Compound 89]
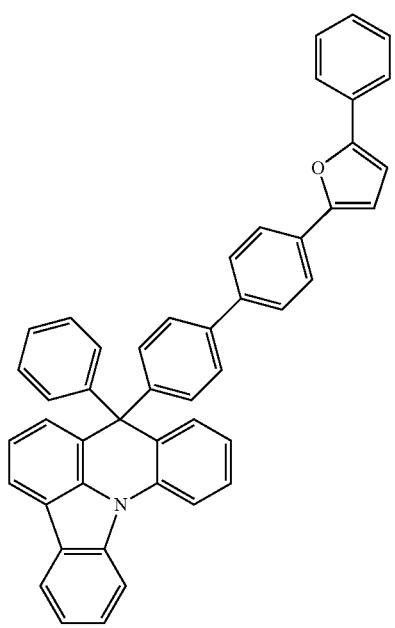
[Compound 90]
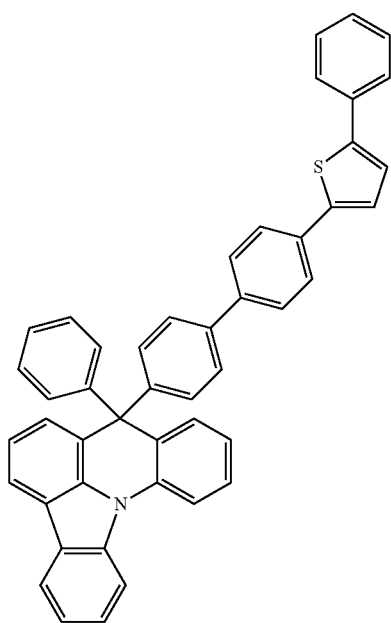
[Compound 91]
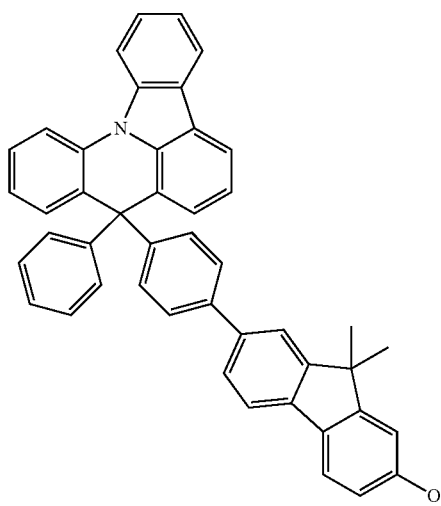
[Compound 92]
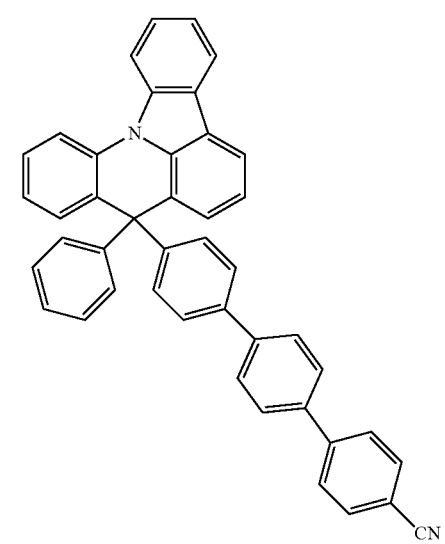
[Compound 93]

[Compound 94]
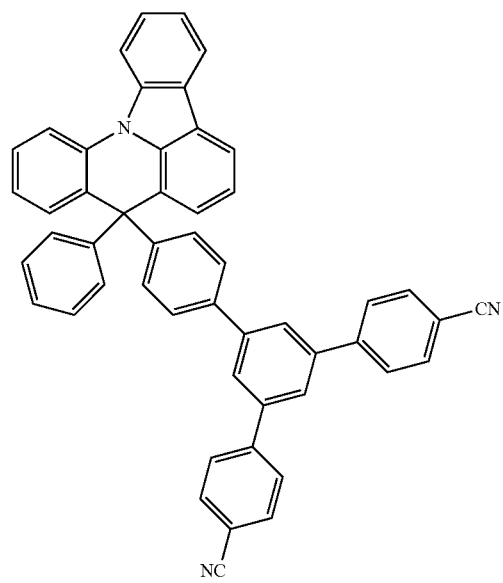
[Compound 95]
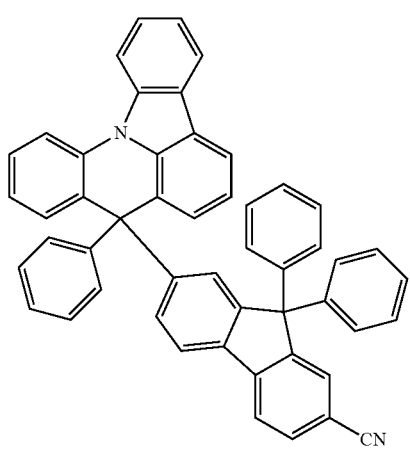
[Compound 96]
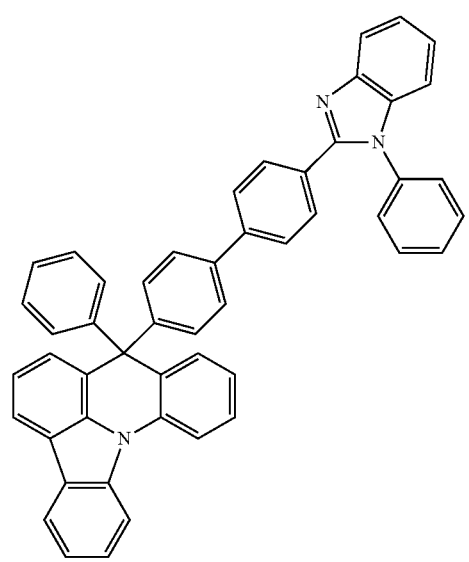
[Compound 97]
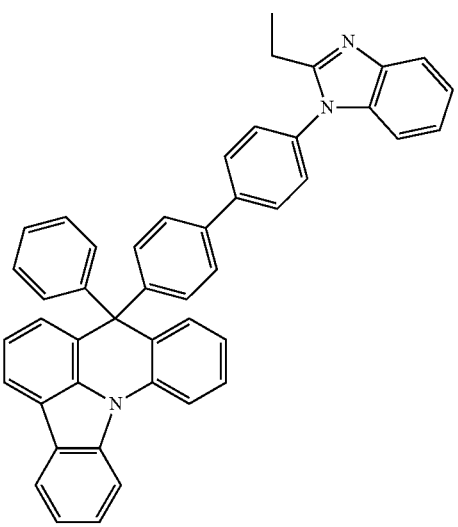
[Compound8]
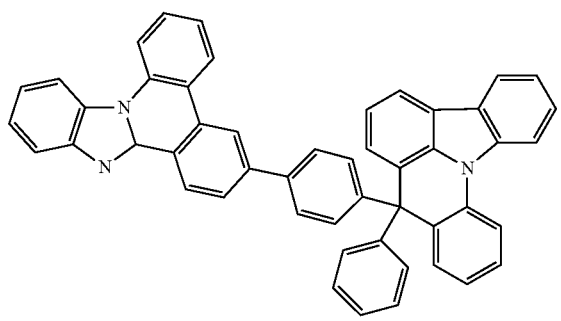
[Compound 99]

[Compound 100]
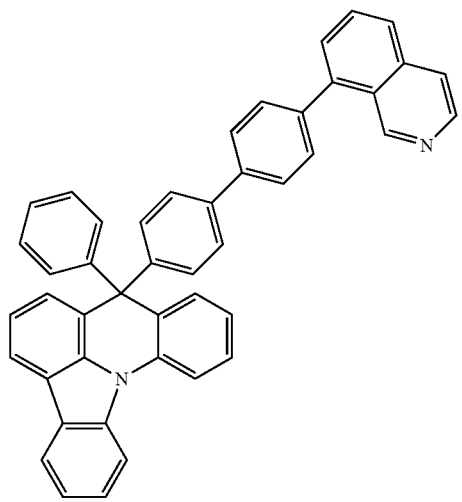
[Compound 102]
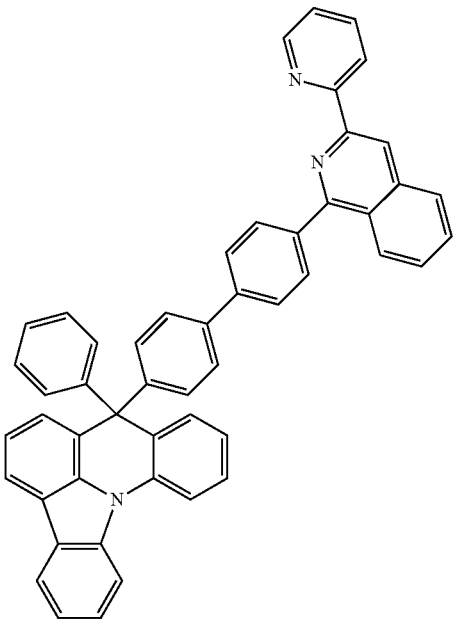
[Compound 101]
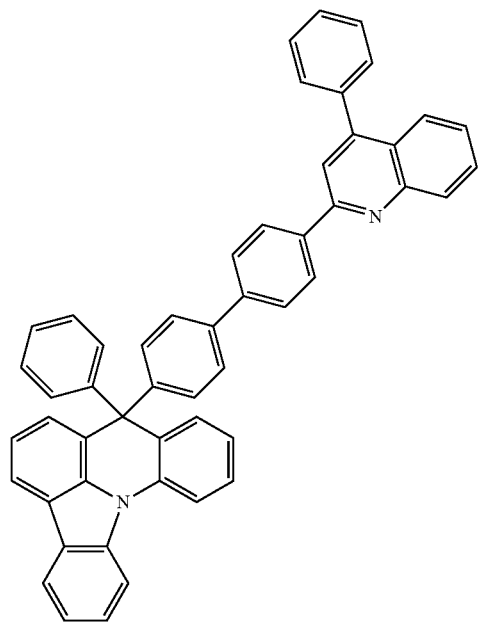
[Compound 103]
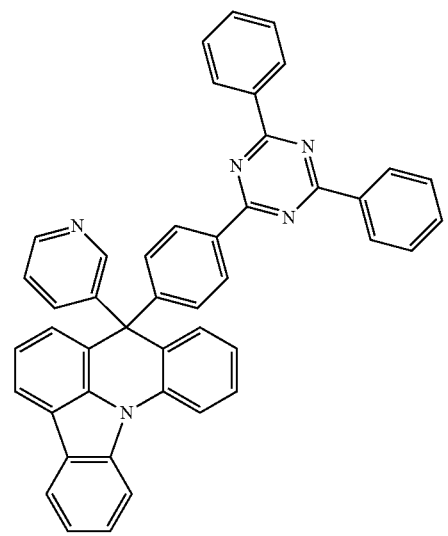

[Compound 104]
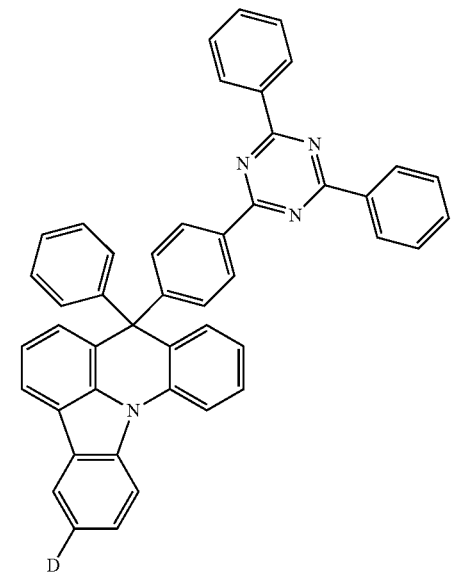
[Compound 105]
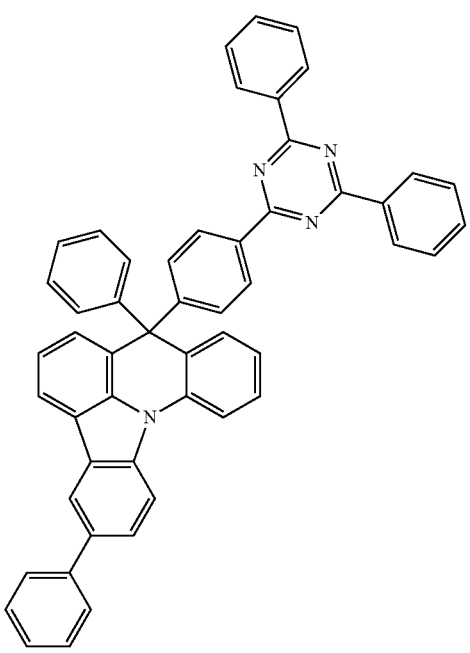
[Compound 106]
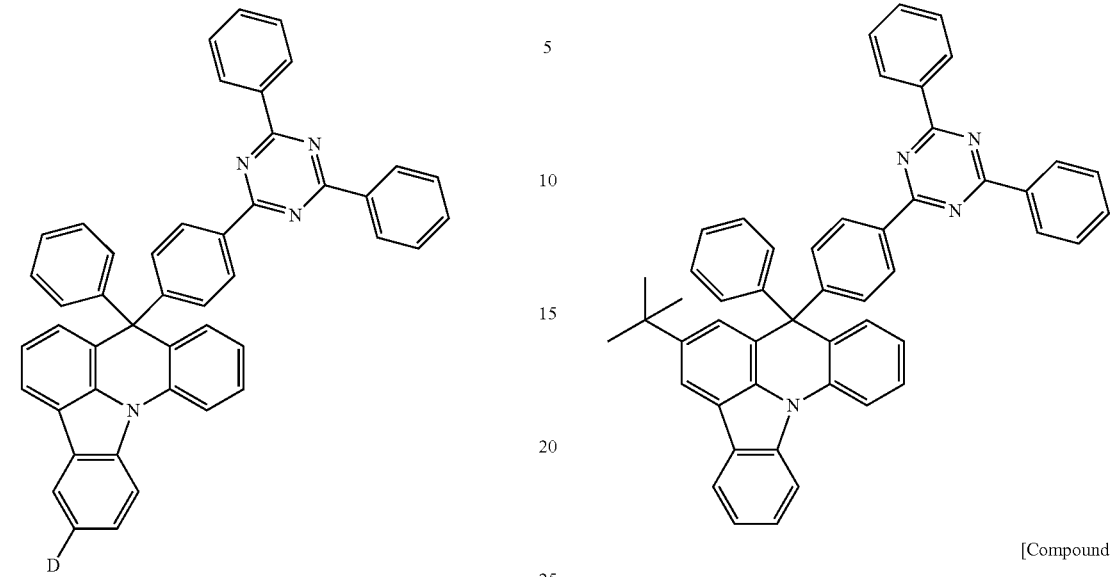
[Compound 107]
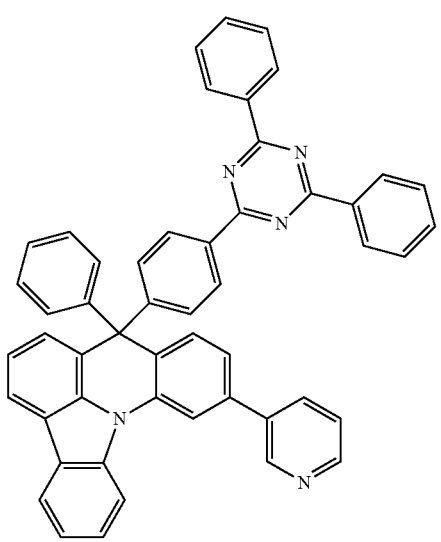
[Compound 108]
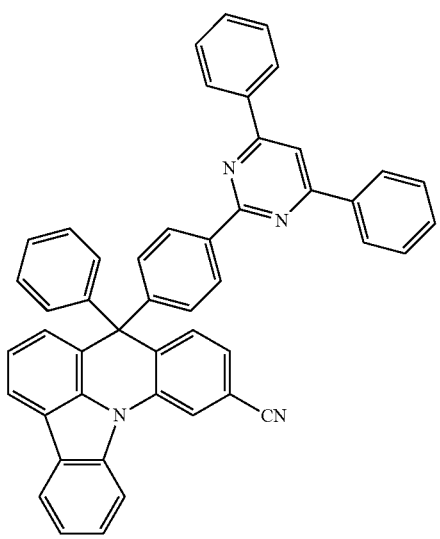

[Compound 109]
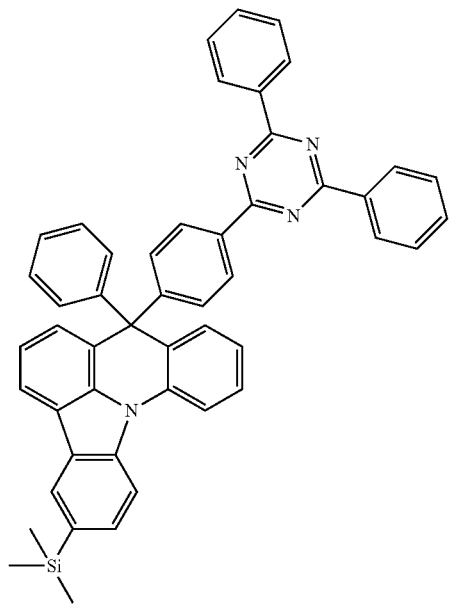
[Compound 110]
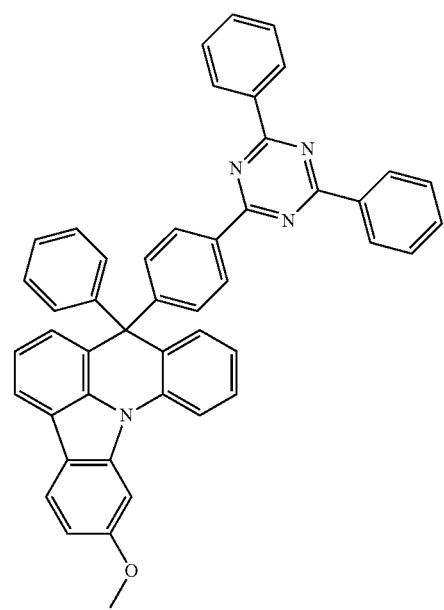
[Compound 111]
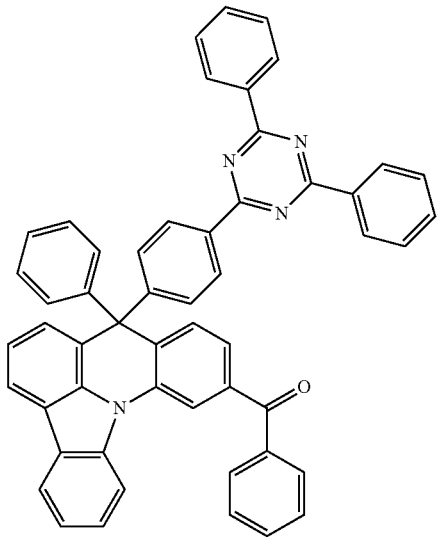
[Compound 112]
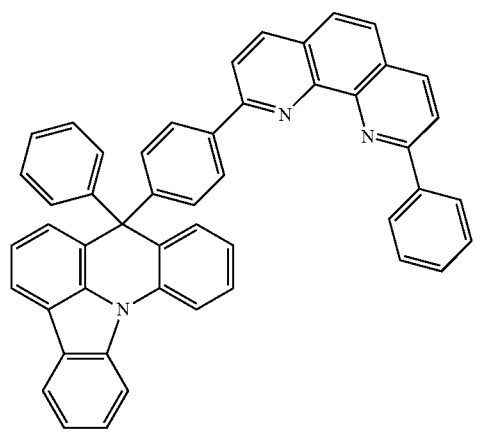
[Compound 113]
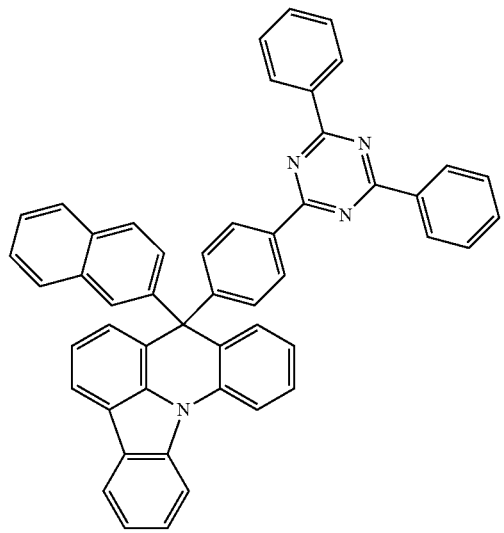

[Compound 114]

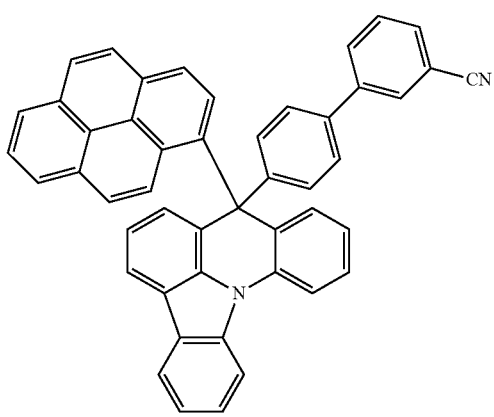

[Compound 115]

[Compound 116]

[Compound 117]

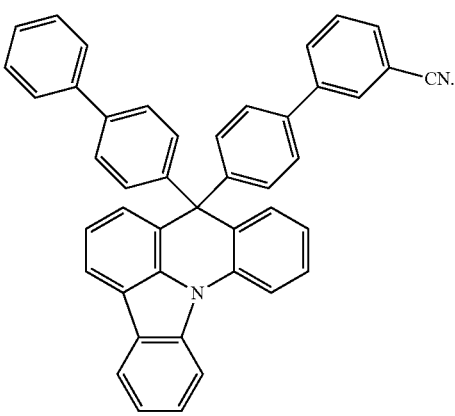

7. An organic light emitting device comprising:
a first electrode;
a second electrode provided to face the first electrode; and
one or more organic material layers provided between the first electrode and the second electrode,
wherein one or more layers of the organic material layers comprise the compound of claim 1.

8. The organic light emitting device of claim 7, wherein the organic material layer comprises an electron transport layer or an electron injection layer, and the electron transport layer or the electron injection layer comprises the compound.

9. The organic light emitting device of claim 7, wherein the organic material layer comprises a light emitting layer, and the light emitting layer comprises the compound.

10. An organic light emitting device comprising:
a first electrode;
a second electrode provided to face the first electrode; and
one or more organic material layers provided between the first electrode and the second electrode,
wherein one or more layers of the organic material layers comprise the compound of claim 6.

11. The organic light emitting device of claim 10, wherein the organic material layer comprises an electron transport layer or an electron injection layer, and the electron transport layer or the electron injection layer comprises the compound.

12. The organic light emitting device of claim 10, wherein the organic material layer comprises a light emitting layer, and the light emitting layer comprises the compound.

* * * * *